(12) United States Patent
Bolchakova et al.

(10) Patent No.: US 8,399,231 B2
(45) Date of Patent: Mar. 19, 2013

(54) ***THERMUS THERMOPHILUS* NUCLEIC ACID POLYMERASES**

(75) Inventors: Elena Bolchakova, Union City, CA (US); James Rozzelle, San Francisco, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/905,008

(22) Filed: Oct. 14, 2010

(65) Prior Publication Data

US 2011/0177497 A1     Jul. 21, 2011

Related U.S. Application Data

(60) Continuation of application No. 12/193,691, filed on Aug. 18, 2008, now abandoned, which is a division of application No. 11/609,174, filed on Dec. 11, 2006, now Pat. No. 7,422,872, which is a division of application No. 10/303,110, filed on Nov. 22, 2002, now Pat. No. 7,148,340.

(60) Provisional application No. 60/336,046, filed on Nov. 30, 2001.

(51) Int. Cl.
*C07K 1/00*     (2006.01)
*C12N 9/00*     (2006.01)

(52) U.S. Cl. ........................ 435/183; 435/975; 530/350

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 5,079,352 A | 1/1992 | Gelfand et al. |
| 5,455,170 A | 10/1995 | Abramson et al. |
| 5,466,591 A | 11/1995 | Abramson et al. |
| 5,614,365 A | 3/1997 | Tabor et al. |
| 5,614,402 A | 3/1997 | Dahlberg et al. |
| 5,674,738 A | 10/1997 | Abramson et al. |
| 6,555,506 B2 | 4/2003 | Hopkins et al. |
| 7,148,340 B2 | 12/2006 | Rozzelle et al. |
| 7,422,872 B2 | 9/2008 | Rozzelle et al. |
| 2009/0209008 A1 | 8/2009 | Rozzelle et al. |

FOREIGN PATENT DOCUMENTS

| | | |
|---|---|---|
| EP | 0482714 A1 | 4/1992 |
| EP | 0517418 A2 | 12/1992 |
| EP | 0655506 A1 | 5/1995 |
| EP | 0745676 A1 | 12/1996 |
| WO | 91/01384 A1 | 2/1991 |
| WO | 91/09950 A1 | 7/1991 |
| WO | WO91/09950 * | 7/1991 |
| WO | 92/06188 A2 | 4/1992 |

OTHER PUBLICATIONS

Altschul, Stephen F. et al., "Basic Local Alignment Search Tool", *Journal of Molecular Biology*, vol. 215, 1990, 403-410.
Altschul, Stephen F. et al., "Gapped BLAST and PSI-BLAST: a new generation of protein database search", *Nucleic Acids Research*, vol. 25, No. 17, Sep. 1997, 3389-3402.
Asakura, K et al., "Cloning Nucleotide Sequence and Expression In *Escherichia coli* of DNA Polymerase Gene (Pola) From *Thermus thermophilus* HB8", *Journal of Fermentation and Bioengineering, Society of Fermentation Technology*, 1993, 265-269.
Barnes, , "The Fidelity of Taq Polymerase Catalyzing PCR is Improved by an N-Terminal Deletion", *Gene*, vol. 112, No. 1, Mar. 1, 1992, 29-35.
Batzer, M A. et al., "Enhanced Evolutionary PCR Using Oligonucleotides With Inosine at the 3'-Terminus", *Nucl. Acids Res.*, Oxford University Press, Sep. 1991, 19:5081.
Corpet, et al., "Multiple sequence alignment with hierarchical clustering", *Nucleic Acids Res.* 16, 1988, 10881-90.
EP 02789862.6, , "Supplement European Search Report for EP 02789862.6", Mailed Jan. 24, 2005, 6 pages.
Erlich, et al., "Recent Advances in the Polymerase Chain Reaction", *Science Magazine*, vol. 252, No. 5013, Jun. 21, 1991, 1643-1650.
Henikoff, et al., "Amino acid substitution matrices from protein blocks", *Proc. Natl. Acad. Sci. USA*, 89, 10915 (1989, 1992, 10915-10919.
Higgins, et al., *Gene* 73:237-244, 1988, Higgins DG, Sharp PM. CLUSTAL: a package for performing multiple sequence alignment on a microcomputer. Gene. Dec. 15, 1988;73(1):237-244.
Higgins, et al., *CABIOS* 5:151-153, 1989, Higgins DG, Sharp PM. Fast and sensitive multiple sequence alignments on a microcomputer. Comput Appl Biosci. Apr. 1989;5(2):151-153.
Huang, et al., *CABIOS 8*, 1992, 155-165.
Kwon, et al., "*Thermus aquaticus caldophilus* Thermostable DNA Polymerase Gene", *Database GenEmbl*, Accession No. U62584,, Oct. 21, 1997.
Kwon, S T. et al., "D.S. Cloning and analysis of the DNA polymerase-encoding gene from *Thermus caldophilus* GK24", *Mol. Cells*. 1997. vol. 7 (2), 264-271.
Lawyer, et al., "Isolation, Characterization, and Expression in *Escherichia coli* of the DNA Polymerase Gene from *Thermus aquaticus*", *The Journal of Biological Chemistry*, vol. 264, No. 11, Apr. 15, 1989, 6427-6437.
Lawyer, Frances C. et al., "High-level Expression, Purification, and Enzymatic characterization of Full-length *Thermus aquaticus* DNA polymerase and a Truncated Form Deficient in 5' to 3' Exonuclease activity", *PCR Methods and Applications*, , vol. 2, No. 4, Cold Spring Harbor Laboratory Press,, May 1993, 275-287.
Meinkoth, J et al., "Hybridization of Nucleic Acids Immobilized on Solid Supports", *Anal. Biochem.*, Academic Press, Inc., 1984, 138:267-284.
Ohtsuka, E et al., "An Alternative Approach to Deoxyoligonucleotides as Hybridization Probes by Insertion of Deoxyinosine and Ambiguous Codon Positions", *J. Biol. Chem.*, vol. 260(5), American Society of Biological Chemists, Inc., vol. 260, No. 5, 1985, 2605-2608.

(Continued)

*Primary Examiner* — Albert Navarro

(57) ABSTRACT

The invention provides novel nucleic acid polymerases from strains GK24 and RQ-1 of *Thermus thermophilus*, and nucleic acids encoding those polymerases, as well as methods for using the polymerases and nucleic acids.

13 Claims, 6 Drawing Sheets

OTHER PUBLICATIONS

PCT/US02/37734, , "International Search Report", Jun. 12, 2003.

Pearson, et al., *Meth. Mol. Biol. 24*, 1994, 307-331.

Rossolini, et al., "Use of deoxyinosine-containing primers vs degenerate primers for polymerase chain reaction based on ambiguous sequence information", *Molecular and Cellular Probes*; vol. 8, Issue 2, Apr. 1994, pp. 91-98, 91-98.

Sawano, et al., "Directed evolution of green fluorescent protein by a new versatile PGR strategy for site-directed and semi-random mutagenesis", *Nucleic Acids Res.* vol. 28 (16), . 2000. : E78., 2000, i-vii.

Shima, Yasufumi et al., "Construction and Characterization of N-Terminally Truncated DNA Polymerase from *Thermus thermophilus*", *Journal of Fermentation and Bioengineering*, vol. 81., No. 6., 1996. XP002300266 ISSN:0922-338X, Elsevier B.V., New York, 1996, 504-510.

Tabor, Stanley et al., "A Single Residue in DNA Polymerases of the *Escherichia coli* DNA Polymerase I Family is Critical for Distinguishing Between Deoxy- and Dideoxyriboncleotides", *Biochemistry*, vol. 92, No. 14, Proceedings of the National Academy of Sciences (PNAS). National Academy of Sciences, USA, Jul. 1995, 6339-6343.

Vainshtein, et al., "Peptide rescue of an N-terminal truncation of the Stoffel fragment of Taq DNA polymerase", *Protein Science 5*, 1996, 1785-1792.

Xu, Yang et al., "Biochemical and Mutational Studies of the 5'-3' Exonuclease of DNA Polymerase I of *Escherichia coli*", *Journal of Molecular Biology*, vol. 268, No. 2, Academic Press Limited, May 2, 1997, 284-302.

\* cited by examiner

FIGURE 1A

```
            1                                                    50
Tth HB8     MEAMLPLFEP KGRVLLVDGH HLAYRTFFAL KGLTTSRGEP VQAVYGFAKS
Tth Z05     MKAMLPLFEP KGRVLLVDGH HLAYRTFFAL KGLTTSRGEP VQAVYGFAKS
Tth GK24    MEAMLPLFEP KGRVLLVDGH HLAYRTFFAL KGLTTSRGEP VQAVYGFAKS
ABi GK24    MEAMLPLFEP KGRVLLVDGH HLAYRTFFAL KGLTTSRGEP VQAVYDFAKS 51                                                   100
Tth HB8     LLKALKEDGY KAVFVVFDAK APSFRHEAYE AYKAGRAPTP EDFPRQLALI
Tth Z05     LLKALKEDGY KAVFVVFDAK APSFRHEAYE AYKAGRAPTP EDFPRQLALI
Tth GK24    LLKALKEDGY KAVFVVFDAK APSFRHEAYE AYKAGRAPTP EDFPRQLALI
ABi GK24    LLKALKEDGY KAVFVVFDAK APSFRHEAYE AYKAGRAPTP EDFPRQLALI 101                                                  150
Tth HB8     KELVDLLGFT RLEVPGYEAD DVLATLAKKA EKEGYEVRIL TADRDLYQLV
Tth Z05     KELVDLLGFT RLEVPGFEAD DVLATLAKKA EREGYEVRIL TADRDLYQLV
Tth GK24    KELVDLLGFT RLEVPGYEAD DVLATLAKNP EKEGYEVRIL TADRDLIQLV
ABi GK24    KELVDLLGFT RLEVPGFEAD DVLATLAKKA EKEGYEVRIL TADRDLYQLV 151                                                  200
Tth HB8     SDRVAVLHPE GHLITPEWLW EKYGLRPEQW VDFRALVGDP SDNLPGVKGI
Tth Z05     SDRVAVLHPE GHLITPEWLW EKYGLKPEQW VDFRALVGDP SDNLPGVKGI
Tth GK24    SDRVAVLHPE GHLITPEWLW QKYGLKPEQW VDFRALVGDP SDNLPGVKGI
ABi GK24    SDRVAVLHPE GHLITPEWLW QKYGLKPEQW VDFRALVGDP SDNLPGVKGI 201                                                  250
Tth HB8     GEKTALKLLK EWGSLENLLK NLDRVKPERV REKIKAHLED LRLSLELSRV
Tth Z05     GEKTALKLLK EWGSLENILK NLDRVKPESV RESIKAHLED LKLSLELSRV
Tth GK24    GEKTALKLLK EWGSLENLLK NLDRVKPENV REKIKAHLED LRLSLELSRV
ABi GK24    GEKTALKLLK EWGSLENLLK NLDRVKPENV REKIKAHLED LRLSLELSRV 251                                                  300
Tth HB8     RTDLPLEVDL AQGREPDREG LRAFLERLEF GSLLHEFGLL EAPAPLEEAP
Tth Z05     RSDLPLEVDF ARRREPDREG LRAFLERLEF GSLLHEFGLL EAPAPLEEAP
Tth GK24    RTDLPLEVDL AQGREPDREG LRAFLERLEF GSLLHEFGLL EAPAPLEEAP
ABi GK24    RTDLPLEVDL AQGREPDREG LRAFLERLEF GSLLHEFGLL EAPAPLEEAP 301                                                  350
Tth HB8     WPPPEGAFVG FVLSRPEPMW AELKALAACR DGRVHRAADP LAGLKDLKEV
Tth Z05     WPPPEGAFVG FVLSRPEPMW AELKALAACR EGRVHRAKDP LAGLKDLKEV
Tth GK24    WPPPEGAFVG FVLSRPEPMW AELKALAACR DGRVHRAADP LAGLKDLKEV
ABi GK24    WPPPEGAFVG FVLSRPEPMW AELKALAACR DGRVHRAADP LAGLKDLKEV 351                                                  400
Tth HB8     RGLLAKDLAV LASREGLDLV PGDDPMLLAY LLDPSNTTPE GVARRYGGEW
Tth Z05     RGLLAKDLAV LALREGLDLA PSDDPMLLAY LLDPSNTTPE GVARRYGGEW
Tth GK24    RGLLAKDLAV LASREGLDLV PGDDPMLLAY LLDPSNTTPE GVARRYGGEW
ABi GK24    RGLLAKDLAV LASREGLDLV PGDDPMLLAY LLDPSNTTPE GVARRYGGEW
```

FIGURE 1B

```
              401                                                          450
Tth HB8       TEDAAHRALL SERLHRNLLK RLEGEEKLLW LYHEVEKPLS RVLAHMEATG
Tth Z05       TEDAAHRALL AERLQQNLLE RLRGEEKLLW LYQEVEKPLS RVLAHMEATG
Tth GK24      TEDAAHRALL SERLHRNLLK RLQGEEKLLW LYHEVEKPLS RVLAHMEATG
ABi GK24      TEDAAHRALL SERLHRNLLK RLQGEEKLLW LYHEVEKPLS RVLAHMEATG 451                                                          500
Tth HB8       VRLDVAYLQA LSLELAEEIR RLEEEVFRLA GHPFNLNSRD QLERVLFDEL
Tth Z05       VRLDVAYLKA LSLELAEEIR RLEEEVFRLA GHPFNLNSRD QLERVLFDEL
Tth GK24      VRLDVAYLQA LSLELAEEIR RLEEEVFRLA GHPFNLNSRD QLERVLFDEL
ABi GK24      VRLDVAYLQA LSLELAEEIR RLEEEVFRLA GHPFNLNSRD QLERVLFDEL 501                                                          550
Tth HB8       RLPALGKTQK TGKRSTSAAV LEALREAHPI VEKILQSREL TKLKNTYVDP
Tth Z05       RLPALGKTQK TGKRSTSAAV LEALREAHPI VEKILQHREL TKLKNTYVDP
Tth GK24      RLPALGKTQK TGKRSTSAAV LEALREAHPI VEKILQHREL TKLKNTYVDP
ABi GK24      RLPALGKTQK TGKRSTSAAV LEALREAHPI VEKILQRREL TKLKNTYVDP 551                                                          600
Tth HB8       LPSLVHPRTG RLHTRFNQTA TATGRLSSSD PNLQNIPVRT PLGQRIRRAF
Tth Z05       LPGLVHPRTG RLHTRFNQTA TATGRLSSSD PNLQNIPIRT PLGQRIRRAF
Tth GK24      LPSLVHPNTG RLHTRFNQTA TATGRLSSSD PNLQNIPVRT PLGQRIRRAF
ABi GK24      LPSLVHPNTG RLHTRFNQTA TATGRLSSSD PNLQNIPVRT PLGQRIRRAF 601                                                          650
Tth HB8       VAEAGWALVA LDYSQIELRV LAHLSGDENL IRVFQEGKDI HTQTASWMFG
Tth Z05       VAEAGWALVA LDYSQIELRV LAHLSGDENL IRVFQEGKDI HTQTASWMFG
Tth GK24      VAEAGWALVA LDYSQIELRV LAHLSGDENL IRVFQEGKDI HTQTASWMFG
ABi GK24      VAEAGWALVA LDYSQIELRV LAHLSGDENL IRVFQEGKDI HTQTASWMFG 651                                                          700
Tth HB8       VPPEAVDPLM RRAAKTVNFG VLYGMSAHRL SQELAIPYEE AVAFIERYFQ
Tth Z05       VSPEAVDPIM RRAAKTVNFG VLYGMSAHRL SQELAIPYEE AVAFIERYFQ
Tth GK24      VPPEAVDPLM RRAAKTVNFG VLYGMSAHRL SQELAIPYEE AVAFIERYFQ
ABi GK24      VPPEAVDPLM RRAAKTVNFG VLYGMSAHRL SQELAIPYEE AVAFIERYFQ 701                                                          750
Tth HB8       SFPKVRAWIE KTLEEGRKRG YVETLFGRPR YVPDLNARVK SVREAAERMA
Tth Z05       SFPKVRAWIE KTLEEGRKRG YVETLFGRRR YVPDLNARVK SVREAAERMA
Tth GK24      SFPKVRAWIE KTLEEGRKRG YVETLFGRRR YVPDLNARVK SVREAAERMA
ABi GK24      SFPKVRAWIE KTLEEGRKRG YVETLFGRRR YVPDLNARVK SVREAAERMA 751                                                          800
Tth HB8       FNMPVQGTAA DLMKLAMVKL FPRLREMGAR MLLQVHDELL LEAPQARAEE
Tth Z05       FNMPVQGTAA DLMKLAMVKL FPRLREMGAR MLLQVHDELL LEAPQARAEE
Tth GK24      FNMPVQGTAA DLMKLAMVKL FPRLREMGAR MLLQVHDELL LEAPQAGAEE
ABi GK24      FNMPVQGTAA DLMKLAMVKL FPRLREMGAR MLLQVHDELL LEAPQARAEE 801                                         834
Tth HB8       VAALAKEAME KAYPLAVPLE VEVGMGEDWL SAKG
Tth Z05       VAALAKEAME KAYPLAVPLE VEVGIGEDWL SAKG
Tth GK24      VAALAKEAME KAYPLAVPLE VEVGMGEDWL SAKG
ABi GK24      VAALAKEAME KAYPLAVPLE VEVGMGEDWL SAKG
```

FIGURE 2A

```
            1                                                           50
Tth HB8     MEAMLPLFEP KGRVLLVDGH HLAYRTFFAL KGLTTSRGEP VQAVYGFAKS
Tth Z05     MKAMLPLFEP KGRVLLVDGH HLAYRTFFAL KGLTTSRGEP VQAVYGFAKS
Tth GK24    MEAMLPLFEP KGRVLLVDGH HLAYRTFFAL KGLTTSRGEP VQAVYGFAKS
Tth RQ-1    MEAMLPLFEP KGRVLLVDGH HLAYRTFFAL KGLTTSRGEP VQAVYGFAKS 51                                                          100
Tth HB8     LLKALKEDGY KAVFVVFDAK APSFRHEAYE AYKAGRAPTP EDFPRQLALI
Tth Z05     LLKALKEDGY KAVFVVFDAK APSFRHEAYE AYKAGRAPTP EDFPRQLALI
Tth GK24    LLKALKEDGY KAVFVVFDAK APSFRHEAYE AYKAGRAPTP EDFPRQLALI
TTh RQ-1    LLKALKEDGY KAVFVVFDAK APSFRHEAYE AYKAGRAPTP EDFPRQLALI 101                                                         150
Tth HB8     KELVDLLGFT RLEVPGYEAD DVLATLAKKA EKEGYEVRIL TADRDLYQLV
Tth Z05     KELVDLLGFT RLEVPGFEAD DVLATLAKKA EREGYEVRIL TADRDLYQLV
Tth GK24    KELVDLLGFT RLEVPGYEAD DVLATLAKNP EKEGYEVRIL TADRDLDQLV
Tth RQ-1    KELVDLLGFT RLEVPGFEAD DVLATLAKKA EREGYEVRIL TADRDLYQLV 151                                                         200
Tth HB8     SDRVAVLHPE GHLITPEWLW EKYGLRPEQW VDFRALVGDP SDNLPGVKGI
Tth Z05     SDRVAVLHPE GHLITPEWLW EKYGLKPEQW VDFRALVGDP SDNLPGVKGI
Tth GK24    SDRVAVLHPE GHLITPEWLW QKYGLKPEQW VDFRALVGDP SDNLPGVKGI
Tth RQ-1    SDRVAVLHPE GHLITPEWLW EKYGLRPEQW VDFRALVGDP SDNLPGVKGI 201                                                         250
Tth HB8     GEKTALKLLK EWGSLENLLK NLDRVKPENV REKIKAHLED LRLSLELSRV
Tth Z05     GEKTALKLLK EWGSLENILK NLDRVKPESV RERIKAHLED LKLSLELSRV
Tth GK24    GEKTALKLLK EWGSLENLLK NLDRVKPENV REKIKAHLED LRLSLELSRV
Tth RQ-1    GEKTALKLLK EWGSLENLLK NLDRVKPESV REKIKAHLED LRLSLELSRV 251                                                         300
Tth HB8     RTDLPLEVDL AQGREPDREG LRAFLERLEF GSLLHEFGLL EAPAPLEEAP
Tth Z05     RSDLPLEVDF ARRREPDREG LRAFLERLEF GSLLHEFGLL EAPAPLEEAP
Tth GK24    RTDLPLEVDL AQGREPDREG LRAFLERLEF GSLLHEFGLL EAPAPLEEAP
Tth RQ-1    RTDLPLEVDL AQGREPDREG LRAFLERLEF GSLLHEFGLL EAPAPLEEAP 301                                                         350
Tth HB8     WPPPEGAFVG FVLSRPEPMW AELKALAACR DGRVHRAADP LAGLKDLKEV
Tth Z05     WPPPEGAFVG FVLSRPEPMW AELKALAACK EGRVHRAKDP LAGLKDLKEV
Tth GK24    WPPPEGAFVG FVLSRPEPMW AELKALAACR DGRVHRAADP LAGLKDLKEV
Tth RQ-1    WPPPEGAFVG FVLSRPEPMW AELKALAACR DGRVHRAEDP LAGLKDLKEV 351                                                         400
Tth HB8     RGLLAKDLAV LASREGLDLV PGDDPMLLAY LLDPSNTTPE GVARRYGGEW
Tth Z05     RGLLAKDLAV LALREGLDLA PSDDPMLLAY LLDPSNTTPE GVARRYGGEW
Tth GK24    RGLLAKDLAV LASREGLDLV PGDDPMLLAY LLDPSNTTPE GVARRYGGEW
Tth RQ-1    RGLLAKDLAV LASREGLDLV PGDDPMLLAY LLDPSNTTPE GVARRYGGEW 401                                                         450
Tth HB8     TEDAAHRALL SERLHRNLLK RLEGEEKLLW LYHEVEKPLS RVLAHMEATG
Tth Z05     TEDAAHRALL AERLQQNLLE RLKGEEKLLW LYQEVEKPLS RVLAHMEATG
Tth GK24    TEDAAHRALL SERLHRNLLK RLQGEEKLLW LYHEVEKPLS RVLAHMEATG
Tth RQ-1    TEDAAQRALL SERLQQNLLK RLQGEEKLLW LYHEVEKPLS RVLAHMEATG
```

FIGURE 2B

```
              451                                                       500
Tth HB8       VRLDVAYLQA LSLELAEEIR RLEEEVFRLA GHPFNLNSRD QLERVLFDEL
Tth Z05       VRLDVAYLKA LSLELAEEIR RLEEEVFRLA GHPFNLNSRD QLERVLFDEL
Tth GK24      VRLDVAYLQA LSLELAEEIR RLEEEVFRLA GHPFNLNSRD QLERVLFDEL
Tth RQ-1      VRLDVAYLQA LSLELAEEIR RLEEEVFRLA GHPFNLNSRD QLERVLFDEL 501                                                       550
Tth HB8       RLPALGKTQK TGKRSTSAAV LEALREAHPI VEKILQHREL TKLKNTYVDP
Tth Z05       RLPALGKTQK TGKRSTSAAV LEALREAHPI VEKILQHREL TKLKNTYVDP
Tth GK24      RLPALGKTQK TGKRSTSAAV LEALREAHPI VEKILQHREL TKLKNTYVDP
Tth RQ-1      RLPALGKTQK TGKRSTSAAV LEALREAHPI VEKILQHREL TKLKNTYVDP 551                                                       600
Tth HB8       LPSLVHPRTG RLHTRFNQTA TATGRLSSSD PNLQNIPVRT PLGQRIRRAF
Tth Z05       LPGLVHPRTG RLHTRFNQTA TATGRLSSSD PNLQNIPIRT PLGQRIRRAF
Tth GK24      LPSLVHPNTG RLHTRFNQTA TATGRLSSSD PNLQNIPVRT PLGQRIRRAF
Tth RQ-1      LPSLVHPRTG RLHTRFNQTA TATGRLSSSD PNLQNIPVRT PLGQRIRRAF 601                                                       650
Tth HB8       VAEAGWALVA LDYSQIELRV LAHLSGDENL IRVFQEGKDI HTQTASWMFG
Tth Z05       VAEAGWALVA LDYSQIELRV LAHLSGDENL IRVFQEGKDI HTQTASWMFG
Tth GK24      VAEAGWALVA LDYSQIELRV LAHLSGDENL IRVFQEGKDI HTQTASWMFG
Tth RQ-1      VAEAGWALVA LDYSQIELRV LAHLSGDENL IRVFQEGKDI HTQTASWMFG 651                                                       700
Tth HB8       VPPEAVDPLM RRAAKTVNFG VLYGMSAHRL SQELAIPYEE AVAFIERYFQ
Tth Z05       VSPEAVDPLM RRAAKTVNFG VLYGMSAHRL SQELAIPYEE AVAFIERYFQ
Tth GK24      VPPEAVDPLM RRAAKTVNFG VLYGMSAHRL SQELAIPYEE AVAFIERYFQ
Tth RQ-1      VPPEAVDPLM RRAAKTVNFG VLYGMSAHRL SQELSIPYEE AVAFIERYFQ 701                                                       750
Tth HB8       SFPKVRAWIE KTLEEGRKRG YVETLFGRRR YVPDLNARVK SVREAAERMA
Tth Z05       SFPKVRAWIE KTLEEGRKRG YVETLFGRRR YVPDLNARVK SVREAAERMA
Tth GK24      SFPKVRAWIE KTLEEGRKRG YVETLFGRRR YVPDLNARVK SVREAAERMA
AB1 Tth GK24  SFPKVRAWIE KTLEEGRKRG YVETLFGRRR YVPDLNARVK SVREAAERMA
Tth RQ-1      SFPKVRAWIE KTLEEGRKRG YVETLFGRRR YVPDLNARVK SVREAAERMA 751                                                       800
Tth HB8       FNMPVQGTAA DLMKLAMVKL FPRLREMGAR MLLQVHDELL LEAPQARAEE
Tth Z05       FNMPVQGTAA DLMKLAMVKL FPHLREMGAR MLLQVHDELL LEAPQARAEE
Tth GK24      FNMPVQGTAA DLMKLAMVKL FPRLREMGAR MLLQVHDELL LEAPQAGAEE
Tth RQ-1      FNMPVQGTAA DLMKLAMVKL FPRLREMGAR MLLQVHDELL LEAPQARAEE
```

FIGURE 2C

```
              801                                      834
Tth HB8       VAALAKEAME KAYPLAVPLE VEVGMGRDWL SAKG
Tth Z05       VAALAKEAME KAYPLAVPLE VEVGIGEDWL SAKG
Tth GK24      VAALAKEAME KAYPLAVPLE VEVGMGRDWL SAKG
Tth RQ-1      VAALAKEAME KAYPLAVPLE VEVGIGRDWL SAKG
```

FIGURE 3

```
1b21 :   1 MEAMLPLFEPKGRVLLVDGHHLAYRTFFALKGLTTSRGEPVQAVYGFAKSLLKALKEDGY  60
HB8  :   1 MEAMLPLFEPKGRVLLVDGHHLAYRTFFALKGLTTSRGEPVQAVYGFAKSLLKALKEDGY  60

1b21 :  61 KAVFVVFDAKAPSFRHEAYEAYKAGRAPTPEDFPRQLALIKELVDLLGFTRLEVPGYEAD 120
HB8  :  61 KAVFVVFDAKAPSFRHEAYEAYKAGRAPTPEDFPRQLALIKELVDLLGFTRLEVPGYEAD 120

1b21 : 121 DVLATLAKKAEKEGYEVRILTADRDLYQLVSDRVAVLHPEGHLITPEWLWEKYGLKPEQW 180
HB8  : 121 DVLATLAKKAEKEGYEVRILTADRDLYQLVSDRVAVLHPEGHLITPEWLWEKYGLRPEQW 180

1b21 : 181 VDFRALVGDPSDNLPGVKGIGEKTALKLLKEWGSLENLLKNLDRVKPENVREKIKAHLED 240
HB8  : 181 VDFRALVGDPSDNLPGVKGIGEKTALKLLKEWGSLENLLKNLDRVKPENVREKIKAHLED 240

1b21 : 241 LRLSLELSRVRTDLPLEVDLAQGREPDREGLRAFLERLEFGSLLHEFGLLEAPAPLEEAP 300
HB8  : 241 LRLSLELSRVRTDLPLEVDLAQGREPDREGLRAFLERLEFGSLLHEFGLLEAPAPLEEAP 300

1b21 : 301 WPPPEGAFVGFVLSRPEPMWAELKALAACRDGRVHRAADPLAGLKDLKEVRGLLAKDLAV 360
HB8  : 301 WPPPEGAFVGFVLSRPEPMWAELKALAACRDGRVHRAADPLAGLKDLKEVRGLLAKDLAV 360

1b21 : 361 LASREGLDLVPGDDPMLLAYLLDPSNTTPEGVARRYGGEWTEDAAHRALLSERLHRNLLK 420
HB8  : 361 LASREGLDLVPGDDPMLLAYLLDPSNTTPEGVARRYGGEWTEDAAHRALLSERLHRNLLK 420

1b21 : 421 RLEGEEKLLWLYHEVEKPLSRVLAHMEATGVRLDVAYLQALSLELAEEIRRLEEEVFRLA 480
HB8  : 421 RLEGEEKLLWLYHEVEKPLSRVLAHMEATGVRLDVAYLQALSLELAEEIRRLEEEVFRLA 480

1b21 : 481 GHPFNLNSRDQLERVLFDELRLPALGKTQKTGKRSTSAAVLEALREAHPIVEKILQHREL 540
HB8  : 481 GHPFNLNSRDQLERVLFDELRLPALGKTQKTGKRSTSAAVLEALREAHPIVEKILQHREL 540

1b21 : 541 TKLKNTYVDPLPSLVHPRTGRLHTRFNQTATATGRLSSSDPNLQNIPVRTPLGQRIRRAF 600
HB8  : 541 TKLKNTYVDPLPSLVHPRTGRLHTRFNQTATATGRLSSSDPNLQNIPVRTPLGQRIRRAF 600

1b21 : 601 VAEAGWALVALDYSQIELRVLAHLSGDENLIRVFQEGKDIHTQTASWMFGVPPEAVDPLM 660
HB8  : 601 VAEAGWALVALDYSQIELRVLAHLSGDENLIRVFQEGKDIHTQTASWMFGVPPEAVDPLM 660

1b21 : 661 RRAAKTVNFGVLYGMSAHRLSQELAIPYEEAVAFIERYFQSFPKVRAWIEKTLEEGRKRG 720
HB8  : 661 RRAAKTVNFGVLYGMSAHRLSQELAIPYEEAVAFIERYFQSFPKVRAWIEKTLEEGRKRG 720

1b21 : 721 YVETLFGRRRYVPDLNARVKSVREAAERMAFNMPVQGTAADIMKLAMVKLFPRLREMGAR 780
HB8  : 721 YVETLFGRRRYVPDLNARVKSVREAAERMAFNMPVQGTAADIMKLAMVKLFPRLREMGAR 780

1b21 : 781 MLLQVHDELLLEAPQARAEEVAALAKEAMEKAYPLAVPLEVEVGMGEDWLSAKG 834
HB8  : 781 MLLQVHDELLLEAPQARAEEVAALAKEAMEKAYPLAVPLEVEVGMGEDWLSAKG 834
```

SEQUENCE LISTING

<160> NUMBER OF SEQ ID NOS: 31

<210> SEQ ID NO 1
<211> LENGTH: 2505
<212> TYPE: DNA
<213> ORGANISM: Thermus thermophilus

<400> SEQUENCE: 1

| | | | | | |
|---|---|---|---|---|---|
| atggaggcga | tgcttccgct | ctttgaaccc | aaaggccggg | tcctcctggt ggacggccac | 60 |
| cacctggcct | accgcacctt | cttcgccctg | aagggcctca | ccacgagccg gggcgaaccg | 120 |
| gtgcaggcgg | tctacggctt | cgccaagagc | ctcctcaagg | ccctgaagga ggacgggtac | 180 |
| aaggccgtct | tcgtggtctt | tgacgccaag | gcccccctcct | tccgccacga ggcctacgag | 240 |
| gcctacaagg | cggggagggc | cccgaccccc | gaggacttcc | cccggcagct cgccctcatc | 300 |
| aaggagctgt | ggaccctcct | ggggtttacc | cgcctcgagg | tccccggcta cgaggcggac | 360 |
| gacgtcctcg | ccaccctggc | caagaaggcg | aaaaggagg | gtacgaggt gcgcatcctc | 420 |
| accgccgacc | gcgacctcta | ccaactcgtc | tccgaccgcg | tcgccgtcct ccaccccgag | 480 |
| ggccacctca | tcaccccgga | gtggctttgg | cagaagtacg | gcctcaagcc ggagcagtgg | 540 |
| gtggacttcc | gcgccctcgt | gggggacccc | tccgacaacc | tccccggggt caagggcatc | 600 |
| ggggagaaga | ccgccctcaa | gctcctcaag | gagtggggaa | gcctggaaaa cctcctcaag | 660 |
| aacctggacc | gggtaaagcc | agaaaacgtc | cgggagaaga | tcaaggccca cctgaagac | 720 |
| ctcaggcttt | ccttggagct | ctcccggtg | cgcaccgacc | tcccctgga ggtggacctc | 780 |
| gcccaggggc | gggagcccga | ccgggagggg | cttagggcct | tcctggagag gctggagttc | 840 |
| ggcagcctcc | tccacgagtt | cggcctcctg | gaggcccccg | cccccctgga ggaggccccc | 900 |
| tggccccgc | cggaagggc | cttcgtgggc | ttcgtcctct | cccgcccga gcccatgtgg | 960 |
| gcggagctta | agccctggc | cgcctgcagg | acggccgggt | gcaccgggc agcggacccc | 1020 |
| ttggcggggc | taaaggacct | caaggaggtc | cggggcctcc | tcgccaagga cctcgccgtc | 1080 |
| ttggcctcga | ggggagggct | agacctcgtg | cccggggacg | accccatgct cctcgcctac | 1140 |
| ctcctggacc | cctccaacac | caccccgag | ggggtggcgc | ggcgctacgg ggggagtgg | 1200 |
| acggaggacg | ccgccaccg | ggccctcctc | tcggagaggc | tccatcggaa cctccttaag | 1260 |
| cgcctccagg | gggaggagaa | gctccttttgg | ctctaccacg | aggtggaaaa gccccctctcc | 1320 |
| cgggtcctgg | cccacatgga | ggccaccggg | gtacggctgg | acgtggccta cctgcaggcc | 1380 |
| cttttccctgg | agcttgcgga | ggagatccgc | cgcctcgagg | aggaggtctt ccgcttggcg | 1440 |
| ggccaccccct | tcaacctcaa | ctccgggac | cagctggaga | gggtgctctt tgacgagctt | 1500 |
| aggcttcccg | ccttggggaa | gacgcaaaag | acgggcaagc | gctccaccag cgccgcggtg | 1560 |
| ctggaggccc | tacggaggc | ccaccccatc | gtggagaaga | tcctccagca ccgggagctc | 1620 |
| accaagctca | gaacaccta | cgtggacccc | ctcccaagcc | tcgtccaccc gaatacgggc | 1680 |
| cgcctccaca | cccgcttcaa | ccagacggcc | acggccacgg | gaggcttag tagctccgac | 1740 |
| cccaacctgc | agaacatccc | cgtccgcacc | cccttgggcc | agaggatccg ccgggccttc | 1800 |
| gtggccgagc | cgggttgggc | gttggtggcc | ctggactata | gccagataga gctccgcgtc | 1860 |
| ctcgcccacc | tctccgggga | cgagaacctg | atcagggtct | tccaggaggg gaaggacatc | 1920 |
| cacacccaga | ccgcaagctg | gatgttcggc | gtccccccgg | aggccgtgga tccctgatg | 1980 |
| cgccgggcgg | ccaagacggt | gaacttcggc | gtcctctacg | gcatgtccgc ccataggctc | 2040 |

```
tcccaggagc ttgccatccc ctacgaggag gcggtggcct ttatagagcg ctacttccaa    2100
agcttcccca aggtgcgggc ctggatagaa aagaccctgg aggaggggag gaagcggggc    2160
tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
gacctcatga agctcgccat ggtgaagctc ttccccgcc tccgggagat ggggccccgc     2340
atgctcctcc aggtccacga cgagctcctc ctggaggccc ccaagcgcg gccgaggag     2400 gtggcggctt tggccaagga ggccatggag aaggcctatc ccctcgccgt gccctggag    2460 gtggaggtgg ggatggggga ggactggctt tccgccaagg gttag                   2505

<210> SEQ ID NO 2
<211> LENGTH: 2505
<212> TYPE: DNA
<213> ORGANISM: Thermus thermophilus

<400> SEQUENCE: 2
atggaggcga tgcttccgct cttttgaaccc aaaggccggg tcctcctggt ggacggccac     60
cacctggcct accgcacctt cttcgccctg aagggcctca ccacgagccg gggcgaaccg    120
gtgcaggcgg tctacggctt cgccaagagc ctcctcaagg ccctgaagga ggacgggtac    180
aaggccgtct tcgtggtctt tgacgccaag gccccctcct tccgccacga ggcctacgag    240
gcctacaagg cggggagggc cccgaccccc gaggacttcc ccggcagct cgccctcatc     300 aaggagctgg tggacctctt ggggtttact cgcctcgagg tcccgggctt tgaggcggac    360
gacgtcctcg ccaccctggc caagaaggcg aaaaagaag ggtacgaggt gcgcatcctc     420
accgccgacc gggaccctcta ccagctcgtc tccgaccggg tcgccgtcct ccaccccgag    480
ggccacctca tcaccccgga gtggcttttgg gagaagtacg gcctcaggcc ggagcagtgg    540
gtggacttcc gcgccctcgt aggggacccc tccgacaacc tccccggggt caagggcatc    600
ggggagaaga ccgccctcaa gctccttaag gagtggggaa gcctggaaaa cctcctcaag    660
aacctggacc gggtgaagcc ggaaagcgtc cgggagaaga tcaaggccca cctggaagac    720
ctcaggctct ccttggagct ctcccggtg cgcaccgacc tccccctgga ggtggacctc    780
gcccaggggc gggagcccga ccgggaaggg cttagggcct tcctggagag gctagagttc    840
ggcagcctcc tccacgagtt cggcctcctg gaggcccccg cccccctgga ggaggccccc    900 tggccccgc cggaaggggc cttcgtgggc ttcgtcctct cccgccccga gccatgtgg     960 gcggagctta agccctggc cgcctgcagg acggccggg tgcaccgggc ggaggacccc    1020
ttggcggggc ttaaggacct caaggaggtc cggggcctcc tcgccaagga cctcgccgtt    1080
ttggcctcga ggggaggggct agacctcgtg cccggggacg accccatgct cctcgcctac    1140
ctcctggacc cctccaacac caccccgag ggggtggcgc ggcgctacgg gggggagtgg    1200
acggaggacg ccgcccagcg ggccctcctc tcggagaggc tccagcagaa cctccttaag    1260
cgcctccagg gggaggagaa gctcctctgg ctctaccacg aggtggaaaa gccccctctcc    1320 cgggtcctgg cccacatgga ggccaccggg gtacggctgg acgtgcccta ccttcaggcc    1380
ctttccctgg agcttgcgga ggagatccgc cgcctcgagg aggaggtctt ccgcttggcg    1440 ggccaccccct tcaacctcaa ctcccgggac cagctgaaaa gggtgctctt tgacgagctt    1500
aggcttcccg ccttggggaa gacgcaaaag acgggcaagc gctccaccag cgccgcggtg    1560
ctggaggccc tacgggaggc ccaccccatc gtggagaaga tcctccagca ccgggagctc    1620
accaagctca agaacaccta cgtggacccc ctcccaagcc tcgtccaccc gaggacgggc    1680
```

-continued

| | |
|---|---|
| cgcctccaca cccgcttcaa ccagacggcc acggccacgg ggaggcttag tagctccgac | 1740 |
| cccaacctgc agaacatccc cgtccgcacc cccttgggcc agaggatccg ccgggccttc | 1800 |
| gtagccgagg cgggatgggc gttggtggcc ctggactata gccagataga gctccgcgtc | 1860 |
| ctcgccacc tctccgggga cgagaacctg atcagggtct tccaggaggg aaggacatc | 1920 |
| cacacccaga ccgcaagctg gatgttcggt gtccccccgg aggccgtgga cccctgatg | 1980 |
| cgccgggcgg ccaagacggt gaacttcggc gtcctctacg gcatgtccgc ccaccggctc | 2040 |
| tcccaggagc tttccatccc ctacgaggag gcggtggcct ttatagagcg ctacttccaa | 2100 |
| agcttcccca aggtgcgggc ctggatagaa aagaccctgg aggaggggag aagcggggc | 2160 |
| tacgtggaaa ccctcttcgg aagaaggcgc tacgtgcccg acctcaacgc ccgggtgaag | 2220 |
| agcgtcaggg aggccgcgga gcgcatggcc ttcaacatgc ccgtccaggg caccgccgcc | 2280 |
| gacctcatga agctcgccat ggtgaagctc ttccccccgcc tccgggagat gggggcccgc | 2340 |
| atgctcctcc aggtccacga cgagctcctc ctggaggccc ccaagcgcg ggccgaggag | 2400 |
| gtggcggctt tggccaagga ggccatggag aaggcctatc ccctcgccgt acccctggag | 2460 |
| gtggaggtgg ggatcgggga ggactggctt tccgccaagg gctag | 2505 |

<210> SEQ ID NO 3
<211> LENGTH: 2505
<212> TYPE: DNA
<213> ORGANISM: Thermus thermophilus

<400> SEQUENCE: 3

| | |
|---|---|
| atggaggcga tgcttccgct ctttgaaccc aaaggccggg tcctcctggt ggacggccac | 60 |
| cacctggcct accgcacctt cttcgccctg aagggcctca ccacgagccg ggcgaaccg | 120 |
| gtgcaggcgg tctacggctt cgccaagagc ctcctcaagg ccctgaagga ggacgggtac | 180 |
| aaggccgtct tcgtggtctt tgacgccaag gcccctcct tccgccacga ggcctacgag | 240 |
| gcctacaagg cggggagggc cccgaccccc gaggacttcc ccggcagct cgccctcatc | 300 |
| aaggagctgg tggacctcct ggggtttacc cgcctcgagg tccccggcta cgaggcggac | 360 |
| gacgtcctcg ccaccctggc caagaaggcg gaaaaggagg ggtacgaggt gcgcatcctc | 420 |
| accgccgacc gcgacctcta ccaactcgtc tccgaccgcg tcgccgtcct ccaccccgag | 480 |
| ggccacctca tcaccccgga gtggctttgg gagaagtacg gcctcaagcc ggagcagtgg | 540 |
| gtggacttcc gcgccctcgt gggggacccc tccgacaacc tccccgggt caagggcatc | 600 |
| ggggagaaga ccgcctcaa gctcctcaag gagtggggaa gctggaaaa cctcctcaag | 660 |
| aacctggacc gggtaaagcc agaaaacgtc cgggagaaga tcaaggccca cctggaagac | 720 |
| ctcaggcttt ccttggagct ctcccgggtg cgcaccgacc tccccctgga ggtgaccctc | 780 |
| gcccagggc gggagcccga ccgggagggg cttagggcct tcctggagag gctggagttc | 840 |
| ggcagcctcc tccacgagtt cggcctcctg gaggcccccg ccccctgga ggaggccccc | 900 |
| tggccccgc cggaagggc cttcgtgggc ttcgtcctct cccgccccga gccatgtgg | 960 |
| gcggagctta agcccctggc cgcctgcagg acggccggg tgcaccgggc agcagacccc | 1020 |
| ttggcggggc taaaggacct caaggaggtc cggggcctcc tcgccaagga cctcgccgtc | 1080 |
| ttggcctcga gggaggggct agacctcgtg cccggggacg accccatgct cctcgcctac | 1140 |
| ctcctggacc cctccaacac caccccgag ggggtggcgc ggcgctacgg gggggagtgg | 1200 |
| acggaggacg ccgcccaccg ggccctcctc tcggagaggc tccatcggaa cctccttaag | 1260 |
| cgcctcgagg gggaggagaa gctccttgg ctctaccacg aggtggaaaa gcccctctcc | 1320 |

-continued

| | |
|---|---|
| cgggtcctgg cccacatgga ggccaccggg gtacggctgg acgtggccta ccttcaggcc | 1380 |
| cttttccctg agcttgcgga ggagatccgc cgcctcgagg aggaggtctt ccgcttggcg | 1440 |
| ggccacccct tcaacctcaa ctcccgggac cagctggaaa gggtgctctt tgacgagctt | 1500 |
| aggcttcccg ccttggggaa gacgcaaaag acgggcaagc gctccaccag cgccgcggtg | 1560 |
| ctggaggccc tacgggaggc ccaccccatc gtggagaaga tcctccagca ccgggagctc | 1620 |
| accaagctca gaacaccta cgtggacccc ctcccaagcc tcgtccaccc gaggacgggc | 1680 |
| cgcctccaca cccgcttcaa ccagacggcc acggccacgg ggaggcttag tagctccgac | 1740 |
| cccaacctgc agaacatccc cgtccgcacc cccttgggcc agaggatccg ccgggccttc | 1800 |
| gtggccgagg cgggatgggc gttggtggcc ctggactata gccagataga gctccgcgtc | 1860 |
| ctcgccacc tctccgggga cgagaacctg atcagggtct tccaggaggg gaaggacatc | 1920 |
| cacacccaga ccgcaagctg gatgttcggc gtccccccgg aggccgtgga cccctgatg | 1980 |
| cgccgggcgg ccaagacggt gaacttcggc gtcctctacg gcatgtccgc ccataggctc | 2040 |
| tcccaggagc ttgccatccc ctacgaggag gcggtggcct ttatagagcg ctacttccaa | 2100 |
| agcttcccca aggtgcgggc ctggatagaa aagaccctgg aggaggggag aaagcggggc | 2160 |
| tacgtggaaa ccctcttcgg aagaaggcgc tacgtgcccg acctcaacgc ccgggtgaag | 2220 |
| agcgtcaggg aggccgcgga gcgcatggcc ttcaacatgc ccgtccaggg caccgccgcc | 2280 |
| gacctcatga agctcgccat ggtgaagctc ttccccgcc tccgggagat gggggcccgc | 2340 |
| atgctcctcc aggtccacga cgagctcctc ctggaggccc ccaagcgcg ggccgaggag | 2400 |
| gtggcggctt tggccaagga ggccatggag aaggcctatc ccctcgccgt gccccctggag | 2460 |
| gtggaggtgg ggatgggga ggactggctt ccgccaagg gttag | 2505 |

<210> SEQ ID NO 4
<211> LENGTH: 2505
<212> TYPE: DNA
<213> ORGANISM: Thermus thermophilus

<400> SEQUENCE: 4

| | |
|---|---|
| atggaggcga tgcttccgct ctttgaaccc aaaggccggg tcctcctggt ggacggccac | 60 |
| cacctggcct accgcacctt cttcgccctg aagggcctca ccacgagccg ggcgaaccg | 120 |
| gtgcaggcgg tctacgactt cgccaagagc ctcctcaagg ccctgaagga ggacgggtac | 180 |
| aaggccgtct tcgtggtctt tgacgccaag gcccctcct tccgccacga ggcctacgag | 240 |
| gcctacaagg cggggagggc cccgaccccc gaggacttcc ccggcagct cgccctcatc | 300 |
| aaggagctgg tggacctcct ggggtttacc cgcctcgagg tccccggcta cgaggcggac | 360 |
| gacgtcctcg ccaccctggc caagaaggcg gaaaaggagg gtacgaggt gcgcatcctc | 420 |
| accgccgacc gcgacctcta ccaactcgtc tccgaccgcg tcgccgtcct ccaccccgag | 480 |
| ggccaccta tcaccccgga gtggctttgg cagaagtacg gcctcaagcc ggagcagtgg | 540 |
| gtggacttcc gcgccctcgt gggggacccc tccgacaacc tccccgggt caagggcatc | 600 |
| ggggagaaga ccgcctcaa gctcctcaag gagtggggaa gcctggaaaa cctcctcaag | 660 |
| aacctggacc gggtaaagcc agaaaacgtc cgggagaaga tcaaggccca cctggaagac | 720 |
| ctcaggcttt ccttggagct ctcccggtg cgcaccgacc tccccctgga ggtgaccctc | 780 |
| gcccaggggc gggagcccga ccgggagggg cttagggcct tcctggagag gctggagttc | 840 |
| ggcagcctcc tccacgagtt cggctcctg gaggcccccg ccccctgga ggaggccccc | 900 |
| tggccccgc cggaagggc cttcgtgggc ttcgtcctct cccgcccga gcccatgtgg | 960 |

```
gcggagctta aagccctggc cgcctgcagg gacggccggg tgcaccgggc agcggacccc    1020
ttggcggggc taaaggacct caaggaggtc cggggcctcc tcgccaagga cctcgccgtc    1080
ttggcctcga gggaggggct agacctcgtg cccggggacg accccatgct cctcgcctac    1140
ctcctggacc cctccaacac caccccggag ggggtggcgc ggcgctacgg ggggagtgg     1200 acggaggacg ccgcccaccg ggccctcctc tcggagaggc tccatcggaa cctccttaag    1260
cgcctccagg gggaggagaa gctcctttgg ctctaccacg aggtggaaaa gcccctctcc    1320
cgggtcctgg cccacatgga ggccaccggg gtacggctgg acgtggccta cctgcaggcc    1380 cttttccctgg agcttgcgga ggagatccgc cgcctcgagg aggaggtctt ccgcttggcg    1440
ggccacccct tcaacctcaa ctcccgggac cagctggaga gggtgctctt tgacgagctt    1500
aggcttcccg ccttggggaa gacgcaaaag acgggcaagc gctccaccag cgccgcggtg    1560
ctggaggccc tacgggaggc ccaccccatc gtggagaaga tcctccagca ccgggagctc    1620
accaagctca gaacacccta cgtggacccc ctcccaagcc tcgtccaccc gaatacgggc    1680
cgcctccaca cccgcttcaa ccagacggcc acggccacgg ggaggcttag tagctccgac    1740
cccaacctgc agaacatccc cgtccgcacc ccctttgggcc agaggatccg ccgggccttc    1800
gtggccgagg cgggttgggc gttggtggcc ctggactata gccagataga gctccgcgtc    1860 ctcgccacc tctccgggga cgagaacctg atcagggtct tccaggaggg gaaggacatc    1920
cacacccaga ccgcaagctg gatgttcggc gtccccccgg aggccgtgga tcccctgatg    1980
cgccgggcgg ccaagacggt gaacttcggc gtcctctacg gcatgtccgc ccataggctc    2040
tcccaggagc ttgccatccc ctacgaggag gcggtggcct ttatagagcg ctacttccaa    2100
agcttcccca aggtgcgggc ctggatagaa aagaccctgg aggagggag gaagcggggc    2160 tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
gacctcatga agctcgccat ggtgaagctc ttcccccgcc tccgggagat ggggggcccgc    2340 atgctcctcc aggtccacga cgagctcctc ctggaggccc ccaagcgcg gggccgaggag    2400 gtggcggctt tggccaagga ggccatggag aaggcctatc ccctcgccgt gccctggag    2460 gtggaggtgg ggatggggga ggactggctt ccgccaaggg gttag                    2505
```

<210> SEQ ID NO 5
<211> LENGTH: 2505
<212> TYPE: DNA
<213> ORGANISM: Thermus thermophilus

<400> SEQUENCE: 5

```
atggaggcga tgcttccgct ctttgaaccc aaaggccggg tcctcctggt ggacggccac      60
cacctggcct accgcacctt cttcgccctg aagggcctca ccacgagccg ggcgaaccg      120 gtgcaggcgg tctacgactt cgccaagagc ctcctcaagg ccctgaagga ggacgggtac     180
aaggccgtct tcgtggtctt tgacgccaag gcccctcct ccgccacga ggcctacgag       240 gcctacaagg cggggagggc cccgacccc gaggacttcc ccggcagct cgccctcatc        300 aaggagctgg tggacctctt gggggtttact cgcctcgagg tcccgggctt tgaggcggac     360
gacgtcctcg ccaccctggc caagaaggcg gaaaagaag gtacgaggt gcgcatcctc       420 accgccgacc gggacctcta ccagctcgtc tccgaccggg tcgccgtcct ccaccccgag     480
ggccacctca tcacccggga gtggctttgg gagaagtacg gcctcaggcc ggagcagtgg     540
gtggacttcc gcgccctcgt agggaccccc tccgacaacc tccccgggt caagggcatc    600
```

```
ggggagaaga ccgccctcaa gctccttaag gagtggggaa gcctggaaaa cctcctcaag    660
aacctggacc gggtgaagcc ggaaagcgtc cgggagaaga tcaaggccca cctggaagac    720
ctcaggctct ccttggagct ctcccgggtg cgcaccgacc tcccgctgga ggtggacctc    780
gcccagggc gggagcccga ccgggaaggg cttaggcct tcctggagag ctagagttc    840
ggcagcctcc tccacgagtt cggcctcctg gaggccccg ccccctgga ggaggccccc    900
tggcccccgc cggaagggc cttcgtgggc ttcgtcctct cccgccccga gcccatgtgg    960
gcggagctta agccctggc cgcctgcagg gacggccggg tgcaccgggc ggaggacccc   1020
ttggcggggc ttaaggacct caaggaggtc cggggcctcc tcgccaagga cctcgccgtt   1080
ttggcctcga gggaggggct agacctcgtg cccggggacg accccatgct cctcgcctac   1140
ctcctggacc cctccaacac caccccgag ggggtggcgc ggcgctacgg ggggagtgg   1200
acggaggacg ccgcccagcg ggccctcctc tcggagaggc tccagcagaa cctccttaag   1260
cgcctccagg gggaggagaa gctcctctgg ctctaccacg aggtggaaaa gccctctcc   1320
cgggtcctgg cccacatgga ggccaccggg gtacggctgg acgtggccta ccttcaggcc   1380
ctttccctgg agcttgcgga ggagatccgc cgcctcgagg aggaggtctt ccgcttggcg   1440
ggccacccct tcaacctcaa ctcccgggac cagctggaaa gggtgctctt tgacgagctt   1500
aggcttcccg ccttggggaa gacgcaaaag acgggcaagc gctccaccag cgccgcggtg   1560
ctggaggccc tacggaggc ccaccccatc gtggagaaga tcctccagca ccgggagctc   1620
accaagctca gaacaccta cgtggacccc ctcccaagcc tcgtccaccc gaggacgggc   1680
cgcctccaca cccgcttcaa ccagacggcc acggccacgg ggaggcttag tagctccgac   1740
cccaacctgc agaacatccc cgtccgcacc ccctggggcc agaggatccg ccgggccttc   1800
gtagccgagg cgggatgggc gttggtggcc ctggactata gccagataga gctccgcgtc   1860
ctcgccacc tctccgggga cgagaacctg atcagggtct ccaggagggg aaggacatc   1920
cacaccagag ccgcaagctg gatgttcggt gtccccccgg aggccgtgga ccccctgatg   1980
cgccgggcgg ccaagacggt gaacttcggc gtcctctacg gcatgtccgc ccaccggctc   2040
tcccaggagc tttccatccc ctacgaggag gcggtggcct ttatagagcg ctacttccaa   2100
agcttcccca aggtgcgggc ctggatagaa aagaccctgg aggaggggag gaagcggggc   2160
tacgtggaaa ccctcttcgg aagaaggcgc tacgtgcccg acctcaacgc ccgggtgaag   2220
agcgtcaggg aggccgcgga gcgcatggcc ttcaacatgc ccgtccaggg caccgccgcc   2280
gacctcatga agctcgccat ggtgaagctc ttccccgcc tccgggagat ggggccccgc   2340
atgctcctcc aggtccacga cgagctcctc ctggaggccc ccaagcgcg gccgaggag   2400
gtggcggctt tggccaagga ggccatggag aaggcctatc ccctcgccgt accctggag   2460
gtggaggtgg ggatcgggga ggactggctt tccgccaagg gctag                  2505
```

<210> SEQ ID NO 6
<211> LENGTH: 2505
<212> TYPE: DNA
<213> ORGANISM: Thermus thermophilus

<400> SEQUENCE: 6

```
atggaggcga tgcttccgct cttgaaccc aaaggccggg tcctcctggt ggacggccac     60
cacctggcct accgcacctt cttcgccctg aagggcctca ccacgagccg gggcgaaccg    120
gtgcaggcgg tctacgactt cgccaagagc ctcctcaagg ccctgaagga ggacgggtac    180
aaggccgtct tcgtggtctt tgacgccaag gcccctcct tccgccacga ggcctacgag    240
```

```
gcctacaagg cggggagggc cccgacccccc gaggacttcc cccggcagct cgccctcatc    300
aaggagctgg tggacctcct gggggtttacc cgcctcgagg tccccggcta cgaggcggac    360
gacgtcctcg ccaccctggc caagaaggcg gaaaaggagg ggtacgaggt gcgcatcctc    420
accgccgacc gcgacctcta ccaactcgtc tccgaccgcg tcgccgtcct ccaccccgag    480
ggccacctca tcaccccgga gtggctttgg gagaagtacg gcctcaagcc ggagcagtgg    540
gtggacttcc gcgccctcgt gggggacccc tccgacaacc tccccggggt caagggcatc    600
ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggcttt ccttggagct ctcccgggtg cgcaccgacc tccccctgga ggtggacctc    780 gcccagggge gggagcccga ccggggagggg cttaggggcct tcctggagag gctggagttc    840
ggcagcctcc tccacgagtt cggcctcctg gaggcccccg ccccctgga ggaggccccc    900 tggcccccgc cggaagggge cttcgtgggc ttcgtcctct cccgccccga gcccatgtgg    960
gcggagctta aagccctggc cgcctgcagg gacgccgggg tgcaccgggc agcagacccc   1020
ttggcggggc taaaggacct caaggaggtc cggggcctcc tcgccaagga cctcgccgtc   1080
ttggcctcga gggagggggct agacctcgtg cccggggacg accccatgct cctcgcctac   1140
ctcctggacc cctccaacac cacccccgag ggggtggcgc ggcgctacgg ggggagtgg   1200 acggaggacg ccgcccaccg ggccctcctc tcggagaggc tccatcggaa cctccttaag   1260
cgcctcgagg gggaggagaa gctcctttgg ctctaccacg aggtggaaaa gcccctctcc   1320
cgggtcctgg cccacatgga ggccaccggg gtacggctgg acgtggccta ccttcaggcc   1380
ctttccctgg agcttgcgga ggagatccgc cgcctcgagg aggaggtctt ccgcttggcg   1440
ggccacccct tcaacctcaa ctcccgggac cagctggaaa gggtgctctt tgacgagctt   1500
aggcttcccg ccttggggaa gacgcaaaag acgggcaagc gctccaccag cgccgcggtg   1560
ctggaggccc tacgggaggc ccaccccatc gtggagaaga tcctcagca ccgggagctc   1620 accaagctca gaacaccta cgtggacccc ctcccaagcc tcgtccaccc gaggacgggc   1680
cgcctccaca cccgcttcaa ccagacggcc acggccacgg ggaggcttag tagctccgac   1740
cccaacctgc agaacatccc cgtccgcacc cccttgggcc agaggatccg ccgggccttc   1800
gtggccgagg cggatgggc gttggtggcc ctggactata gccagataga gctccgcgtc   1860
ctcgcccacc tctccgggga cgagaacctg atcagggtct tccaggaggg gaaggacatc   1920
cacacccaga ccgcaagctg gatgttcggc gtcccccgg aggccgtgga ccccctgatg   1980
cgccgggcgg ccaagacggt gaacttcggc gtcctctacg gcatgtccgc ccataggctc   2040
tcccaggagc ttgccatccc ctacgaggag gcggtggcct ttatagagcg ctacttccaa   2100
agcttcccca aggtgcgggc ctggatagaa aagaccctgg aggaggggag aaagcggggc   2160
tacgtggaaa ccctcttcgg aagaaggcgc tacgtgcccg acctcaacgc ccgggtgaag   2220
agcgtcaggg aggccgcgga gcgcatggcc ttcaacatgc ccgtccaggg caccgccgcc   2280
gacctcatga gctcgccat ggtgaagctc ttccccgcc tccgggagat gggggcccgc   2340
atgctcctcc aggtccacga cgagctcctc ctggaggccc ccaagcgcg ggccgaggag   2400 gtggcggctt tggccaagga ggccatggag aaggcctatc ccctgccgt gcccctggag   2460 gtggaggtgg ggatggggga ggactggctt tccgccaagg gttag                    2505

<210> SEQ ID NO 7
<211> LENGTH: 2505
<212> TYPE: DNA
```

<213> ORGANISM: Thermus thermophilus

<400> SEQUENCE: 7

```
atggaggcga tgcttccgct ctttgaaccc aaaggccggg tcctcctggt ggacggccac      60
cacctggcct accgcacctt cttcgccctg aagggcctca ccacgagccg gggcgaaccg     120
gtgcaggcgg tctacggctt cgccaagagc ctcctcaagg ccctgaagga ggacgggtac     180
aaggccgtct tcgtggtctt tgacgccaag gcccccctcct tccgccacga ggcctacgag     240
gcctacaagg cggggagggc cccgaccccc gaggacttcc cccggcagct cgccctcatc     300
aaggagctgg tggacctcct ggggtttacc cgcctcgagg tccccggcta cgaggcggac     360
gacgtcctcg ccaccctggc caagaaggcg aaaaggagg ggtacgaggt gcgcatcctc      420
accgccgacc gcgacctcta ccaactcgtc tccgaccgcg tcgccgtcct ccaccccgag     480
ggccacctca tcaccccgga gtggcttttgg cagaagtacg gcctcaagcc ggagcagtgg     540
gtggacttcc gcgccctcgt gggggacccc tccgacaacc tccccggggt caagggcatc     600
ggggagaaga ccgccctcaa gctcctcaag gagtggggaa gcctggaaaa cctcctcaag     660
aacctggacc gggtaaagcc agaaaacgtc cgggagaaga tcaaggccca cctgaagac      720
ctcaggcttt ccttggagct ctcccggggtg cgcaccgacc tcccctgga ggtggacctc      780
gcccaggggc gggagcccga ccgggagggg cttaggggcct tcctggagag gctggagttc     840
ggcagcctcc tccacgagtt cggcctcctg gaggcccccg ccccctgga ggaggccccc     900
tggcccccgc cggaagggc cttcgtgggc ttcgtcctct cccgcccga gcccatgtgg     960
gcggagctta agccctggc cgcctgcagg gacggccggg tgcaccgggc agcggacccc    1020
ttggcgggc taaaggacct caaggaggtc cggggcctcc tcgccaagga cctcgccgtc    1080
ttggcctcga gggaggggct agacctcgtg cccggggacg accccatgct cctcgcctac    1140
ctcctggacc cctccaacac cacccccgag ggggtggcgc ggcgctacgg ggggagtgg    1200
acggaggacg ccgccaccg ggccctcctc tcggagaggc tccatcggaa cctccttaag    1260
cgcctccagg gggaggagaa gctccttttgg ctctaccacg aggtggaaaa gccctctcc    1320
cgggtcctgg cccacatgga ggccaccggg gtacggctgg acgtggccta cctgcaggcc    1380
ctttccctgg agcttgcgga ggagatccgc cgcctcgagg aggaggtctt ccgcttggcg    1440
ggccaccctt tcaacctcaa ctcccgggac cagctggaga gggtgctctt tgacgagctt    1500
aggcttcccg ccttggggaa gacgcaaaag acgggcaagc gctccaccag cgccgcggtg    1560
ctggaggccc tacggggagcc ccaccccatc gtggagaaga tcctccagca ccgggagctc    1620
accaagctca agaacaccta cgtggacccc ctcccaagcc tcgtccaccc gaatacgggc    1680
cgcctccaca cccgcttcaa ccagacgcc acggccacgg ggaggcttag tagctccgac    1740
cccaacctgc agaacatccc cgtccgcacc cccttgggcc agaggatccg ccgggccttc    1800
gtggccgagg cgggttgggc gttggtggcc ctggactata gccagataga gctccgcgtc    1860
ctcgcccacc tctccgggga cgagaacctg atcagggtct tccaggaggg gaaggacatc    1920
cacacccaga ccgcaagctg gatgttcggc gtcccccgg aggccgtgga tcccctgatg    1980
cgccgggcgg ccaagacggt gaactacggc gtcctctacg gcatgtccgc ccataggctc    2040
tcccaggagc ttgccatccc ctacgaggag gcggtggcct ttatagagcg ctacttccaa    2100
agcttcccca aggtgcgggc ctggatagaa aagaccctgg aggagggag gaagcggggc    2160
tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
```

| | |
|---|---|
| gacctcatga agctcgccat ggtgaagctc ttccccccgcc tccgggagat ggggggcccgc | 2340 |
| atgctcctcc aggtccacga cgagctcctc ctggaggccc ccaagcgcg ggccgaggag | 2400 |
| gtggcggctt tggccaagga ggccatggag aaggcctatc ccctcgccgt gcccctggag | 2460 |
| gtggaggtgg ggatggggga ggactggctt tccgccaagg gttag | 2505 |

<210> SEQ ID NO 8
<211> LENGTH: 2505
<212> TYPE: DNA
<213> ORGANISM: Thermus thermophilus

<400> SEQUENCE: 8

| | |
|---|---|
| atggaggcga tgcttccgct ctttgaaccc aaaggccggg tcctcctggt ggacggccac | 60 |
| cacctggcct accgcacctt cttcgccctg aagggcctca ccacgagccg ggcgaaccg | 120 |
| gtgcaggcgg tctacggctt cgccaagagc ctcctcaagg ccctgaagga ggacgggtac | 180 |
| aaggccgtct tcgtggtctt tgacgccaag gccccctcct tccgccacga ggcctacgag | 240 |
| gcctacaagg cggggagggc cccgaccccc gaggacttcc ccggcagct cgccctcatc | 300 |
| aaggagctgg tggacctctt ggggtttact cgcctcgagg tccgggcttt gaggcggac | 360 |
| gacgtcctcg ccaccctggc caagaaggcg gaaaagaag ggtacgaggt gcgcatcctc | 420 |
| accgccgacc gggacctcta ccagctcgtc tccgaccggg tcgccgtcct ccaccccgag | 480 |
| ggccacctca tcaccccgga gtggctttgg gagaagtacg gcctcaggcc ggagcagtgg | 540 |
| gtggacttcc gcgccctcgt aggggacccc tccgacaacc tccccggggt caagggcatc | 600 |
| ggggagaaga ccgccctcaa gctccttaag gagtggggaa gcctggaaaa cctcctcaag | 660 |
| aacctggacc gggtgaagcc ggaaagcgtc cgggagaaga tcaaggccca cctggaagac | 720 |
| ctcaggctct ccttggagct ctcccgggtg cgcaccgacc tccccctgga ggtggacctc | 780 |
| gcccagggc gggagcccga ccgggaaggg cttaggcct tcctggagag gctagagttc | 840 |
| ggcagcctcc tccacgagtt cggcctcctg gaggcccccg ccccctgga ggaggccccc | 900 |
| tggccccgc cggaagggc cttcgtgggc ttcgtcctct cccgccccga gcccatgtgg | 960 |
| gcggagctta agccctggc cgcctgcagg acggccggg tgcaccgggc ggaggacccc | 1020 |
| ttggcggggc ttaaggacct caaggaggtc cggggcctcc tcgccaagga cctcgccgtt | 1080 |
| ttggcctcga gggagggct agacctcgtg cccggggacg accccatgct cctcgcctac | 1140 |
| ctcctggacc cctccaacac caccccgag ggggtggcgc ggcgctacgg gggggagtgg | 1200 |
| acggaggacg ccgcccagcg ggccctcctc tcggagagcg tccagcagaa cctccttaag | 1260 |
| cgcctccagg gggaggagaa gctcctctgg ctctaccacg aggtggaaaa gccctctcc | 1320 |
| cgggtcctgg cccacatgga ggccaccggg gtacggctgg acgtggccta ccttcaggcc | 1380 |
| ctttccctgg agcttgcgga ggagatccgc cgcctcgagg aggaggtctt ccgcttggcg | 1440 |
| ggccacccct tcaacctcaa ctcccgggac cagctgaaa gggtgctctt tgacgagctt | 1500 |
| aggcttcccg ccttggggaa gacgcaaaag acgggcaagc gctccaccag cgccgcggtg | 1560 |
| ctggaggccc tacggaggc ccaccccatc gtggagaaga tcctccagca ccggagctc | 1620 |
| accaagctca agaacaccta cgtggacccc ctcccaagcc tcgtccaccc gaggacgggc | 1680 |
| cgcctccaca cccgcttcaa ccagacggcc acggccacgg ggaggcttag tagctccgac | 1740 |
| cccaacctgc agaacatccc cgtccgcacc cccttgggcc agaggatccg ccgggccttc | 1800 |
| gtagccgagg cggatgggc gttggtggcc ctggactata gccagataga gctccgcgtc | 1860 |
| ctcgcccacc tctccgggga cgagaacctg atcagggtct tccaggaggg gaaggacatc | 1920 |

```
cacacccaga ccgcaagctg gatgttcggt gtccccccgg aggccgtgga cccctgatg    1980 cgccgggcgg ccaagacggt gaactacggc gtcctctacg gcatgtccgc caccggctc    2040 tcccaggagc tttccatccc ctacgaggag gcggtggcct ttatagagcg ctacttccaa    2100
agcttcccca aggtgcgggc ctggatagaa aagaccctgg aggagggggag gaagcggggc    2160 tacgtggaaa ccctcttcgg aagaaggcgc tacgtgcccg acctcaacgc ccgggtgaag    2220
agcgtcaggg aggccgcgga cgcatggcc ttcaacatgc ccgtccaggg caccgccgcc    2280
gacctcatga agctcgccat ggtgaagctc ttcccccgcc tccgggagat gggggcccgc    2340
atgctcctcc aggtccacga cgagctcctc ctggaggccc ccaagcgcg gccgaggag    2400 gtggcggctt tggccaagga ggccatggag aaggcctatc ccctcgccgt accctggag    2460 gtggaggtgg ggatcgggga ggactggctt tccgccaagg gctag                  2505

<210> SEQ ID NO 9
<211> LENGTH: 2505
<212> TYPE: DNA
<213> ORGANISM: Thermus thermophilus

<400> SEQUENCE: 9
atggaggcga tgcttccgct cttgaaccc aaaggccggg tcctcctggt ggacggccac     60
cacctggcct accgcacctt cttcgccctg aagggcctca ccacgagccg gggcgaaccg    120
gtgcaggcgg tctacggctt cgccaagagc ctcctcaagg ccctgaagga ggacgggtac    180
aaggccgtct tcgtggtctt tgacgccaag gccccctcct tccgccacga ggcctacgag    240
gcctacaagg cggggaggc cccgaccccc gaggacttcc cccggcagct cgccctcatc    300
aaggagctgg tggacctcct ggggtttacc cgcctgaggg tccccggcta cgaggcggac    360
gacgtcctcg ccaccctggc caagaaggcg gaaaaggagg gtacgaggt gcgcatcctc    420 accgccgacc gcgacctcta ccaactcgtc tccgaccgcg tcgccgtcct ccaccccgag    480
ggccacctca tcacccccgga gtggcttgg gagaagtacg gcctcaagcc ggagcagtgg    540
gtggacttcc gcgccctcgt gggggacccc tccgacaacc tcccggggt caagggcatc    600 ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggcttt ccttggagct ctccggggtg cgcaccgacc tccccctgga ggtggacctc    780
gcccaggggc gggagcccga ccggaggg cttagggcct tcctggagag ctggagttc    840 ggcagcctcc tccacgagtt cggcctcctg gaggcccccg ccccctgga ggaggccccc    900 tggccccgc cggaaggggc cttcgtgggc ttcgtcctct cccgccccga gcccatgtgg    960
gcggagctta agccctggc cgcctgcagg acggccgggg tgcaccgggc agcagaccc    1020 ttggcgggc taaaggacct caaggaggtc cggggcctcc tcgccaagga cctcgccgtc    1080
ttggcctcga gggaggggct agacctcgtg cccgggacg acccatgct cctcgcctac    1140 ctcctggacc cctccaacac caccccgag ggggtggcgc ggcgctacgg ggggagtgg    1200 acggaggacg ccgccaccg ggccctcctc tcggagaggc tccatcggaa cctccttaag    1260
cgcctcgagg gggaggagaa gctcctttgg ctctaccacg aggtggaaaa gccctctcc    1320 cgggtcctgg cccacatgga ggccaccggg gtacggctgg acgtggccta ccttcaggcc    1380
ctttccctgg agcttgcgga ggagatccgc cgcctcgagg aggaggtctt ccgcttggcg    1440
gccaccccct tcaacctcaa ctcccggggac cagctggaaa gggtgctctt tgacgagctt    1500
aggcttcccg ccttggggaa gacgcaaaag acgggcaagc gctccaccag cgccgcggtg    1560
```

```
ctggaggccc tacgggaggc ccaccccatc gtggagaaga tcctccagca ccgggagctc    1620
accaagctca agaacaccta cgtggacccc ctcccaagcc tcgtccaccc gaggacgggc    1680
cgcctccaca cccgcttcaa ccagacggcc acggccacgg ggaggcttag tagctccgac    1740
cccaacctgc agaacatccc cgtccgcacc cccttgggcc agaggatccg ccgggccttc    1800
gtggccgagg cgggatgggc gttggtggcc ctggactata gccagataga gctccgcgtc    1860
ctcgccaccc tctccgggga cgagaacctg atcagggtct tccaggaggg gaaggacatc    1920
cacacccaga ccgcaagctg gatgttcggc gtccccccgg aggccgtgga ccccctgatg    1980
cgccgggcgg ccaagacggt gaactacggc gtcctctacg gcatgtccgc ccataggctc    2040
tcccaggagc ttgccatccc ctacgaggag gcggtggcct ttatagagcg ctacttccaa    2100
agcttcccca aggtgcgggc ctggatagaa aagaccctgg aggaggggag aaagcggggc    2160
tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
gacctcatga agctcgccat ggtgaagctc ttcccccgcc tccgggagat gggggcccgc    2340
atgctcctcc aggtccacga cgagctcctc ctggaggccc ccaagcgcgg ggccgaggag    2400
gtggcggctt tggccaagga ggccatggag aaggcctatc ccctcgccgt gccccctggag    2460 gtggaggtgg ggatggggga ggactggctt tccgccaagg gttag                   2505
```

<210> SEQ ID NO 10
<211> LENGTH: 2505
<212> TYPE: DNA
<213> ORGANISM: Thermus thermophilus

<400> SEQUENCE: 10

```
atggaggcga tgcttccgct ctttgaaccc aaaggccggg tcctcctggt ggacggccac      60
cacctggcct accgcacctt cttcgccctg aagggcctca ccacgagccg ggcgaaccg     120 gtgcaggcgg tctacgactt cgccaagagc ctcctcaagg ccctgaagga ggacgggtac    180
aaggccgtct tcgtggtctt tgacgccaag gcccctcct tccgccacga ggcctacgag     240
gcctacaagg cggggagggc cccgacccc gaggacttcc ccggcagct cgccctcatc      300 aaggagctgg tggacctcct ggggtttacc cgcctcgagg tccccggcta cgaggcggac    360
gacgtcctcg ccaccctggc caagaaggcg gaaaaggagg gtacgaggt gcgcatcctc     420 accgccgacc gcgacctcta ccaactcgtc tccgaccgcg tcgccgtcct ccaccccgag    480
ggccacctca tcaccccgga gtggcttttgg cagaagtacg gcctcaagcc ggagcagtgg    540
gtggacttcc gcgccctcgt gggggacccc tccgacaacc tcccggggt caagggcatc     600 ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggcttt ccttggagct ctcccgggtg cgcaccgacc tccccctgga ggtgaccctc    780 gcccagggc gggagcccga ccgggagggg cttagggcct tcctggagag gctggagttc    840
ggcagcctcc tccacgagtt cggcctcctg aggccccg ccccctgga ggaggccccc        900 tggccccgc cggaaggggc cttcgtgggc ttcgtcctct cccgccccga gcccatgtgg      960
gcggagctta agcccctggc cgcctgcagg acggccgggt gcaccgggc agcggaccccg    1020 ttggcggggc taaaggacct caaggaggtc cggggcctcc tcgccaagga cctcgccgtc   1080
ttggcctcga gggagggct agacctcgtg cccggggacg accccatgct cctcgcctac    1140
ctcctggacc cctccaacac cacccccgag ggggtggcgc ggcgctacgg ggggagtgg    1200
```

| | |
|---|---|
| acggaggacg ccgcccaccg ggccctcctc tcggagaggc tccatcggaa cctccttaag | 1260 |
| cgcctccagg gggaggagaa gctcctttgg ctctaccacg aggtggaaaa gcccctctcc | 1320 |
| cgggtcctgg cccacatgga ggccaccggg gtacggctgg acgtggccta cctgcaggcc | 1380 |
| ctttccctgg agcttgcgga ggagatccgc cgcctcgagg aggaggtctt ccgcttggcg | 1440 |
| ggccacccct tcaacctcaa ctcccgggac cagctggaga gggtgctctt tgacgagctt | 1500 |
| aggcttcccg ccttggggaa gacgcaaaag acgggcaagc gctccaccag cgccgcggtg | 1560 |
| ctggaggccc tacgggaggc ccaccccatc gtggagaaga tcctccagca ccgggagctc | 1620 |
| accaagctca agaacaccta cgtggacccc ctcccaagcc tcgtccaccc gaatacgggc | 1680 |
| cgcctccaca cccgcttcaa ccagacggcc acggccacgg ggaggcttag tagctccgac | 1740 |
| cccaacctgc agaacatccc cgtccgcacc cccttgggcc agaggatccg ccgggccttc | 1800 |
| gtggccgagg cgggttgggc gttggtggcc ctggactata gccagataga gctccgcgtc | 1860 |
| ctcgccacc tctccgggga cgagaacctg atcagggtct tccaggaggg gaaggacatc | 1920 |
| cacacccaga ccgcaagctg gatgttcggc gtcccccgg aggccgtgga tcccctgatg | 1980 |
| cgccgggcgg ccaagacggt gaactacggc gtcctctacg gcatgtccgc ccataggctc | 2040 |
| tcccaggagc ttgccatccc ctacgaggag gcggtggcct ttatagagcg ctacttccaa | 2100 |
| agcttcccca aggtgcgggc ctggatagaa aagaccctgg aggaggggag gaagcggggc | 2160 |
| tacgtggaaa ccctcttcgg aagaaggcgc tacgtgcccg acctcaacgc ccgggtgaag | 2220 |
| agcgtcaggg aggccgcgga gcgcatggcc ttcaacatgc ccgtccaggg caccgccgcc | 2280 |
| gacctcatga agctcgccat ggtgaagctc ttccccccgc ccgggagat ggggggcccgc | 2340 |
| atgctcctcc aggtccacga cgagctcctc ctggaggccc ccaagcgcg ggccgaggag | 2400 |
| gtggcggctt tggccaagga ggccatggag aaggcctatc ccctcgccgt gccccctggag | 2460 |
| gtggaggtgg ggatggggga ggactggctt tccgccaagg gttag | 2505 |

<210> SEQ ID NO 11
<211> LENGTH: 2505
<212> TYPE: DNA
<213> ORGANISM: Thermus thermophilus

<400> SEQUENCE: 11

| | |
|---|---|
| atggaggcga tgcttccgct ctttgaaccc aaaggccggg tcctcctggt ggacggccac | 60 |
| cacctggcct accgcacctt cttcgccctg aagggcctca ccacgagccg ggcgaaccg | 120 |
| gtgcaggcgg tctacgactt cgccaagagc ctcctcaagg ccctgaagga ggacgggtac | 180 |
| aaggccgtct tcgtggtctt tgacgccaag gcccctcct tccgccacga ggcctacgag | 240 |
| gcctacaagg cggggagggc cccgacccc gaggacttcc ccggcagct cgccctcatc | 300 |
| aaggagctgg tggacctctt ggggtttact cgcctcgagg tcccgggctt tgaggcggac | 360 |
| gacgtcctcg ccaccctggc caagaaggcg gaaaaagaag gtacgaggt gcgcatcctc | 420 |
| accgccgacc gggacctcta ccagctcgtc tccgaccggg tcgccgtcct ccaccccgag | 480 |
| ggccacctca tcacccggga gtggctttgg gagaagtacg gcctcaggcc ggagcagtgg | 540 |
| gtggacttcc gcgccctcgt aggggacccc tccgacaacc tccccggggt caagggcatc | 600 |
| ggggagaaga ccgccctcaa gctccttaag gagtggggaa gcctggaaaa cctcctcaag | 660 |
| aacctggacc gggtgaagcc ggaaagcgtc cgggagaaga tcaaggccca cctggaagac | 720 |
| ctcaggctct ccttggagct ctcccggtg cgcaccgacc tccccctgga ggtgaccctc | 780 |
| gcccaggggc gggagcccga ccgggaaggg cttagggcct cctggagag gctagagttc | 840 |

```
ggcagcctcc tccacgagtt cggcctcctg gaggcccccg ccccctgga ggaggccccc      900
tggcccccgc cggaagggc cttcgtgggc ttcgtcctct cccgcccga gcccatgtgg       960
gcggagctta agccctggc cgcctgcagg gacggccggg tgcaccgggc ggaggacccc     1020
ttggcggggc ttaaggacct caaggaggtc cggggcctcc tcgccaagga cctcgccgtt    1080
ttggcctcga gggaggggct agacctcgtg cccggggacg accccatgct cctcgcctac    1140
ctcctggacc cctccaacac cacccccgag ggggtggcgc ggcgctacgg gggggagtgg    1200
acggaggacg ccgcccagcg ggccctcctc tcggagaggc tccagcagaa cctccttaag    1260
cgcctccagg gggaggagaa gctcctctgg ctctaccacg aggtggaaaa gcccctctcc    1320
cgggtcctgg cccacatgga ggccaccggg gtacggctgg acgtggccta ccttcaggcc    1380
ctttccctgg agcttgcgga ggagatccgc cgcctcgagg aggaggtctt ccgcttggcg    1440
ggccacccct tcaacctcaa ctcccgggac cagctggaaa gggtgctctt tgacgagctt    1500
aggcttcccg ccttggggaa gacgcaaaag acgggcaagc gctccaccag cgccgcggtg    1560
ctggaggccc tacgggaggc ccaccccatc gtggagaaga tcctccagca ccgggagctc    1620
accaagctca gaacacccta cgtggacccc ctcccaagcc tcgtccaccc gaggacgggc    1680
cgcctccaca cccgcttcaa ccagacggcc acggccacgg ggaggcttag tagctccgac    1740
cccaacctgc agaacatccc cgtccgcacc cccttgggcc agaggatccg ccgggccttc    1800
gtagccgagg cgggatgggc gttggtggcc ctggactata gccagataga gctccgcgtc    1860
ctcgcccacc tctccgggga cgagaacctg atcagggtct tccaggaggg gaaggacatc    1920
cacacccaga ccgcaagctg gatgttcggt gtccccccgg aggccgtgga ccccctgatg    1980
cgccgggcgg ccaagacggt gaactacggc gtcctctacg gcatgtccgc ccaccggctc    2040
tcccaggagc tttccatccc ctacgaggag gcggtggcct ttatagagcg ctacttccaa    2100
agcttcccca aggtgcgggc ctggatagaa aagaccctgg aggaggggag gaagcggggc    2160
tacgtggaaa ccctcttcgg aagaaggcgc tacgtgcccg acctcaacgc ccgggtgaag    2220
agcgtcaggg aggccgcgga gcgcatggcc ttcaacatgc ccgtccaggg caccgccgcc    2280
gacctcatga gctcgccat ggtgaagctc ttccccccgc ccgggagat ggggccccgc     2340
atgctcctcc aggtccacga cgagctcctc ctggaggccc ccaagcgcg ggccgaggag    2400
gtggcggctt tggccaagga ggccatggag aaggcctatc ccctcgccgt accctggag    2460
gtggaggtgg ggatcgggga ggactggctt ccgccaagg gctag                    2505
```

<210> SEQ ID NO 12
<211> LENGTH: 2505
<212> TYPE: DNA
<213> ORGANISM: Thermus thermophilus

<400> SEQUENCE: 12

```
atggaggcga tgcttccgct ctttgaaccc aaaggccggg tcctcctggt ggacggccac      60
cacctggcct accgcacctt cttcgccctg aagggcctca ccacgagccg ggcgaaccg     120
gtgcaggcgg tctacgactt cgccaagagc ctcctcaagg ccctgaagga ggacgggtac    180
aaggccgtct tcgtggtctt tgacgccaag gccccctcct tccgccacga ggcctacgag    240
gcctacaagg cggggagggc cccgacccc gaggacttcc ccggcagct cgccctcatc     300
aaggagctgg tggacctcct ggggtttacc cgcctcgagg tccccggcta cgaggcggac    360
gacgtcctcg ccaccctggc caagaaggcg gaaaaggagg ggtacgaggt gcgcatcctc    420
accgccgacc gcgacctcta ccaactcgtc tccgaccgcg tcgccgtcct ccaccccgag    480
```

```
ggccacctca tcaccccgga gtggctttgg gagaagtacg gcctcaagcc ggagcagtgg    540
gtggacttcc gcgccctcgt gggggacccc tccgacaacc tccccggggt caagggcatc    600
ggggagaaga ccgccctcaa gctcctcaag gagtggggaa gcctggaaaa cctcctcaag    660
aacctggacc gggtaaagcc agaaaacgtc cgggagaaga tcaaggccca cctggaagac    720
ctcaggcttt ccttggagct ctcccgggtg cgcaccgacc tccccctgga ggtggacctc    780
gcccaggggc gggagcccga ccggggaggg cttagggcct tcctggagag gctggagttc    840
ggcagcctcc tccacgagtt cggcctcctg gaggccccccg cccccctgga ggaggccccc    900
tggccccgc cggaagggc cttcgtgggc ttcgtcctct cccgcccga gcccatgtgg    960
gcggagctta agccctggc cgcctgcagg gacgccggg tgcaccgggc agcagacccc   1020
ttggcggggc taaaggacct caaggaggtc cggggcctcc tcgccaagga cctcgccgtc   1080
ttggcctcga gggaggggct agacctcgtg cccggggacg accccatgct cctcgcctac   1140
ctcctggacc cctccaacac cacccccgag ggggtggcgc ggcgctacgg ggggagtgg    1200
acggaggacg ccgcccaccg ggccctcctc tcggagaggc tccatcggaa cctccttaag   1260
cgcctcgagg gggaggagaa gctcctttgg ctctaccacg aggtggaaaa gcccctctcc   1320
cgggtcctgg cccacatgga ggccaccggg gtacggctgg acgtggccta ccttcaggcc   1380
ctttccctgg agcttgcgga ggagatccgc gcctcgagg aggaggtctt ccgcttggcg   1440
ggccaccctt caacctcaa ctcccgggac cagctggaaa gggtgctctt tgacgagctt   1500
aggcttccccg ccttggggaa gacgcaaaag acgggcaagc gctccaccag cgccgcggtg   1560
ctggaggccc tacgggaggc ccaccccatc gtggagaaga tcctccagca ccgggagctc   1620
accaagctca gaacaccta cgtggacccc ctcccaagcc tcgtccaccc gaggacgggc   1680
cgcctccaca cccgcttcaa ccagacgcc acggccacgg ggaggcttag tagctccgac   1740
cccaacctgc agaacatccc cgtccgcacc cccttgggcc agaggatccg ccgggccttc   1800
gtggccgagg cggatgggc gttggtggcc ctggactata gccagataga gctccgcgtc   1860
ctcgccacc tctccgggga cgagaacctg atcagggtct tccaggaggg gaaggacatc   1920
cacacccaga ccgcaagctg gatgttcggc gtccccccgg aggccgtgga cccctgatg    1980
cgccgggcgg ccaagacggt gaactacggc gtcctctacg catgtccgc ccataggctc   2040
tcccaggagc ttgccatcc ctacgaggag gcggtggcct ttatagagcg ctacttccaa   2100
agcttcccca ggtgcgggc ctggatagaa agaccctgg aggaggggag aaagcggggc   2160
tacgtggaaa ccctcttcgg aagaaggcgc tacgtgcccg acctcaacgc ccgggtgaag   2220
agcgtcaggg aggccgcgga gcgcatggcc ttcaacatgc ccgtccaggg caccgccgcc   2280
gacctcatga gctcgccat ggtgaagctc ttccccccgcc tccgggagat gggggcccgc   2340
atgctcctcc aggtccacga cgagctcctc ctggaggccc ccaagcgcg ggccgaggag   2400
gtggcggctt tggccaagga ggccatggag aaggcctatc ccctgccgt gcccctggag   2460
gtggaggtgg ggatggggga ggactggctt tccgccaagg gttag               2505
```

<210> SEQ ID NO 13
<211> LENGTH: 834
<212> TYPE: PRT
<213> ORGANISM: Thermus thermophilus

<400> SEQUENCE: 13

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly

```
                     20                  25                  30
Leu Thr Thr Ser Arg Gly Glu Pro Val Gln Ala Val Tyr Gly Phe Ala
                 35                  40                  45
Lys Ser Leu Leu Lys Ala Leu Lys Glu Asp Gly Tyr Lys Ala Val Phe
 50                  55                  60
Val Val Phe Asp Ala Lys Ala Pro Ser Phe Arg His Glu Ala Tyr Glu
 65                  70                  75                  80
Ala Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Phe Thr Arg Leu
                100                 105                 110
Glu Val Pro Gly Tyr Glu Ala Asp Asp Val Leu Ala Thr Leu Ala Lys
                115                 120                 125
Lys Ala Glu Lys Glu Gly Tyr Glu Val Arg Ile Leu Thr Ala Asp Arg
    130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Gln Lys Tyr Gly Leu Lys
                165                 170                 175
Pro Glu Gln Trp Val Asp Phe Arg Ala Leu Val Gly Asp Pro Ser Asp
                180                 185                 190
Asn Leu Pro Gly Val Lys Gly Ile Gly Glu Lys Thr Ala Leu Lys Leu
                195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
                260                 265                 270
Ala Phe Leu Glu Arg Leu Glu Phe Gly Ser Leu Leu His Glu Phe Gly
    275                 280                 285
Leu Leu Glu Ala Pro Ala Pro Leu Glu Glu Ala Pro Trp Pro Pro Pro
290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
                340                 345                 350
Leu Leu Ala Lys Asp Leu Ala Val Leu Ala Ser Arg Glu Gly Leu Asp
    355                 360                 365
Leu Val Pro Gly Asp Asp Pro Met Leu Leu Ala Tyr Leu Leu Asp Pro
                370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Gln Gly Glu Glu Lys Leu Leu Trp Leu Tyr
                420                 425                 430
His Glu Val Glu Lys Pro Leu Ser Arg Val Leu Ala His Met Glu Ala
                435                 440                 445
```

Thr Gly Val Arg Leu Asp Val Ala Tyr Leu Gln Ala Leu Ser Leu Glu
450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
                675                 680                 685

Glu Glu Ala Val Ala Phe Ile Glu Arg Tyr Phe Gln Ser Phe Pro Lys
                690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 14
<211> LENGTH: 834
<212> TYPE: PRT
<213> ORGANISM: Thermus thermophilus

<400> SEQUENCE: 14

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
210                 215                 220

Val Lys Pro Glu Ser Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Glu Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala Gln Arg Ala Leu Leu Ser Glu Arg Leu Gln Gln
                405                 410                 415
```

```
Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ser Ile Pro Tyr
        675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
            820                 825                 830

Lys Gly
```

<210> SEQ ID NO 15
<211> LENGTH: 834
<212> TYPE: PRT
<213> ORGANISM: Thermus thermophilus

<400> SEQUENCE: 15

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380
```

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Glu Gly Glu Lys Leu Leu Trp Leu Tyr
        420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
            725                 730                 735

Ala Arg Val Lys Ser Val Arg Glu Ala Ala Glu Arg Met Ala Phe Asn
        740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
        770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
            805                 810                 815

Val Pro Leu Glu Val Glu Val Gly Met Gly Glu Asp Trp Leu Ser Ala
            820                 825                 830

Lys Gly

<210> SEQ ID NO 16
<211> LENGTH: 834
<212> TYPE: PRT
<213> ORGANISM: Thermus thermophilus

<400> SEQUENCE: 16

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

```
Leu Leu Ala Lys Asp Leu Ala Val Leu Ala Ser Arg Glu Gly Leu Asp
        355                 360                 365
Leu Val Pro Gly Asp Asp Pro Met Leu Leu Ala Tyr Leu Leu Asp Pro
    370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Gln Gly Glu Lys Leu Leu Trp Leu Tyr
            420                 425                 430
His Glu Val Glu Lys Pro Leu Ser Arg Val Leu Ala His Met Glu Ala
        435                 440                 445
Thr Gly Val Arg Leu Asp Val Ala Tyr Leu Gln Ala Leu Ser Leu Glu
    450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
            515                 520                 525
Pro Ile Val Glu Lys Ile Leu Gln His Arg Glu Leu Thr Lys Leu Lys
        530                 535                 540
Asn Thr Tyr Val Asp Pro Leu Pro Ser Leu Val His Pro Asn Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
        595                 600                 605
Val Ala Leu Asp Tyr Ser Gln Ile Glu Leu Arg Val Leu Ala His Leu
    610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Phe Gly Val Leu
            660                 665                 670
Tyr Gly Met Ser Ala His Arg Leu Ser Gln Glu Leu Ala Ile Pro Tyr
        675                 680                 685
Glu Glu Ala Val Ala Phe Ile Glu Arg Tyr Phe Gln Ser Phe Pro Lys
    690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln
    770                 775                 780
```

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
            805                 810                 815

Val Pro Leu Glu Val Glu Val Gly Met Gly Glu Asp Trp Leu Ser Ala
            820                 825                 830

Lys Gly

<210> SEQ ID NO 17
<211> LENGTH: 834
<212> TYPE: PRT
<213> ORGANISM: Thermus thermophilus

<400> SEQUENCE: 17

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
            35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
            85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
            165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
210                 215                 220

Val Lys Pro Glu Ser Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

-continued

```
Ala Glu Leu Lys Ala Leu Ala Ala Cys Arg Asp Gly Arg Val His Arg
            325                 330                 335

Ala Glu Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Pro Met Leu Leu Ala Tyr Leu Leu Asp Pro
        370                 375                 380

Ser Asn Thr Thr Pro Glu Gly Val Ala Arg Arg Tyr Gly Gly Glu Trp
385                 390                 395                 400

Thr Glu Asp Ala Ala Gln Arg Ala Leu Leu Ser Glu Arg Leu Gln Gln
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
        610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ser Ile Pro Tyr
            675                 680                 685

Glu Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750
```

```
Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
        770                 775                 780

Val His Asp Glu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
            820                 825                 830

Lys Gly

<210> SEQ ID NO 18
<211> LENGTH: 834
<212> TYPE: PRT
<213> ORGANISM: Thermus thermophilus

<400> SEQUENCE: 18

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285
```

-continued

```
Leu Leu Glu Ala Pro Ala Pro Leu Glu Glu Ala Pro Trp Pro Pro
    290                 295                 300

Glu Gly Ala Phe Val Gly Phe Val Leu Ser Arg Pro Gly Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
                340                 345                 350

Leu Leu Ala Lys Asp Leu Ala Val Leu Ala Ser Arg Glu Gly Leu Asp
                355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
                420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
                530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
                675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720
```

-continued

```
Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
                755                 760                 765

Lys Leu Phe Pro Arg Leu Arg Glu Met Gly Ala Arg Met Leu Leu Gln
                770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 19
<211> LENGTH: 834
<212> TYPE: PRT
<213> ORGANISM: Thermus thermophilus

<400> SEQUENCE: 19

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Tyr Glu Ala Asp Asp Val Leu Ala Thr Leu Ala Lys
                115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255
```

-continued

```
Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Tyr Gly Val Leu
            660                 665                 670

Tyr Gly Met Ser Ala His Arg Leu Ser Gln Glu Leu Ala Ile Pro Tyr
            675                 680                 685
```

```
Glu Glu Ala Val Ala Phe Ile Glu Arg Tyr Phe Gln Ser Phe Pro Lys
        690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Tyr Val Pro Asp Leu Asn
                725                 730                 735
Ala Arg Val Lys Ser Val Arg Glu Ala Ala Glu Arg Met Ala Phe Asn
                740                 745                 750
Met Pro Val Gln Gly Thr Ala Ala Asp Leu Met Lys Leu Ala Met Val
            755                 760                 765
Lys Leu Phe Pro Arg Leu Arg Glu Met Gly Ala Arg Met Leu Leu Gln
770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
                820                 825                 830
Lys Gly

<210> SEQ ID NO 20
<211> LENGTH: 834
<212> TYPE: PRT
<213> ORGANISM: Thermus thermophilus

<400> SEQUENCE: 20

Met Glu Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
                20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Tyr Lys Ala Val Phe
50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Phe Glu Ala Asp Asp Val Leu Ala Thr Leu Ala Lys
        115                 120                 125
Lys Ala Glu Lys Glu Gly Tyr Glu Val Arg Ile Leu Thr Ala Asp Arg
130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
        195                 200                 205
Leu Lys Glu Trp Gly Ser Leu Glu Asn Leu Leu Lys Asn Leu Asp Arg
    210                 215                 220
```

-continued

```
Val Lys Pro Glu Ser Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Glu Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala Gln Arg Ala Leu Leu Ser Glu Arg Leu Gln Gln
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655
```

```
Asp Pro Leu Met Arg Arg Ala Ala Lys Thr Val Asn Tyr Gly Val Leu
            660                 665                 670

Tyr Gly Met Ser Ala His Arg Leu Ser Gln Glu Leu Ser Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
                820                 825                 830

Lys Gly

<210> SEQ ID NO 21
<211> LENGTH: 834
<212> TYPE: PRT
<213> ORGANISM: Thermus thermophilus

<400> SEQUENCE: 21

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190
```

```
Asn Leu Pro Gly Val Lys Gly Ile Gly Glu Lys Thr Ala Lys Leu
        195                 200                 205

Leu Lys Glu Trp Gly Ser Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
                275                 280                 285

Leu Leu Glu Ala Pro Ala Pro Leu Glu Glu Ala Pro Trp Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
                340                 345                 350

Leu Leu Ala Lys Asp Leu Ala Val Leu Ala Ser Arg Glu Gly Leu Asp
                355                 360                 365

Leu Val Pro Gly Asp Asp Pro Met Leu Leu Ala Tyr Leu Leu Asp Pro
                370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
                420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
                530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
                595                 600                 605

Val Ala Leu Asp Tyr Ser Gln Ile Glu Leu Arg Val Leu Ala His Leu
610                 615                 620
```

```
Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Tyr Gly Val Leu
        660                 665                 670

Tyr Gly Met Ser Ala His Arg Leu Ser Gln Glu Leu Ala Ile Pro Tyr
    675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 22
<211> LENGTH: 834
<212> TYPE: PRT
<213> ORGANISM: Thermus thermophilus

<400> SEQUENCE: 22

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160
```

```
Gly His Leu Ile Thr Pro Glu Trp Leu Trp Gln Lys Tyr Gly Leu Lys
            165                 170                 175

Pro Glu Gln Trp Val Asp Phe Arg Ala Leu Val Gly Asp Pro Ser Asp
        180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
        290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
                355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590
```

-continued

```
Gly Gln Arg Ile Arg Arg Ala Phe Val Ala Glu Ala Gly Trp Ala Leu
            595                 600                 605
Val Ala Leu Asp Tyr Ser Gln Ile Glu Leu Arg Val Leu Ala His Leu
    610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Tyr Gly Val Leu
            660                 665                 670
Tyr Gly Met Ser Ala His Arg Leu Ser Gln Glu Leu Ala Ile Pro Tyr
    675                 680                 685
Glu Glu Ala Val Ala Phe Ile Glu Arg Tyr Phe Gln Ser Phe Pro Lys
690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
    755                 760                 765
Lys Leu Phe Pro Arg Leu Arg Glu Met Gly Ala Arg Met Leu Leu Gln
770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly

<210> SEQ ID NO 23
<211> LENGTH: 834
<212> TYPE: PRT
<213> ORGANISM: Thermus thermophilus

<400> SEQUENCE: 23

Met Glu Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Tyr Lys Ala Val Phe
    50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Phe Glu Ala Asp Asp Val Leu Ala Thr Leu Ala Lys
        115                 120                 125
```

```
Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
210                 215                 220

Val Lys Pro Glu Ser Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Glu Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
                355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala Gln Arg Ala Leu Leu Ser Glu Arg Leu Gln Gln
                405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
                435                 440                 445

Thr Gly Val Arg Leu Asp Val Ala Tyr Leu Gln Ala Leu Ser Leu Glu
450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560
```

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Tyr Gly Val Leu
            660                 665                 670

Tyr Gly Met Ser Ala His Arg Leu Ser Gln Glu Leu Ser Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
            820                 825                 830

Lys Gly

<210> SEQ ID NO 24
<211> LENGTH: 834
<212> TYPE: PRT
<213> ORGANISM: Thermus thermophilus

<400> SEQUENCE: 24

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

-continued

```
Leu Ala Leu Ile Lys Glu Leu Val Asp Leu Gly Phe Thr Arg Leu
            100                 105                 110

Glu Val Pro Gly Tyr Glu Ala Asp Val Leu Ala Thr Leu Ala Lys
            115                 120                 125

Lys Ala Glu Lys Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
            165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
            210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525
```

```
Pro Ile Val Glu Lys Ile Leu Gln His Arg Glu Leu Thr Lys Leu Lys
    530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
        595                 600                 605
Val Ala Leu Asp Tyr Ser Gln Ile Glu Leu Arg Val Leu Ala His Leu
610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Tyr Gly Val Leu
            660                 665                 670
Tyr Gly Met Ser Ala His Arg Leu Ser Gln Glu Leu Ala Ile Pro Tyr
        675                 680                 685
Glu Glu Ala Val Ala Phe Ile Glu Arg Tyr Phe Gln Ser Phe Pro Lys
690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln
770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                805                 810                 815
Val Pro Leu Glu Val Glu Val Gly Met Gly Glu Asp Trp Leu Ser Ala
            820                 825                 830
Lys Gly

<210> SEQ ID NO 25
<211> LENGTH: 28
<212> TYPE: DNA
<213> ORGANISM: Thermus thermophilus

<400> SEQUENCE: 25
atggaggcga tgcttccgct ctttgaac                                    28

<210> SEQ ID NO 26
<211> LENGTH: 29
<212> TYPE: DNA
<213> ORGANISM: Thermus thermophilus

<400> SEQUENCE: 26
gtcgactaaa cggcagggcc cccctaacc                                   29
```

-continued

<210> SEQ ID NO 27
<211> LENGTH: 28
<212> TYPE: DNA
<213> ORGANISM: Thermus thermophilus

<400> SEQUENCE: 27
atggaggcga tgcttccgct ctttgaac                                    28

<210> SEQ ID NO 28
<211> LENGTH: 29
<212> TYPE: DNA
<213> ORGANISM: Thermus thermophilus

<400> SEQUENCE: 28
gtcgactaaa cggcagggcc cccctaacc                                   29

<210> SEQ ID NO 29
<211> LENGTH: 545
<212> TYPE: PRT
<213> ORGANISM: Thermus thermophilus

<400> SEQUENCE: 29

```
Leu Glu Ala Pro Ala Pro Leu Glu Glu Ala Pro Trp Pro Pro Glu
1               5                   10                  15
Gly Ala Phe Val Gly Phe Val Leu Ser Arg Pro Glu Pro Met Trp Ala
            20                  25                  30
Glu Leu Lys Ala Leu Ala Ala Cys Arg Asp Gly Arg Val His Arg Ala
        35                  40                  45
Ala Asp Pro Leu Ala Gly Leu Lys Asp Leu Lys Glu Val Arg Gly Leu
    50                  55                  60
Leu Ala Lys Asp Leu Ala Val Leu Ala Ser Arg Glu Gly Leu Asp Leu
65                  70                  75                  80
Val Pro Gly Asp Asp Pro Met Leu Leu Ala Tyr Leu Leu Asp Pro Ser
                85                  90                  95
Asn Thr Thr Pro Glu Gly Val Ala Arg Arg Tyr Gly Gly Glu Trp Thr
            100                 105                 110
Glu Asp Ala Ala His Arg Ala Leu Leu Ser Glu Arg Leu His Arg Asn
        115                 120                 125
Leu Leu Lys Arg Leu Gln Gly Glu Glu Lys Leu Leu Trp Leu Tyr His
    130                 135                 140
Glu Val Glu Lys Pro Leu Ser Arg Val Leu Ala His Met Glu Ala Thr
145                 150                 155                 160
Gly Val Arg Leu Asp Val Ala Tyr Leu Gln Ala Leu Ser Leu Glu Leu
                165                 170                 175
Ala Glu Glu Ile Arg Arg Leu Glu Glu Val Phe Arg Leu Ala Gly
            180                 185                 190
His Pro Phe Asn Leu Asn Ser Arg Asp Gln Leu Glu Arg Val Leu Phe
        195                 200                 205
Asp Glu Leu Arg Leu Pro Ala Leu Gly Lys Thr Gln Lys Thr Gly Lys
    210                 215                 220
Arg Ser Thr Ser Ala Ala Val Leu Glu Ala Leu Arg Glu Ala His Pro
225                 230                 235                 240
Ile Val Glu Lys Ile Leu Gln His Arg Glu Leu Thr Lys Leu Lys Asn
                245                 250                 255
Thr Tyr Val Asp Pro Leu Pro Ser Leu Val His Pro Asn Thr Gly Arg
            260                 265                 270
Leu His Thr Arg Phe Asn Gln Thr Ala Thr Ala Thr Gly Arg Leu Ser
```

```
                275                 280                 285
Ser Ser Asp Pro Asn Leu Gln Asn Ile Pro Val Arg Thr Pro Leu Gly
    290                 295                 300

Gln Arg Ile Arg Arg Ala Phe Val Ala Glu Ala Gly Trp Ala Leu Val
305                 310                 315                 320

Ala Leu Asp Tyr Ser Gln Ile Glu Leu Arg Val Leu Ala His Leu Ser
                325                 330                 335

Gly Asp Glu Asn Leu Ile Arg Val Phe Gln Glu Gly Lys Asp Ile His
            340                 345                 350

Thr Gln Thr Ala Ser Trp Met Phe Gly Val Pro Pro Glu Ala Val Asp
        355                 360                 365

Pro Leu Met Arg Arg Ala Ala Lys Thr Val Asn Phe Gly Val Leu Tyr
    370                 375                 380

Gly Met Ser Ala His Arg Leu Ser Gln Glu Leu Ala Ile Pro Tyr Glu
385                 390                 395                 400

Glu Ala Val Ala Phe Ile Glu Arg Tyr Phe Gln Ser Phe Pro Lys Val
                405                 410                 415

Arg Ala Trp Ile Glu Lys Thr Leu Glu Glu Gly Arg Lys Arg Gly Tyr
            420                 425                 430

Val Glu Thr Leu Phe Gly Arg Arg Arg Tyr Val Pro Asp Leu Asn Ala
        435                 440                 445

Arg Val Lys Ser Val Arg Glu Ala Ala Glu Arg Met Ala Phe Asn Met
    450                 455                 460

Pro Val Gln Gly Thr Ala Ala Asp Leu Met Lys Leu Ala Met Val Lys
465                 470                 475                 480

Leu Phe Pro Arg Leu Arg Glu Met Gly Ala Arg Met Leu Leu Gln Val
                485                 490                 495

His Asp Glu Leu Leu Leu Glu Ala Pro Gln Ala Arg Ala Glu Glu Val
            500                 505                 510

Ala Ala Leu Ala Lys Glu Ala Met Glu Lys Ala Tyr Pro Leu Ala Val
        515                 520                 525

Pro Leu Glu Val Glu Val Gly Met Gly Glu Asp Trp Leu Ser Ala Lys
    530                 535                 540

Gly
545

<210> SEQ ID NO 30
<211> LENGTH: 545
<212> TYPE: PRT
<213> ORGANISM: Thermus thermophilus

<400> SEQUENCE: 30

Leu Glu Ala Pro Ala Pro Leu Glu Glu Ala Pro Trp Pro Pro Pro Glu
1               5                   10                  15

Gly Ala Phe Val Gly Phe Val Leu Ser Arg Pro Glu Pro Met Trp Ala
            20                  25                  30

Glu Leu Lys Ala Leu Ala Ala Cys Arg Asp Gly Arg Val His Arg Ala
        35                  40                  45

Glu Asp Pro Leu Ala Gly Leu Lys Asp Leu Lys Glu Val Arg Gly Leu
    50                  55                  60

Leu Ala Lys Asp Leu Ala Val Leu Ala Ser Arg Glu Gly Leu Asp Leu
65                  70                  75                  80

Val Pro Gly Asp Asp Pro Met Leu Leu Ala Tyr Leu Leu Asp Pro Ser
                85                  90                  95

Asn Thr Thr Pro Glu Gly Val Ala Arg Arg Tyr Gly Gly Glu Trp Thr
```

-continued

```
            100                 105                 110
Glu Asp Ala Ala Gln Arg Ala Leu Leu Ser Glu Arg Leu Gln Gln Asn
            115                 120                 125

Leu Leu Lys Arg Leu Gln Gly Glu Glu Lys Leu Leu Trp Leu Tyr His
        130                 135                 140

Glu Val Glu Lys Pro Leu Ser Arg Val Leu Ala His Met Glu Ala Thr
145                 150                 155                 160

Gly Val Arg Leu Asp Val Ala Tyr Leu Gln Ala Leu Ser Leu Glu Leu
                165                 170                 175

Ala Glu Glu Ile Arg Arg Leu Glu Glu Val Phe Arg Leu Ala Gly
            180                 185                 190

His Pro Phe Asn Leu Asn Ser Arg Asp Gln Leu Glu Arg Val Leu Phe
                195                 200                 205

Asp Glu Leu Arg Leu Pro Ala Leu Gly Lys Thr Gln Lys Thr Gly Lys
        210                 215                 220

Arg Ser Thr Ser Ala Ala Val Leu Glu Ala Leu Arg Glu Ala His Pro
225                 230                 235                 240

Ile Val Glu Lys Ile Leu Gln His Arg Glu Leu Thr Lys Leu Lys Asn
                245                 250                 255

Thr Tyr Val Asp Pro Leu Pro Ser Leu Val His Pro Arg Thr Gly Arg
            260                 265                 270

Leu His Thr Arg Phe Asn Gln Thr Ala Thr Ala Thr Gly Arg Leu Ser
                275                 280                 285

Ser Ser Asp Pro Asn Leu Gln Asn Ile Pro Val Arg Thr Pro Leu Gly
        290                 295                 300

Gln Arg Ile Arg Arg Ala Phe Val Ala Glu Ala Gly Trp Ala Leu Val
305                 310                 315                 320

Ala Leu Asp Tyr Ser Gln Ile Glu Leu Arg Val Leu Ala His Leu Ser
                325                 330                 335

Gly Asp Glu Asn Leu Ile Arg Val Phe Gln Glu Gly Lys Asp Ile His
            340                 345                 350

Thr Gln Thr Ala Ser Trp Met Phe Gly Val Pro Pro Glu Ala Val Asp
            355                 360                 365

Pro Leu Met Arg Arg Ala Ala Lys Thr Val Asn Phe Gly Val Leu Tyr
        370                 375                 380

Gly Met Ser Ala His Arg Leu Ser Gln Glu Leu Ser Ile Pro Tyr Glu
385                 390                 395                 400

Glu Ala Val Ala Phe Ile Glu Arg Tyr Phe Gln Ser Phe Pro Lys Val
                405                 410                 415

Arg Ala Trp Ile Glu Lys Thr Leu Glu Glu Gly Arg Lys Arg Gly Tyr
            420                 425                 430

Val Glu Thr Leu Phe Gly Arg Arg Tyr Val Pro Asp Leu Asn Ala
            435                 440                 445

Arg Val Lys Ser Val Arg Glu Ala Ala Glu Arg Met Ala Phe Asn Met
        450                 455                 460

Pro Val Gln Gly Thr Ala Ala Asp Leu Met Lys Leu Ala Met Val Lys
465                 470                 475                 480

Leu Phe Pro Arg Leu Arg Glu Met Gly Ala Arg Met Leu Leu Gln Val
                485                 490                 495

His Asp Glu Leu Leu Leu Glu Ala Pro Gln Ala Arg Ala Glu Val
            500                 505                 510

Ala Ala Leu Ala Lys Glu Ala Met Glu Lys Ala Tyr Pro Leu Ala Val
            515                 520                 525
```

```
Pro Leu Glu Val Glu Val Gly Ile Gly Glu Asp Trp Leu Ser Ala Lys
                530                 535                 540
Gly
545

<210> SEQ ID NO 31
<211> LENGTH: 545
<212> TYPE: PRT
<213> ORGANISM: Thermus thermophilus

<400> SEQUENCE: 31

Leu Glu Ala Pro Ala Pro Leu Glu Ala Pro Trp Pro Pro Glu
  1               5                  10                  15

Gly Ala Phe Val Gly Phe Val Leu Ser Arg Pro Glu Pro Met Trp Ala
                 20                  25                  30

Glu Leu Lys Ala Leu Ala Ala Cys Arg Asp Gly Arg Val His Arg Ala
             35                  40                  45

Ala Asp Pro Leu Ala Gly Leu Lys Asp Leu Lys Glu Val Arg Gly Leu
         50                  55                  60

Leu Ala Lys Asp Leu Ala Val Leu Ala Ser Arg Glu Gly Leu Asp Leu
 65                  70                  75                  80

Val Pro Gly Asp Asp Pro Met Leu Leu Ala Tyr Leu Leu Asp Pro Ser
                 85                  90                  95

Asn Thr Thr Pro Glu Gly Val Ala Arg Arg Tyr Gly Gly Glu Trp Thr
            100                 105                 110

Glu Asp Ala Ala His Arg Ala Leu Leu Ser Glu Arg Leu His Arg Asn
        115                 120                 125

Leu Leu Lys Arg Leu Glu Gly Glu Lys Leu Leu Trp Leu Tyr His
130                 135                 140

Glu Val Glu Lys Pro Leu Ser Arg Val Leu Ala His Met Glu Ala Thr
145                 150                 155                 160

Gly Val Arg Leu Asp Val Ala Tyr Leu Gln Ala Leu Ser Leu Glu Leu
                165                 170                 175

Ala Glu Glu Ile Arg Arg Leu Glu Glu Val Phe Arg Leu Ala Gly
            180                 185                 190

His Pro Phe Asn Leu Asn Ser Arg Asp Gln Leu Glu Arg Val Leu Phe
        195                 200                 205

Asp Glu Leu Arg Leu Pro Ala Leu Gly Lys Thr Gln Lys Thr Gly Lys
    210                 215                 220

Arg Ser Thr Ser Ala Ala Val Leu Glu Ala Leu Arg Glu Ala His Pro
225                 230                 235                 240

Ile Val Glu Lys Ile Leu Gln His Arg Glu Leu Thr Lys Leu Lys Asn
                245                 250                 255

Thr Tyr Val Asp Pro Leu Pro Ser Leu Val His Pro Arg Thr Gly Arg
            260                 265                 270

Leu His Thr Arg Phe Asn Gln Thr Ala Thr Ala Thr Gly Arg Leu Ser
        275                 280                 285

Ser Ser Asp Pro Asn Leu Gln Asn Ile Pro Val Arg Thr Pro Leu Gly
    290                 295                 300

Gln Arg Ile Arg Arg Ala Phe Val Ala Glu Ala Gly Trp Ala Leu Val
305                 310                 315                 320

Ala Leu Asp Tyr Ser Gln Ile Glu Leu Arg Val Leu Ala His Leu Ser
                325                 330                 335

Gly Asp Glu Asn Leu Ile Arg Val Phe Gln Glu Gly Lys Asp Ile His
            340                 345                 350
```

-continued

```
Thr Gln Thr Ala Ser Trp Met Phe Gly Val Pro Pro Glu Ala Val Asp
    355                 360                 365

Pro Leu Met Arg Arg Ala Ala Lys Thr Val Asn Phe Gly Val Leu Tyr
    370                 375                 380

Gly Met Ser Ala His Arg Leu Ser Gln Glu Leu Ala Ile Pro Tyr Glu
385                 390                 395                 400

Glu Ala Val Ala Phe Ile Glu Arg Tyr Phe Gln Ser Phe Pro Lys Val
                405                 410                 415

Arg Ala Trp Ile Glu Lys Thr Leu Glu Glu Gly Arg Lys Arg Gly Tyr
            420                 425                 430

Val Glu Thr Leu Phe Gly Arg Arg Arg Tyr Val Pro Asp Leu Asn Ala
        435                 440                 445

Arg Val Lys Ser Val Arg Glu Ala Ala Glu Arg Met Ala Phe Asn Met
    450                 455                 460

Pro Val Gln Gly Thr Ala Ala Asp Leu Met Lys Leu Ala Met Val Lys
465                 470                 475                 480

Leu Phe Pro Arg Leu Arg Glu Met Gly Ala Arg Met Leu Leu Gln Val
                485                 490                 495

His Asp Glu Leu Leu Leu Glu Ala Pro Gln Ala Arg Ala Glu Glu Val
            500                 505                 510

Ala Ala Leu Ala Lys Glu Ala Met Glu Lys Ala Tyr Pro Leu Ala Val
        515                 520                 525

Pro Leu Glu Val Glu Val Gly Met Gly Glu Asp Trp Leu Ser Ala Lys
    530                 535                 540

Gly
545
```

US 8,399,231 B2

THERMUS THERMOPHILUS NUCLEIC ACID POLYMERASES

CROSS REFERENCE TO RELATED APPLICATIONS

This application is a Continuation Application of U.S. patent application Ser. No. 12/193,691, filed Aug. 18, 2008; which is a Divisional Application of U.S. patent application Ser. No. 11/609,174, filed Dec. 11, 2006; which is a Divisional Application of U.S. patent application Ser. No. 10/303,110, now U.S. Pat. No. 7,148,340, filed Nov. 22, 2002; of which claims a priority benefit under 35 U.S.C. §119(e) from U.S. Patent Application No. 60/336,046, filed Nov. 30, 2001, all of which are incorporated herein by reference in their entireties.

FIELD OF THE INVENTION

The invention relates to nucleic acids and polypeptides for nucleic acid polymerases from a thermophilic organism, *Thermus thermophilus*.

BACKGROUND OF THE INVENTION

DNA polymerases are naturally-occurring intracellular enzymes used by a cell for replicating DNA by reading one nucleic acid strand and manufacturing its complement. Enzymes having DNA polymerase activity catalyze the formation of a bond between the 3' hydroxyl group at the growing end of a nucleic acid primer and the 5' phosphate group of a newly added nucleotide triphosphate. Nucleotide triphosphates used for DNA synthesis are usually deoxyadenosine triphosphate (A), deoxythymidine triphosphate (T), deoxycytosine triphosphate (C) and deoxyguanosine triphosphate (G), but modified or altered versions of these nucleotides can also be used. The order in which the nucleotides are added is dictated by hydrogen-bond formation between A and T nucleotide bases and between G and C nucleotide bases.

Bacterial cells contain three types of DNA polymerases, termed polymerase I, II and III. DNA polymerase I is the most abundant polymerase and is generally responsible for certain types of DNA repair, including a repair-like reaction that permits the joining of Okazaki fragments during DNA replication. Polymerase I is essential for the repair of DNA damage induced by UV irradiation and radiomimetic drugs. DNA Polymerase II is thought to play a role in repairing DNA damage that induces the SOS response. In mutants that lack both polymerase I and III, polymerase II repairs UV-induced lesions. Polymerase I and II are monomeric polymerases while polymerase III is a multisubunit complex.

Enzymes having DNA polymerase activity are often used in vitro for a variety of biochemical applications including cDNA synthesis and DNA sequencing reactions. See Sambrook e al., Molecular Cloning: A Laboratory Manual (3rd ed. Cold Spring Harbor Laboratory Press, 2001, hereby incorporated by reference. DNA polymerases are also used for amplification of nucleic acids by methods such as the polymerase chain reaction (PCR) (Mullis et al., U.S. Pat. Nos. 4,683,195, 4,683,202, and 4,800,159, incorporated by reference) and RNA transcription-mediated amplification methods (e.g., Kacian et al., PCT Publication No. WO91/01384, incorporated by reference).

DNA amplification utilizes cycles of primer extension through the use of a DNA polymerase activity, followed by thermal denaturation of the resulting double-stranded nucleic acid in order to provide a new template for another round of primer annealing and extension. Because the high temperatures necessary for strand denaturation result in the irreversible inactivations of many DNA polymerases, the discovery and use of DNA polymerases able to remain active at temperatures above about 37 C provides an advantage in cost and labor efficiency.

Thermostable DNA polymerases have been discovered in a number of thermophilic organisms including *Thermus aquaticus*, one strain of *Thermus thermophilus*, and certain species within the genera the *Bacillus, Thermococcus, Sulfobus,* and *Pyrococcus*. A full length thermostable DNA polymerase derived from *Thermus aquaticus* (Taq) has been described by Lawyer, et al., J. Biol. Chem. 264:6427-6437 (1989) and Gelfand et al, U.S. Pat. No. 5,079,352. The cloning and expression of truncated versions of that DNA polymerase are further described in Lawyer et al., in PCR Methods and Applications, 2:275-287 (1993), and Barnes, PCT Publication No. WO92/06188 (1992). Sullivan reports the cloning of a mutated version of the Taq DNA polymerase in EPO Publication No. 0482714A1 (1992). A DNA polymerase from *Thermus thermophilus* has also been cloned and expressed. Asakura et al., J. Ferment. Bioeng. (Japan), 74:265-269 (1993). However, the properties of the various DNA polymerases vary. Accordingly, new DNA polymerases are needed that have improved sequence discrimination, better salt tolerance, varying degrees of thermostability, improved tolerance for labeled or dideoxy nucleotides and other valuable properties.

SUMMARY OF THE INVENTION

The invention provides nucleic acid polymerase enzymes isolated from a thermophilic organism, *Thermus thermophilus*. The invention provides nucleic acid polymerases from several *Thermus thermophilus* strains, including strain RQ-1, strain GK24 and strain 1b21. Therefore, in one embodiment the invention provides an isolated nucleic acid encoding a *Thermus thermophilus* strain RQ-1 (DSM catalog number 9247) nucleic acid polymerase.

In another embodiment, the invention provides an isolated nucleic acid encoding a nucleic acid polymerase comprising any one of amino acid sequences SEQ ID NO:13-24.

In another embodiment, the invention provides an isolated nucleic acid encoding a derivative nucleic acid polymerase any one of amino acid sequences SEQ ID NO:13-15 having a mutation that decreases 5-3' exonuclease activity. Such a derivative nucleic acid polymerase can have decreased 5-3' exonuclease activity relative to a nucleic acid polymerase comprising any one of amino acid sequences SEQ ID NO:13-15.

In another embodiment, the invention provides an isolated nucleic acid encoding a derivative nucleic acid polymerase comprising any one of amino acid sequences SEQ ID NO:13-15 having a mutation that reduces discrimination against dideoxynucleotide triphosphates. Such a derivative nucleic acid polymerase can have reduced discrimination against dideoxynucleotide triphosphates relative to a nucleic acid polymerase comprising any one of amino acid sequences SEQ ID NO:13-15.

The invention also provides an isolated nucleic acid encoding a nucleic polymerase comprising any one of SEQ ID NO:1-12, and isolated nucleic acids complementary to any one of SEQ ID NO:1-12.

The invention also provides vectors comprising these isolated nucleic acids, including expression vectors comprising a promoter operably linked to these isolated nucleic acids. Host cells comprising such isolated nucleic acids and vectors are also provided by the invention, particularly host cells capable of expressing a thermostable polypeptide encoded by the nucleic acid, where the polypeptide has nucleic acid activity and/or DNA polymerase activity.

The invention also provides isolated polypeptides that can include any one of amino acid sequences SEQ ID NO:13-24. The isolated polypeptides provided by the invention can have any one of amino acid sequences SEQ ID NO:13-24, which can, for example, have a DNA polymerase activity between 50,000 U/mg protein and 500,000 U/mg protein.

In another embodiment, the invention provides an isolated derivative nucleic acid polymerase comprising any one of amino acid sequences SEQ ID NO:13-15 having a mutation that decreases 5-3' exonuclease activity. Such a derivative nucleic acid polymerase can have decreased 5-3' exonuclease activity relative to a nucleic acid polymerase comprising any one of amino acid sequences SEQ ID NO:13-15.

In another embodiment, the invention provides an isolated derivative nucleic acid polymerase comprising any one of amino acid sequences SEQ ID NO:13-15 having a mutation that reduces discrimination against dideoxynucleotide triphosphates. Such a derivative nucleic acid polymerase can have reduced discrimination against dideoxynucleotide triphosphates relative to a nucleic acid polymerase comprising any one of amino acid sequences SEQ ID NO:13-15.

The invention also provides a kit that includes a container containing at least one of the nucleic acid polymerases of the invention. Such a nucleic acid polymerase can have an amino acid sequence comprising any one of amino acid sequences SEQ ID NO:13-24. The kit can also contain an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer. Such kits can, for example, be adapted for performing DNA sequencing, DNA amplification, RNA amplification or primer extension reactions.

The invention further provides a method of synthesizing a nucleic acid that includes contacting a polypeptide comprising any one of amino acid sequences SEQ ID NO:13-24 with a nucleic acid under conditions sufficient to permit polymerization of the nucleic acid. Such a nucleic acid can be a DNA or an RNA.

The invention further provides a method for thermocyclic amplification of nucleic acid that comprises contacting a nucleic acid with a thermostable polypeptide having any one of amino acid sequences SEQ ID NO:13-24 under conditions suitable for amplification of the nucleic acid, and amplifying the nucleic acid. Such amplification can be, for example, by Strand Displacement Amplification or Polymerase Chain Reaction.

The invention also provides a method of primer extending DNA comprising contacting a polypeptide comprising any one of amino acid sequences SEQ ID NO:13-24 with a DNA under conditions sufficient to permit polymerization of DNA. Such primer extension can be performed, for example, to sequence DNA or to amplify DNA.

The invention further provides a method of making a nucleic acid polymerase comprising any one of amino acid sequences SEQ ID NO:13-24, the method comprising incubating a host cell comprising a nucleic acid that encodes a polypeptide comprising any one of amino acid sequences SEQ ID NO:13-24, operably linked to a promoter under conditions sufficient for RNA transcription and translation. In one embodiment, the method uses a nucleic acid that comprises any one of SEQ ID NO:1-12. The invention is also directed to a nucleic acid polymerase made by this method.

DESCRIPTION OF THE FIGURES

FIG. 1 provides a comparison of amino acid sequences of polymerases from four strains of *Thermus thermophilus*: HB8, ZO5, GK24 (Kwon et al. 1997; Genebank accession number U62584) and the *Thermus thermophilus* strain GK24 polymerase of this invention (SEQ ID NO: 9). The four non-conservative differences between the Kwon GK24 amino acid sequence and SEQ ID NO:9 are shown in blue. Single amino acid changes among the four strains are shown in red.

FIG. 2 provides a comparison of amino acid sequences from four different strains of *Thermus thermophilus*: HB8, ZO5, GK24 (Genebank accession number U62584) and RQ-1 (SEQ ID NO:10). The amino acid sequence of the wild-type polymerase from *Thermus thermophilus* strain RQ-1 has eight (8) changes from the sequence of *Thermus thermophilus* strain HB8 and twenty-five (25) changes from the sequence of *Thermus thermophilus* strain ZO5 (U.S. Pat. No. 5,674,738).

FIG. 3 provides a comparison of amino acid sequences of polymerases from two strains of *Thermus thermophilus*: HB8 and 1b21.

DETAILED DESCRIPTION OF THE INVENTION

The present invention relates to nucleic acid and amino acid sequences encoding nucleic acid polymerases from thermophilic organisms. In particular, the present invention provides nucleic acid polymerases from certain strains *Thermus thermophilus*, including strains GK24, RQ-1 and 1b21. The nucleic acid polymerases of the invention can be used in a variety of procedures, including DNA synthesis, reverse transcription, DNA primer extension, DNA sequencing and DNA amplification procedures.

Definitions

The term "amino acid sequence" refers to the positional arrangement and identity of amino acids in a peptide, polypeptide or protein molecule. Use of the term "amino acid sequence" is not meant to limit the amino acid sequence to the complete, native amino acid sequence of a peptide, polypeptide or protein.

"Chimeric" is used to indicate that a nucleic acid, such as a vector or a gene, is comprised of more than one nucleic acid segment and that at least two nucleic acid segments are of distinct origin. Such nucleic acid segments are fused together by recombinant techniques resulting in a nucleic acid sequence, which does not occur naturally.

The term "coding region" refers to the nucleotide sequence that codes for a protein of interest. The coding region of a protein is bounded on the 5' side by the nucleotide triplet "ATG" that encodes the initiator methionine and on the 3' side by one of the three triplets that specify stop codons (i.e., TAA, TAG, TGA).

"Constitutive expression" refers to expression using a constitutive promoter.

"Constitutive promoter" refers to a promoter that is able to express the gene that it controls in all, or nearly all, phases of the life cycle of the cell.

"Complementary" or "complementarity" are used to define the degree of base-pairing or hybridization between nucleic acids. For example, as is known to one of skill in the art, adenine (A) can form hydrogen bonds or base pair with thymine (T) and guanine (G) can form hydrogen bonds or base pair with cytosine (C). Hence, A is complementary to T and G is complementary to C. Complementarity may be complete when all bases in a double-stranded nucleic acid are base paired. Alternatively, complementarity may be "partial," in which only some of the bases in a nucleic acid are matched according to the base pairing rules. The degree of complementarity between nucleic acid strands has an effect on the efficiency and strength of hybridization between nucleic acid strands.

The "derivative" of a reference nucleic acid, protein, polypeptide or peptide, is a nucleic acid, protein, polypeptide or peptide, respectively, with a related but different sequence or chemical structure than the respective reference nucleic acid, protein, polypeptide or peptide. A derivative nucleic acid, protein, polypeptide or peptide is generally made purposefully to enhance or incorporate some chemical, physical or functional property that is absent or only weakly present in the reference nucleic acid, protein, polypeptide or peptide. A derivative nucleic acid generally can differ in nucleotide sequence from a reference nucleic acid whereas a derivative protein, polypeptide or peptide can differ in amino acid sequence from the reference protein, polypeptide or peptide, respectively. Such sequence differences can be one or more substitutions, insertions, additions, deletions, fusions and truncations, which can be present in any combination. Differences can be minor (e.g., a difference of one nucleotide or amino acid) or more substantial. However, the sequence of the derivative is not so different from the reference that one of skill in the art would not recognize that the derivative and reference are related in structure and/or function. Generally, differences are limited so that the reference and the derivative are closely similar overall and, in many regions, identical. A "variant" differs from a "derivative" nucleic acid, protein, polypeptide or peptide in that the variant can have silent structural differences that do not significantly change the chemical, physical or functional properties of the reference nucleic acid, protein, polypeptide or peptide. In contrast, the differences between the reference and derivative nucleic acid, protein, polypeptide or peptide are intentional changes made to improve one or more chemical, physical or functional properties of the reference nucleic acid, protein, polypeptide or peptide.

The terms "DNA polymerase activity," "synthetic activity" and "polymerase activity" are used interchangeably and refer to the ability of an enzyme to synthesize new DNA strands by the incorporation of deoxynucleoside triphosphates. A protein that can direct the synthesis of new DNA strands by the incorporation of deoxynucleoside triphosphates in a template-dependent manner is said to be "capable of DNA synthetic activity."

The term "5' exonuclease activity" refers to the presence of an activity in a protein that is capable of removing nucleotides from the 5' end of a nucleic acid.

The term "3' exonuclease activity" refers to the presence of an activity in a protein that is capable of removing nucleotides from the 3' end of a nucleic acid.

"Expression" refers to the transcription and/or translation of an endogenous or exogeneous gene in an organism. Expression generally refers to the transcription and stable accumulation of mRNA. Expression may also refer to the production of protein.

"Expression cassette" means a nucleic acid sequence capable of directing expression of a particular nucleotide sequence. Expression cassettes generally comprise a promoter operably linked to the nucleotide sequence to be expressed (e.g., a coding region) that is operably linked to termination signals. Expression cassettes also typically comprise sequences required for proper translation of the nucleotide sequence. The expression cassette comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "gene" is used broadly to refer to any segment of nucleic acid associated with a biological function. The term "gene" encompasses the coding region of a protein, polypeptide, peptide or structural RNA. The term "gene" also includes sequences up to a distance of about 2 kb on either end of a coding region. These sequences are referred to as "flanking" sequences or regions (these flanking sequences are located 5' or 3' to the non-translated sequences present on the mRNA transcript). The 5' flanking region may contain regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene can be full length or any portion thereof, so that all activities or functional properties are retained, or so that only selected activities (e.g., enzymatic activity, ligand binding, or signal transduction) of the full-length protein or polypeptide are retained. The protein or polypeptide can include any sequences necessary for the production of a proprotein or precursor polypeptide. The term "native gene" refers to gene that is naturally present in the genome of an untransformed cell.

"Genome" refers to the complete genetic material that is naturally present in an organism and is transmitted from one generation to the next.

The terms "heterologous nucleic acid," or "exogenous nucleic acid" refer to a nucleic acid that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring nucleic acid. Thus, the terms refer to a nucleic acid segment that is foreign or heterologous to the cell, or normally found within the cell but in a position within the cell or genome where it is not ordinarily found.

The term "homology" refers to a degree of similarity between a nucleic acid and a reference nucleic acid or between a polypeptide and a reference polypeptide. Homology may be partial or complete. Complete homology indicates that the nucleic acid or amino acid sequences are identical. A partially homologous nucleic acid or amino acid sequence is one that is not identical to the reference nucleic acid or amino acid sequence. Hence, a partially homologous nucleic acid has one or more nucleotide differences in its sequence relative to the nucleic acid to which it is being compared. The degree of homology can be determined by sequence comparison. Alternatively, as is understood by those skilled in the art, DNA-DNA or DNA-RNA hybridization, under various hybridization conditions, can provide an estimate of the degree of homology between nucleic acids, (see, e.g., Haines and Higgins (eds.), Nucleic Acid Hybridization, IRL Press, Oxford, U.K.).

"Hybridization" refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementary between the hybridizing nucleic acids, the stringency of the conditions involved, the $T_m$ of the formed hybrid, and the G:C ratio within the nucleic acids.

"Inducible promoter" refers to a regulated promoter that can be turned on in one or more cell types by an external stimulus, such as a chemical, light, hormone, stress, temperature or a pathogen.

An "initiation site" is region surrounding the position of the first nucleotide that is part of the transcribed sequence, which is defined as position +1. All nucleotide positions of the gene are numbered by reference to the first nucleotide of the transcribed sequence, which resides within the initiation site. Downstream sequences (i.e., sequences in the 3' direction) are denominated positive, while upstream sequences (i.e., sequences in the 5' direction) are denominated negative.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a purified form or may exist in a non-native environment such as, for example, a transgenic host cell.

The term "invader oligonucleotide" refers to an oligonucleotide that contains sequences at its 3' end that are substantially the same as sequences located at the 5' end of a probe oligonucleotide. These regions will compete for hybridization to the same segment along a complementary target nucleic acid.

The term "label" refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "oligonucleotide" as used herein is defined as a molecule comprised of two or more deoxyribonucleotides or ribonucleotides, preferably more than three, and usually more than ten. There is no precise upper limit on the size of an oligonucleotide. However, in general, an oligonucleotide is shorter than about 250 nucleotides, preferably shorter than about 200 nucleotides and more preferably shorter than about 100 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably linked" means joined as part of the same nucleic acid molecule, so that the function of one is affected by the other. In general, "operably linked" also means that two or more nucleic acids are suitably positioned and oriented so that they can function together. Nucleic acids are often operably linked to permit transcription of a coding region to be initiated from the promoter. For example, a regulatory sequence is said to be "operably linked to" or "associated with" a nucleic acid sequence that codes for an RNA or a polypeptide if the two sequences are situated such that the regulatory sequence affects expression of the coding region (i.e., that the coding sequence or functional RNA is under the transcriptional control of the promoter). Coding regions can be operably-linked to regulatory sequences in sense or anti-sense orientation.

The term "probe oligonucleotide" refers to an oligonucleotide that interacts with a target nucleic acid to form a cleavage structure in the presence or absence of an invader oligonucleotide. When annealed to the target nucleic acid, the probe oligonucleotide and target form a cleavage structure and cleavage occurs within the probe oligonucleotide. The presence of an invader oligonucleotide upstream of the probe oligonucleotide can shift the site of cleavage within the probe oligonucleotide (relative to the site of cleavage in the absence of the invader).

"Promoter" refers to a nucleotide sequence, usually upstream (5') to a coding region, which controls the expression of the coding region by providing the recognition site for RNA polymerase and other factors required for proper transcription. "Promoter" includes but is not limited a minimal promoter that is a short DNA sequence comprised of a TATA-box. Hence, a promoter includes other sequences that serve to specify the site of transcription initiation and control or regulate expression, for example, enhancers. Accordingly, an "enhancer" is a segment of DNA that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Promoters may be derived in their entirety from a native gene, or be composed of different elements derived from different promoters found in nature, or even be comprised of synthetic DNA segments. A promoter may also contain DNA segments that are involved in the binding of protein factors that control the effectiveness of transcription initiation in response to physiological or developmental conditions.

The terms "protein," "peptide" and "polypeptide" are used interchangeably herein.

"Regulatory sequences" and "regulatory elements" refer to nucleotide sequences that control some aspect of the expression of nucleic acid sequences. Such sequences or elements can be located upstream (5' non-coding sequences), within, or downstream (3' non-coding sequences) of a coding sequence. "Regulatory sequences" and "regulatory elements" influence the transcription, RNA processing or stability, or translation of the associated coding sequence. Regulatory sequences include enhancers, introns, promoters, polyadenylation signal sequences, splicing signals, termination signals, and translation leader sequences. They include natural and synthetic sequences.

As used herein, the term "selectable marker" refers to a gene that encodes an observable or selectable trait that is expressed and can be detected in an organism having that gene. Selectable markers are often linked to a nucleic acid of interest that may not encode an observable trait, in order to trace or select the presence of the nucleic acid of interest. Any selectable marker known to one of skill in the art can be used with the nucleic acids of the invention. Some selectable markers allow the host to survive under circumstances where, without the marker, the host would otherwise die. Examples of selectable markers include antibiotic resistance, for example, tetracycline or ampicillin resistance.

As used herein the term "stringency" is used to define the conditions of temperature, ionic strength, and the presence of other compounds such as organic solvents, under which nucleic acid hybridizations are conducted. With "high stringency" conditions, nucleic acid base pairing will occur only between nucleic acids that have a high frequency of complementary base sequences. With "weak" or "low" stringency conditions nucleic acids the frequency of complementary sequences is usually less, so that nucleic acids with differing sequences can be detected and/or isolated.

The terms "substantially similar" and "substantially homologous" refer to nucleotide and amino acid sequences that represent functional equivalents of the instant inventive sequences. For example, altered nucleotide sequences that simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is sufficient to provide an active, thermally stable nucleic acid polymerase. For example, amino acid sequences that are substantially similar to the sequences of the invention are those wherein the overall amino acid identity is 80% or greater, preferably 90% or greater, such as 91%, 92%, 93%, or 94%, and more preferably 95% or greater, such as 96%, 97%, 98%, or 99% relative to the amino acid sequences of the invention.

A "terminating agent," "terminating nucleotide" or "terminator" in relation to DNA synthesis or sequencing refers to compounds capable of specifically terminating a DNA sequencing reaction at a specific base, such compounds include but are not limited to, dideoxynucleosides having a 2', 3' dideoxy structure (e.g., ddATP, ddCTP, ddGTP and ddTTP).

"Thermostable" means that a nucleic acid polymerase remains active at a temperature greater than about 37 C. Preferably, the nucleic acid polymerases of the invention remain active at a temperature greater than about 42 C. More preferably, the nucleic acid polymerases of the invention remain active at a temperature greater than about 50 C. Even more preferably, the nucleic acid polymerases of the invention remain active after exposure to a temperature greater than about 60 C. Most preferably, the nucleic acid polymerases of the invention remain active despite exposure to a temperature greater than about 70 C.

A "transgene" refers to a gene that has been introduced into the genome by transformation and is stably maintained. Transgenes may include, for example, genes that are either heterologous or homologous to the genes of a particular organism to be transformed. Additionally, transgenes may comprise native genes inserted into a non-native organism, or chimeric genes. The term "endogenous gene" refers to a native gene in its natural location in the genome of an organism. A "foreign" or "exogenous" gene refers to a gene not normally found in the host organism but one that is introduced by gene transfer.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms." Transformation may be accomplished by a variety of means known to the art including calcium DNA co-precipitation, electroporation, viral infection, and the like.

The "variant" of a reference nucleic acid, protein, polypeptide or peptide, is a nucleic acid, protein, polypeptide or peptide, respectively, with a related but different sequence than the respective reference nucleic acid, protein, polypeptide or peptide. The differences between variant and reference nucleic acids, proteins, polypeptides or peptides are silent or conservative differences. A variant nucleic acid differs in nucleotide sequence from a reference nucleic acid whereas a variant nucleic acid, protein, polypeptide or peptide differs in amino acid sequence from the reference protein, polypeptide or peptide, respectively. A variant and reference nucleic acid, protein, polypeptide or peptide may differ in sequence by one or more substitutions, insertions, additions, deletions, fusions and truncations, which may be present in any combination. Differences can be minor (e.g., a difference of one nucleotide or amino acid) or more substantial. However, the structure and function of the variant is not so different from the reference that one of skill in the art would not recognize that the variant and reference are related in structure and/or function. Generally, differences are limited so that the reference and the variant are closely similar overall and, in many regions, identical.

The term "vector" is used to refer to a nucleic acid that can transfer another nucleic acid segment(s) into a cell. A "vector" includes, inter alia, any plasmid, cosmid, phage or nucleic acid in double- or single-stranded, linear or circular form that may or may not be self transmissible or mobilizable. It can transform prokaryotic or eukaryotic host cells either by integration into the cellular genome or by existing extrachromosomally (e.g., autonomous replicating plasmid with an origin of replication). Vectors used in bacterial systems often contain an origin of replication that allows the vector to replicate independently of the bacterial chromosome. The term "expression vector" refers to a vector containing an expression cassette.

The term "wild-type" refers to a gene or gene product that has the characteristics of that gene or gene product when isolated from a naturally occurring source. A wild-type gene is the gene form most frequently observed in a population and thus arbitrarily is designed the "normal" or "wild-type" form of the gene. In contrast, the term "variant" or "derivative" refers to a gene or gene product that displays modifications in sequence and or functional properties (i.e., altered characteristics) when compared to the wild-type gene or gene product. Naturally-occurring derivatives can be isolated. They are identified by the fact that they have altered characteristics when compared to the wild-type gene or gene product.

Polymerase Nucleic Acids

The invention provides isolated nucleic acids encoding *Thermus thermophilus* nucleic acid polymerases as well as derivatives fragments and variant nucleic acids thereof that encode an active, thermally stable nucleic acid polymerase. Thus, one aspect of the invention includes the nucleic acid polymerases encoded by the polynucleotide sequences contained in *Thermus thermophilus* strain RQ-1 from the German Collection of Microorganisms (DSM catalog number 9247). Another aspect of the invention provides nucleic acid polymerases from *Thermus thermophilus* strain GK24. While a DNA polymerase from of *Thermus thermophilus* strain GK24 has been cloned (Kwon et al., Mol Cells. 1997 Apr. 30; 7 (2):264-71), the nucleic acid polymerases of *Thermus thermophilus* strain GK24 provided by the invention are distinct. Yet another aspect of the invention provides nucleic acid polymerases from *Thermus thermophilus* strain 1b21. Accordingly, a nucleic acid encoding any one of amino acid sequences SEQ ID NO:13-24, which are amino acid sequences for wild type and several derivative *Thermus thermophilus* nucleic acid polymerases, are contemplated by the present invention.

In one embodiment, the invention provides a nucleic acid of SEQ ID NO:1, encoding a nucleic acid polymerase from a wild type *Thermus thermophilus*, strain GK24. SEQ ID NO:1 is provided below:

```
   1 ATGGAGGCGA TGCTTCCGCT CTTTGAACCC AAAGGCCGGG
     TCCTCCTGGT

51 GGACGGCCAC CACCTGGCCT ACCGCACCTT CTTCGCCCTG
     AAGGGCCTCA

101 CCACGAGCCG GGGCGAACCG GTGCAGGCGG TCTACGGCTT
     CGCCAAGAGC

151 CTCCTCAAGG CCCTGAAGGA GGACGGGTAC AAGGCCGTCT
     TCGTGGTCTT

201 TGACGCCAAG GCCCCCTCCT TCCGCCACGA GGCCTACGAG
     GCCTACAAGG

251 CGGGGAGGGC CCCGACCCCC GAGGACTTCC CCCGGCAGCT
     CGCCCTCATC

301 AAGGAGCTGG TGGACCTCCT GGGGTTTACC CGCCTCGAGG
     TCCCCGGCTA

351 CGAGGCGGAC GACGTCCTCG CCACCCTGGC CAAGAAGGCG
     GAAAAGGAGG

401 GGTACGAGGT GCGCATCCTC ACCGCCGACC GCGACCTCTA
     CCAACTCGTC

451 TCCGACCGCG TCGCCGTCCT CCACCCCGAG GGCCACCTCA
     TCACCCCGGA

501 GTGGCTTTGG CAGAAGTACG GCCTCAAGCC GGAGCAGTGG
     GTGGACTTCC

551 GCGCCCTCGT GGGGGACCCC TCCGACAACC TCCCCGGGGT
     CAAGGGCATC

601 GGGGAGAAGA CCGCCCTCAA GCTCCTCAAG GAGTGGGGAA
     GCCTGGAAAA

651 CCTCCTCAAG AACCTGGACC GGGTAAAGCC AGAAAACGTC
     CGGGAGAAGA

701 TCAAGGCCCA CCTGGAAGAC CTCAGGCTTT CCTTGGAGCT
     CTCCCGGGTG

751 CGCACCGACC TCCCCCTGGA GGTGGACCTC GCCCAGGGGC
     GGGAGCCCGA

801 CCGGGAGGGG CTTAGGGCCT TCCTGGAGAG GCTGGAGTTC
     GGCAGCCTCC

851 TCCACGAGTT CGGCCTCCTG GAGGCCCCCG CCCCCCTGGA
     GGAGGCCCCC

901 TGGCCCCCGC CGGAAGGGGC CTTCGTGGGC TTCGTCCTCT
     CCCGCCCCGA

951 GCCCATGTGG GCGGAGCTTA AAGCCCTGGC CGCCTGCAGG
     GACGGCCGGG

1001 TGCACCGGGC AGCGGACCCC TTGGCGGGGC TAAAGGACCT
     CAAGGAGGTC

1051 CGGGGCCTCC TCGCCAAGGA CCTCGCCGTC TTGGCCTCGA
     GGGAGGGGCT

1101 AGACCTCGTG CCCGGGGACG ACCCCATGCT CCTCGCCTAC
     CTCCTGGACC

1151 CCTCCAACAC CACCCCCGAG GGGGTGGCGC GGCGCTACGG
     GGGGGAGTGG

1201 ACGGAGGACG CCGCCCACCG GGCCCTCCTC TCGGAGAGGC
     TCCATCGGAA

1251 CCTCCTTAAG CGCCTCCAGG GGGAGGAGAA GCTCCTTTGG
     CTCTACCACG

1301 AGGTGGAAAA GCCCCTCTCC CGGGTCCTGG CCCACATGGA
     GGCCACCGGG

1351 GTACGGCTGG ACGTGGCCTA CCTGCAGGCC CTTTCCCTGG
     AGCTTGCGGA

1401 GGAGATCCGC CGCCTCGAGG AGGAGGTCTT CCGCTTGGCG
     GGCCACCCCT

1451 TCAACCTCAA CTCCCGGGAC CAGCTGGAGA GGGTGCTCTT
     TGACGAGCTT

1501 AGGCTTCCCG CCTTGGGGAA GACGCAAAAG ACGGGCAAGC
     GCTCCACCAG

1551 CGCCGCGGTG CTGGAGGCCC TACGGGAGGC CCACCCCATC
     GTGGAGAAGA

1601 TCCTCCAGCA CCGGGAGCTC ACCAAGCTCA AGAACACCTA
     CGTGGACCCC

1651 CTCCCAAGCC TCGTCCACCC GAATACGGGC CGCCTCCACA
     CCCGCTTCAA

1701 CCAGACGGCC ACGGCCACGG GGAGGCTTAG TAGCTCCGAC
     CCCAACCTGC

1751 AGAACATCCC CGTCCGCACC CCCTTGGGCC AGAGGATCCG
     CCGGGCCTTC

1801 GTGGCCGAGG CGGGTTGGGC GTTGGTGGCC CTGGACTATA
     GCCAGATAGA

1851 GCTCCGCGTC CTCGCCCACC TCTCCGGGGA CGAGAACCTG
     ATCAGGGTCT

1901 TCCAGGAGGG GAAGGACATC CACACCCAGA CCGCAAGCTG
     GATGTTCGGC

1951 GTCCCCCCGG AGGCCGTGGA TCCCCTGATG CGCCGGGCGG
     CCAAGACGGT

2001 GAACTTCGGC GTCCTCTACG GCATGTCCGC CCATAGGCTC
     TCCCAGGAGC

2051 TTGCCATCCC CTACGAGGAG GCGGTGGCCT TTATAGAGCG
     CTACTTCCAA

2101 AGCTTCCCCA AGGTGCGGGC CTGGATAGAA AAGACCCTGG
     AGGAGGGGAG

2151 GAAGCGGGGC TACGTGGAAA CCCTCTTCGG AAGAAGGCGC
     TACGTGCCCG

2201 ACCTCAACGC CCGGGTGAAG AGCGTCAGGG AGGCCGCGGA
     GCGCATGGCC

2251 TTCAACATGC CCGTCCAGGG CACCGCCGCC GACCTCATGA
     AGCTCGCCAT
```

```
2301  GGTGAAGCTC TTCCCCCGCC TCCGGGAGAT GGGGGCCCGC
      ATGCTCCTCC

2351  AGGTCCACGA CGAGCTCCTC CTGGAGGCCC CCCAAGCGCG
      GGCCGAGGAG

2401  GTGGCGGCTT TGGCCAAGGA GGCCATGGAG AAGGCCTATC
      CCCTCGCCGT

2451  GCCCCTGGAG GTGGAGGTGG GGATGGGGGA GGACTGGCTT
      TCCGCCAAGG

2501  GTTAG
```

In another embodiment, the invention provides nucleic acids encoding a wild type nucleic acid polymerase from *Thermus thermophilus*, strain RQ-1, having, for example, SEQ ID NO:2.

```
   1  ATGGAGGCGA TGCTTCCGCT CTTTGAACCC AAAGGCCGGG
      TCCTCCTGGT

51  GGACGGCCAC CACCTGGCCT ACCGCACCTT CTTCGCCCTG
      AAGGGCCTCA

101  CCACGAGCCG GGGCGAACCG GTGCAGGCGG TCTACGGCTT
      CGCCAAGAGC

151  CTCCTCAAGG CCCTGAAGGA GGACGGGTAC AAGGCCGTCT
      TCGTGGTCTT

201  TGACGCCAAG GCCCCCTCCT TCCGCCACGA GGCCTACGAG
      GCCTACAAGG

251  CGGGGAGGGC CCCGACCCCC GAGGACTTCC CCCGGCAGCT
      CGCCCTCATC

301  AAGGAGCTGG TGGACCTCTT GGGGTTTACT CGCCTCGAGG
      TCCCGGGCTT

351  TGAGGCGGAC GACGTCCTCG CCACCCTGGC CAAGAAGGCG
      GAAAAAGAAG

401  GGTACGAGGT GCGCATCCTC ACCGCCGACC GGGACCTCTA
      CCAGCTCGTC

451  TCCGACCGGG TCGCCGTCCT CCACCCCGAG GGCCACCTCA
      TCACCCCGGA

501  GTGGCTTTGG GAGAAGTACG GCCTCAGGCC GGAGCAGTGG
      GTGGACTTCC

551  GCGCCCTCGT AGGGGACCCC TCCGACAACC TCCCCGGGGT
      CAAGGGCATC

601  GGGGAGAAGA CCGCCCTCAA GCTCCTTAAG GAGTGGGGAA
      GCCTGGAAAA

651  CCTCCTCAAG AACCTGGACC GGGTGAAGCC GGAAAGCGTC
      CGGGAGAAGA

701  TCAAGGCCCA CCTGGAAGAC CTCAGGCTCT CCTTGGAGCT
      CTCCCGGGTG

751  CGCACCGACC TCCCCCTGGA GGTGGACCTC GCCCAGGGGC
      GGGAGCCCGA

801  CCGGGAAGGG CTTAGGGCCT TCCTGGAGAG GCTAGAGTTC
      GGCAGCCTCC

851  TCCACGAGTT CGGCCTCCTG GAGGCCCCCG CCCCCCTGGA
      GGAGGCCCCC

901  TGGCCCCCGC CGGAAGGGGC CTTCGTGGGC TTCGTCCTCT
      CCCGCCCCGA

951  GCCCATGTGG GCGGAGCTTA AAGCCCTGGC CGCCTGCAGG
      GACGGCCGGG

1001  TGCACCGGGC GGAGGACCCC TTGGCGGGGC TTAAGGACCT
      CAAGGAGGTC

1051  CGGGGCCTCC TCGCCAAGGA CCTCGCCGTT TTGGCCTCGA
      GGGAGGGGCT

1101  AGACCTCGTG CCCGGGACG ACCCCATGCT CCTCGCCTAC
      CTCCTGGACC

1151  CCTCCAACAC CACCCCCGAG GGGGTGGCGC GGCGCTACGG
      GGGGGAGTGG

1201  ACGGAGGACG CCGCCCAGCG GGCCCTCCTC TCGGAGAGGC
      TCCAGCAGAA

1251  CCTCCTTAAG CGCCTCCAGG GGGAGGAGAA GCTCCTCTGG
      CTCTACCACG

1301  AGGTGGAAAA GCCCCTCTCC CGGGTCCTGG CCCACATGGA
      GGCCACCGGG

1351  GTACGGCTGG ACGTGGCCTA CCTTCAGGCC CTTTCCCTGG
      AGCTTGCGGA

1401  GGAGATCCGC CGCCTCGAGG AGGAGGTCTT CCGCTTGGCG
      GGCCACCCCT

1451  TCAACCTCAA CTCCCGGGAC CAGCTGGAAA GGGTGCTCTT
      TGACGAGCTT

1501  AGGCTTCCCG CCTTGGGGAA GACGCAAAAG ACGGGCAAGC
      GCTCCACCAG

1551  CGCCGCGGTG CTGGAGGCCC TACGGGAGGC CCACCCCATC
      GTGGAGAAGA

1601  TCCTCCAGCA CCGGGAGCTC ACCAAGCTCA AGAACACCTA
      CGTGGACCCC

1651  CTCCCAAGCC TCGTCCACCC GAGGACGGGC CGCCTCCACA
      CCCGCTTCAA

1701  CCAGACGGCC ACGGCCACGG GGAGGCTTAG TAGCTCCGAC
      CCCAACCTGC

1751  AGAACATCCC CGTCCGCACC CCCTTGGGCC AGAGGATCCG
      CCGGGCCTTC

1801  GTAGCCGAGG CGGGATGGGC GTTGGTGGCC CTGGACTATA
      GCCAGATAGA

1851  GCTCCGCGTC CTCGCCCACC TCTCCGGGGA CGAGAACCTG
      ATCAGGGTCT

1901  TCCAGGAGGG GAAGGACATC CACACCCAGA CCGCAAGCTG
      GATGTTCGGT

1951  GTCCCCCCGG AGGCCGTGGA CCCCCTGATG CGCCGGGCGG
      CCAAGACGGT

2001  GAACTTCGGC GTCCTCTACG GCATGTCCGC CCACCGGCTC
      TCCCAGGAGC

2051  TTTCCATCCC CTACGAGGAG GCGGTGGCCT TTATAGAGCG
      CTACTTCCAA

2101  AGCTTCCCCA AGGTGCGGGC CTGGATAGAA AAGACCCTGG
      AGGAGGGGAG

2151  GAAGCGGGGC TACGTGGAAA CCCTCTTCGG AAGAAGGCGC
      TACGTGCCCG

2201  ACCTCAACGC CCGGGTGAAG AGCGTCAGGG AGGCCGCGGA
      GCGCATGGCC

2251  TTCAACATGC CGTCCAGGG CACCGCCGCC GACCTCATGA
      AGCTCGCCAT

2301  GGTGAAGCTC TTCCCCCGCC TCCGGGAGAT GGGGGCCCGC
      ATGCTCCTCC
```

-continued

```
2351 AGGTCCACGA CGAGCTCCTC CTGGAGGCCC CCCAAGCGCG
     GGCCGAGGAG

2401 GTGGCGGCTT TGGCCAAGGA GGCCATGGAG AAGGCCTATC
     CCCTCGCCGT

2451 ACCCCTGGAG GTGGAGGTGG GGATCGGGGA GGACTGGCTT
     TCCGCCAAGG

2501 GCTAG
```

In another embodiment, the invention provides nucleic acids encoding a wild type nucleic acid polymerase from *Thermus thermophilus*, strain 1b21, having, for example, SEQ ID NO:3.

```
   1 ATGGAGGCGA TGCTTCCGCT CTTTGAACCC AAAGGCCGGG
     TCCTCCTGGT

51 GGACGGCCAC CACCTGGCCT ACCGCACCTT CTTCGCCCTG
     AAGGGCCTCA

101 CCACGAGCCG GGGCGAACCG GTGCAGGCGG TCTACGGCTT
     CGCCAAGAGC

151 CTCCTCAAGG CCCTGAAGGA GGACGGGTAC AAGGCCGTCT
     TCGTGGTCTT

201 TGACGCCAAG GCCCCCTCCT TCCGCCACGA GGCCTACGAG
     GCCTACAAGG

251 CGGGGAGGGC CCCGACCCCC GAGGACTTCC CCCGGCAGCT
     CGCCCTCATC

301 AAGGAGCTGG TGGACCTCCT GGGGTTTACC CGCCTCGAGG
     TCCCCGGCTA

351 CGAGGCGGAC GACGTCCTCG CCACCCTGGC CAAGAAGGCG
     GAAAAGGAGG

401 GGTACGAGGT GCGCATCCTC ACCGCCGACC GCGACCTCTA
     CCAACTCGTC

451 TCCGACCGCG TCGCCGTCCT CCACCCCGAG GGCCACCTCA
     TCACCCCGGA

501 GTGGCTTTGG GAGAAGTACG GCCTCAAGCC GGAGCAGTGG
     GTGGACTTCC

551 GCGCCCTCGT GGGGGACCCC TCCGACAACC TCCCCGGGGT
     CAAGGGCATC

601 GGGGAGAAGA CCGCCCTCAA GCTCCTCAAG GAGTGGGGAA
     GCCTGGAAAA

651 CCTCCTCAAG AACCTGGACC GGGTAAAGCC AGAAAACGTC
     CGGGAGAAGA

701 TCAAGGCCCA CCTGGAAGAC CTCAGGCTTT CCTTGGAGCT
     CTCCCGGGTG

751 CGCACCGACC TCCCCCTGGA GGTGGACCTC GCCCAGGGGC
     GGGAGCCCGA

801 CCGGGAGGGG CTTAGGGCCT TCCTGGAGAG GCTGGAGTTC
     GGCAGCCTCC

851 TCCACGAGTT CGGCCTCCTG GAGGCCCCCG CCCCCCTGGA
     GGAGGCCCCC

901 TGGCCCCCGC CGGAAGGGGC CTTCGTGGGC TTCGTCCTCT
     CCCGCCCCGA

951 GCCCATGTGG GCGGAGCTTA AAGCCCTGGC CGCCTGCAGG
     GACGGCCGGG

1001 TGCACCGGGC AGCAGACCCC TTGGCGGGGC TAAAGGACCT
     CAAGGAGGTC

1051 CGGGGCCTCC TCGCCAAGGA CCTCGCCGTC TTGGCCTCGA
     GGGAGGGGCT

1101 AGACCTCGTG CCCGGGACG ACCCCATGCT CCTCGCCTAC
     CTCCTGGACC

1151 CCTCCAACAC CACCCCCGAG GGGGTGGCGC GGCGCTACGG
     GGGGGAGTGG

1201 ACGGAGGACG CCGCCCACCG GGCCCTCCTC TCGGAGAGGC
     TCCATCGGAA

1251 CCTCCTTAAG CGCCTCGAGG GGGAGGAGAA GCTCCTTTGG
     CTCTACCACG

1301 AGGTGGAAAA GCCCCTCTCC CGGGTCCTGG CCCACATGGA
     GGCCACCGGG

1351 GTACGGCTGG ACGTGGCCTA CCTTCAGGCC CTTTCCCTGG
     AGCTTGCGGA

1401 GGAGATCCGC CGCCTCGAGG AGGAGGTCTT CCGCTTGGCG
     GGCCACCCCT

1451 TCAACCTCAA CTCCCGGGAC CAGCTGGAAA GGGTGCTCTT
     TGACGAGCTT

1501 AGGCTTCCCG CCTTGGGGAA GACGCAAAAG ACGGGCAAGC
     GCTCCACCAG

1551 CGCCGCGGTG CTGGAGGCCC TACGGGAGGC CCACCCCATC
     GTGGAGAAGA

1601 TCCTCCAGCA CCGGGAGCTC ACCAAGCTCA AGAACACCTA
     CGTGGACCCC

1651 CTCCCAAGCC TCGTCCACCC GAGGACGGGC CGCCTCCACA
     CCCGCTTCAA

1701 CCAGACGGCC ACGGCCACGG GGAGGCTTAG TAGCTCCGAC
     CCCAACCTGC

1751 AGAACATCCC CGTCCGCACC CCCTTGGGCC AGAGGATCCG
     CCGGGCCTTC

1801 GTGGCCGAGG CGGGATGGGC GTTGGTGGCC CTGGACTATA
     GCCAGATAGA

1851 GCTCCGCGTC CTCGCCCACC TCTCCGGGGA CGAGAACCTG
     ATCAGGGTCT

1901 TCCAGGAGGG GAAGGACATC CACACCCAGA CCGCAAGCTG
     GATGTTCGGC

1951 GTCCCCCCGG AGGCCGTGGA CCCCCTGATG CGCCGGGCGG
     CCAAGACGGT

2001 GAACTTCGGC GTCCTCTACG GCATGTCCGC CCATAGGCTC
     TCCCAGGAGC

2051 TTGCCATCCC CTACGAGGAG GCGGTGGCCT TTATAGAGCG
     CTACTTCCAA

2101 AGCTTCCCCA AGGTGCGGGC CTGGATAGAA AAGACCCTGG
     AGGAGGGGAG

2151 AAAGCGGGGC TACGTGGAAA CCCTCTTCGG AAGAAGGCGC
     TACGTGCCCG

2201 ACCTCAACGC CCGGGTGAAG AGCGTCAGGG AGGCCGCGGA
     GCGCATGGCC

2251 TTCAACATGC CCGTCCAGGG CACCGCCGCC GACCTCATGA
     AGCTCGCCAT

2301 GGTGAAGCTC TTCCCCCGCC TCCGGGAGAT GGGGGCCCGC
     ATGCTCCTCC

2351 AGGTCCACGA CGAGCTCCTC CTGGAGGCCC CCAAGCGCG
     GGCCGAGGAG
```

-continued

```
2401 GTGGCGGCTT TGGCCAAGGA GGCCATGGAG AAGGCCTATC
     CCCTCGCCGT
2451 GCCCCTGGAG GTGGAGGTGG GGATGGGGGA GGACTGGCTT
     TCCGCCAAGG
2501 GTTAG
```

In another embodiment, the invention provides a nucleic acid of SEQ ID NO:4, a derivative nucleic acid related to *Thermus thermophilus*, strain GK24, having GAC (encoding Asp) in place of GGC (encoding Gly) at positions 136-138. SEQ ID NO:4 is provided below.

```
   1 ATGGAGGCGA TGCTTCCGCT CTTTGAACCC AAAGGCCGGG TCCTCCTGGT
  51 GGACGGCCAC CACCTGGCCT ACCGCACCTT CTTCGCCCTG AAGGGCCTCA
 101 CCACGAGCCG GGGCGAACCG GTGCAGGCGG TCTACGACTT CGCCAAGAGC
 151 CTCCTCAAGG CCCTGAAGGA GGACGGGTAC AAGGCCGTCT TCGTGGTCTT
 201 TGACGCCAAG GCCCCCTCCT TCCGCCACGA GGCCTACGAG GCCTACAAGG
 251 CGGGGAGGGC CCCGACCCCC GAGGACTTCC CCCGGCAGCT CGCCCTCATC
 301 AAGGAGCTGG TGGACCTCCT GGGGTTTACC CGCCTCGAGG TCCCCGGCTA
 351 CGAGGCGGAC GACGTCCTCG CCACCCTGGC CAAGAAGGCG GAAAAGGAGG
 401 GGTACGAGGT GCGCATCCTC ACCGCCGACC GCGACCTCTA CCAACTCGTC
 451 TCCGACCGCG TCGCCGTCCT CCACCCCGAG GGCCACCTCA TCACCCCGGA
 501 GTGGCTTTGG CAGAAGTACG GCCTCAAGCC GGAGCAGTGG GTGGACTTCC
 551 GCGCCCTCGT GGGGGACCCC TCCGACAACC TCCCCGGGGT CAAGGGCATC
 601 GGGGAGAAGA CCGCCCTCAA GCTCCTCAAG GAGTGGGGAA GCCTGGAAAA
 651 CCTCCTCAAG AACCTGGACC GGGTAAAGCC AGAAAACGTC CGGGAGAAGA
 701 TCAAGGCCCA CCTGGAAGAC CTCAGGCTTT CCTTGGAGCT CTCCCGGGTG
 751 CGCACCGACC TCCCCCTGGA GGTGGACCTC GCCCAGGGGC GGGAGCCCGA
 801 CCGGGAGGGG CTTAGGGCCT TCCTGGAGAG GCTGGAGTTC GGCAGCCTCC
 851 TCCACGAGTT CGGCCTCCTG GAGGCCCCCG CCCCCCTGGA GGAGGCCCCC
 901 TGGCCCCCGC CGGAAGGGGC CTTCGTGGGC TTCGTCCTCT CCCGCCCCGA
 951 GCCCATGTGG GCGGAGCTTA AAGCCCTGGC CGCCTGCAGG GACGGCCGGG
1001 TGCACCGGGC AGCGGACCCC TTGGCGGGGC TAAAGGACCT CAAGGAGGTC
1051 CGGGGCCTCC TCGCCAAGGA CCTCGCCGTC TTGGCCTCGA GGGAGGGGCT
1101 AGACCTCGTG CCCGGGGACG ACCCCATGCT CCTCGCCTAC CTCCTGGACC
1151 CCTCCAACAC CACCCCCGAG GGGGTGGCGC GGCGCTACGG GGGGGAGTGG
1201 ACGGAGGACG CCGCCCACCG GGCCCTCCTC TCGGAGAGGC TCCATCGGAA
1251 CCTCCTTAAG CGCCTCCAGG GGGAGGAGAA GCTCCTTTGG CTCTACCACG
1301 AGGTGGAAAA GCCCCTCTCC CGGGTCCTGG CCCACATGGA GGCCACCGGG
1351 GTACGGCTGG ACGTGGCCTA CCTGCAGGCC CTTTCCCTGG AGCTTGCGGA
1401 GGAGATCCGC CGCCTCGAGG AGGAGGTCTT CCGCTTGGCG GGCCACCCCT
1451 TCAACCTCAA CTCCCGGGAC CAGCTGGAGA GGGTGCTCTT TGACGAGCTT
1501 AGGCTTCCCG CCTTGGGGAA GACGCAAAAG ACGGGCAAGC GCTCCACCAG
1551 CGCCGCGGTG CTGGAGGCCC TACGGGAGGC CCACCCCATC GTGGAGAAGA
1601 TCCTCCAGCA CCGGGAGCTC ACCAAGCTCA AGAACACCTA CGTGGACCCC
1651 CTCCCAAGCC TCGTCCACCC GAATACGGGC CGCCTCCACA CCCGCTTCAA
```

```
1701 CCAGACGGCC ACGGCCACGG GGAGGCTTAG TAGCTCCGAC CCCAACCTGC

1751 AGAACATCCC CGTCCGCACC CCCTTGGGCC AGAGGATCCG CCGGGCCTTC

1801 GTGGCCGAGG CGGGTTGGGC GTTGGTGGCC CTGGACTATA GCCAGATAGA

1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGC

1951 GTCCCCCCGG AGGCCGTGGA TCCCCTGATG CGCCGGGCGG CCAAGACGGT

2001 GAACTTCGGC GTCCTCTACG GCATGTCCGC CCATAGGCTC TCCCAGGAGC

2051 TTGCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 GAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

In another embodiment, the invention provides a nucleic acid of SEQ ID NO:5, a derivative nucleic acid related to *Thermus thermophilus*, strain RQ-1, having GAC (encoding Asp) in place of GGC (encoding Gly) at positions 136-138. SEQ ID NO:5 is provided below.

```
  1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGACTT CGCCAAGAGC

151 CTCCTCAAGG CCCTGAAGGA GGACGGGTAC AAGGCCGTCT TCGTGGTCTT

201 TGACGCCAAG GCCCCCTCCT TCCGCCACGA GGCCTACGAG GCCTACAAGG

251 CGGGGAGGGC CCCGACCCCC GAGGACTTCC CCCGGCAGCT CGCCCTCATC

301 AAGGAGCTGG TGGACCTCTT GGGGTTTACT CGCCTCGAGG TCCCGGGCTT

351 TGAGGCGGAC GACGTCCTCG CCACCCTGGC CAAGAAGGCG GAAAAGAAG

401 GGTACGAGGT GCGCATCCTC ACCGCCGACC GGGACCTCTA CCAGCTCGTC

451 TCCGACCGGG TCGCCGTCCT CCACCCCGAG GGCCACCTCA TCACCCCGGA

501 GTGGCTTTGG GAGAAGTACG GCCTCAGGCC GGAGCAGTGG GTGGACTTCC

551 GCGCCCTCGT AGGGGACCCC TCCGACAACC TCCCCGGGGT CAAGGGCATC

601 GGGGAGAAGA CCGCCCTCAA GCTCCTTAAG GAGTGGGGAA GCCTGGAAAA

651 CCTCCTCAAG AACCTGGACC GGGTGAAGCC GGAAAGCGTC CGGGAGAAGA

701 TCAAGGCCCA CCTGGAAGAC CTCAGGCTCT CCTTGGAGCT CTCCCGGGTG

751 CGCACCGACC TCCCCCTGGA GGTGGACCTC GCCCAGGGGC GGGAGCCCGA

801 CCGGGAAGGG CTTAGGGCCT TCCTGGAGAG GCTAGAGTTC GGCAGCCTCC

851 TCCACGAGTT CGGCCTCCTG GAGGCCCCCG CCCCCCTGGA GGAGGCCCCC

901 TGGCCCCCGC CGGAAGGGGC CTTCGTGGGC TTCGTCCTCT CCCGCCCCGA
```

```
 951 GCCCATGTGG GCGGAGCTTA AAGCCCTGGC CGCCTGCAGG GACGGCCGGG

1001 TGCACCGGGC GGAGGACCCC TTGGCGGGGC TTAAGGACCT CAAGGAGGTC

1051 CGGGGCCTCC TCGCCAAGGA CCTCGCCGTT TTGGCCTCGA GGGAGGGGCT

1101 AGACCTCGTG CCCGGGGACG ACCCCATGCT CCTCGCCTAC CTCCTGGACC

1151 CCTCCAACAC CACCCCCGAG GGGGTGGCGC GGCGCTACGG GGGGGAGTGG

1201 ACGGAGGACG CCGCCCAGCG GGCCCTCCTC TCGGAGAGGC TCCAGCAGAA

1251 CCTCCTTAAG CGCCTCCAGG GGGAGGAGAA GCTCCTCTGG CTCTACCACG

1301 AGGTGGAAAA GCCCCTCTCC CGGGTCCTGG CCCACATGGA GGCCACCGGG

1351 GTACGGCTGG ACGTGGCCTA CCTTCAGGCC CTTTCCCTGG AGCTTGCGGA

1401 GGAGATCCGC CGCCTCGAGG AGGAGGTCTT CCGCTTGGCG GGCCACCCCT

1451 TCAACCTCAA CTCCCGGGAC CAGCTGGAAA GGGTGCTCTT TGACGAGCTT

1501 AGGCTTCCCG CCTTGGGGAA GACGCAAAAG ACGGGCAAGC GCTCCACCAG

1551 CGCCGCGGTG CTGGAGGCCC TACGGGAGGC CCACCCCATC GTGGAGAAGA

1601 TCCTCCAGCA CCGGGAGCTC ACCAAGCTCA AGAACACCTA CGTGGACCCC

1651 CTCCCAAGCC TCGTCCACCC GAGGACGGGC CGCCTCCACA CCCGCTTCAA

1701 CCAGACGGCC ACGGCCACGG GGAGGCTTAG TAGCTCCGAC CCCAACCTGC

1751 AGAACATCCC CGTCCGCACC CCCTTGGGCC AGAGGATCCG CCGGGCCTTC

1801 GTAGCCGAGG CGGGATGGGC GTTGGTGGCC CTGGACTATA GCCAGATAGA

1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGT

1951 GTCCCCCCGG AGGCCGTGGA CCCCCTGATG CGCCGGGCGG CCAAGACGGT

2001 GAACTTCGGC GTCCTCTACG GCATGTCCGC CCACCGGCTC TCCCAGGAGC

2051 TTTCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 GAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 ACCCCTGGAG GTGGAGGTGG GGATCGGGGA GGACTGGCTT TCCGCCAAGG

2501 GCTAG
```

In another embodiment, the invention provides a nucleic acid of SEQ ID NO:6, a derivative nucleic acid related to *Thermus thermophilus*, strain 1b21, having GAC (encoding Asp) in place of GGC (encoding Gly) at positions 136-138. SEQ ID NO:6 is provided below

```
  1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGACTT CGCCAAGAGC

151 CTCCTCAAGG CCCTGAAGGA GGACGGGTAC AAGGCCGTCT TCGTGGTCTT
```

-continued

```
 201 TGACGCCAAG GCCCCCTCCT TCCGCCACGA GGCCTACGAG GCCTACAAGG
 251 CGGGGAGGGC CCCGACCCCC GAGGACTTCC CCCGGCAGCT CGCCCTCATC
 301 AAGGAGCTGG TGGACCTCCT GGGGTTTACC CGCCTCGAGG TCCCCGGCTA
 351 CGAGGCGGAC GACGTCCTCG CCACCCTGGC CAAGAAGGCG GAAAAGGAGG
 401 GGTACGAGGT GCGCATCCTC ACCGCCGACC GCGACCTCTA CCAACTCGTC
 451 TCCGACCGCG TCGCCGTCCT CCACCCCGAG GCCACCTCA TCACCCCGGA
 501 GTGGCTTTGG GAGAAGTACG GCCTCAAGCC GGAGCAGTGG GTGGACTTCC
 551 GCGCCCTCGT GGGGGACCCC TCCGACAACC TCCCCGGGGT CAAGGGCATC
 601 GGGGAGAAGA CCGCCCTCAA GCTCCTCAAG GAGTGGGGAA GCCTGGAAAA
 651 CCTCCTCAAG AACCTGGACC GGGTAAAGCC AGAAAACGTC CGGGAGAAGA
 701 TCAAGGCCCA CCTGGAAGAC CTCAGGCTTT CCTTGGAGCT CTCCCGGGTG
 751 CGCACCGACC TCCCCCTGGA GGTGGACCTC GCCCAGGGGC GGGAGCCCGA
 801 CCGGGAGGGG CTTAGGGCCT TCCTGGAGAG GCTGGAGTTC GGCAGCCTCC
 851 TCCACGAGTT CGGCCTCCTG GAGGCCCCCG CCCCCCTGGA GGAGGCCCCC
 901 TGGCCCCCGC CGGAAGGGGC CTTCGTGGGC TTCGTCCTCT CCCGCCCCGA
 951 GCCCATGTGG GCGGAGCTTA AGCCCTGGC CGCCTGCAGG GACGGCCGGG
1001 TGCACCGGGC AGCAGACCCC TTGGCGGGGC TAAAGGACCT CAAGGAGGTC
1051 CGGGGCCTCC TCGCCAAGGA CCTCGCCGTC TTGGCCTCGA GGGAGGGGCT
1101 AGACCTCGTG CCCGGGACG ACCCCATGCT CCTCGCCTAC CTCCTGGACC
1151 CCTCCAACAC CACCCCCGAG GGGGTGGCGC GGCGCTACGG GGGGGAGTGG
1201 ACGGAGGACG CCGCCCACCG GGCCCTCCTC TCGGAGAGGC TCCATCGGAA
1251 CCTCCTTAAG CGCCTCGAGG GGGAGGAGAA GCTCCTTTGG CTCTACCACG
1301 AGGTGGAAAA GCCCCTCTCC CGGGTCCTGG CCCACATGGA GGCCACCGGG
1351 GTACGGCTGG ACGTGGCCTA CCTTCAGGCC CTTTCCCTGG AGCTTGCGGA
1401 GGAGATCCGC CGCCTCGAGG AGGAGGTCTT CCGCTTGGCG GGCCACCCCT
1451 TCAACCTCAA CTCCCGGGAC CAGCTGGAAA GGGTGCTCTT TGACGAGCTT
1501 AGGCTTCCCG CCTTGGGGAA GACGCAAAAG ACGGGCAAGC GCTCCACCAG
1551 CGCCGCGGTG CTGGAGGCCC TACGGGAGGC CCACCCCATC GTGGAGAAGA
1601 TCCTCCAGCA CCGGGAGCTC ACCAAGCTCA AGAACACCTA CGTGGACCCC
1651 CTCCCAAGCC TCGTCCACCC GAGGACGGGC CGCCTCCACA CCCGCTTCAA
1701 CCAGACGGCC ACGGCCACGG GGAGGCTTAG TAGCTCCGAC CCCAACCTGC
1751 AGAACATCCC CGTCCGCACC CCCTTGGGCC AGAGGATCCG CCGGGCCTTC
1801 GTGGCCGAGG CGGGATGGGC GTTGGTGGCC CTGGACTATA GCCAGATAGA
1851 GCTCCGCGTC CTCGCCCACC TCTCCGGGGA CGAGAACCTG ATCAGGGTCT
1901 TCCAGGAGGG GAAGGACATC CACACCCAGA CCGCAAGCTG GATGTTCGGC
1951 GTCCCCCCGG AGGCCGTGGA CCCCCTGATG CGCCGGGCGG CCAAGACGGT
2001 GAACTTCGGC GTCCTCTACG GCATGTCCGC CCATAGGCTC TCCCAGGAGC
2051 TTGCCATCCC CTACGAGGAG GCGGTGGCCT TTATAGAGCG CTACTTCCAA
2101 AGCTTCCCCA AGGTGCGGGC CTGGATAGAA AAGACCCTGG AGGAGGGGAG
2151 AAAGCGGGGC TACGTGGAAA CCCTCTTCGG AAGAAGGCGC TACGTGCCCG
```

```
-continued
2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

In another embodiment, the invention provides a nucleic acid of SEQ ID NO:7, a derivative nucleic acid related to *Thermus thermophilus*, strain GK24, having TAC (encoding Tyr) in place of TTC (encoding Phe) at positions 2005-07. SEQ ID NO:7 is provided below:

```
   1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGGCTT CGCCAAGAGC

151 CTCCTCAAGG CCCTGAAGGA GGACGGGTAC AAGGCCGTCT TCGTGGTCTT

201 TGACGCCAAG GCCCCCTCCT TCCGCCACGA GGCCTACGAG GCCTACAAGG

251 CGGGGAGGGC CCCGACCCCC GAGGACTTCC CCCGGCAGCT CGCCCTCATC

301 AAGGAGCTGG TGGACCTCCT GGGGTTTACC CGCCTCGAGG TCCCCGGCTA

351 CGAGGCGGAC GACGTCCTCG CCACCCTGGC CAAGAAGGCG GAAAAGGAGG

401 GGTACGAGGT GCGCATCCTC ACCGCCGACC GCGACCTCTA CCAACTCGTC

451 TCCGACCGCG TCGCCGTCCT CCACCCCGAG GGCCACCTCA TCACCCCGGA

501 GTGGCTTTGG CAGAAGTACG GCCTCAAGCC GGAGCAGTGG GTGGACTTCC

551 GCGCCCTCGT GGGGGACCCC TCCGACAACC TCCCCGGGGT CAAGGGCATC

601 GGGGAGAAGA CCGCCCTCAA GCTCCTCAAG GAGTGGGGAA GCCTGGAAAA

651 CCTCCTCAAG AACCTGGACC GGGTAAAGCC AGAAAACGTC CGGGAGAAGA

701 TCAAGGCCCA CCTGGAAGAC CTCAGGCTTT CCTTGGAGCT CTCCCGGGTG

751 CGCACCGACC TCCCCCTGGA GGTGGACCTC GCCCAGGGGC GGGAGCCCGA

801 CCGGGAGGGG CTTAGGGCCT TCCTGGAGAG GCTGGAGTTC GGCAGCCTCC

851 TCCACGAGTT CGGCCTCCTG GAGGCCCCCG CCCCCCTGGA GGAGGCCCCC

901 TGGCCCCCGC CGGAAGGGGC CTTCGTGGGC TTCGTCCTCT CCCGCCCCGA

951 GCCCATGTGG GCGGAGCTTA AAGCCCTGGC CGCCTGCAGG GACGGCCGGG

1001 TGCACCGGGC AGCGGACCCC TTGGCGGGGC TAAAGGACCT CAAGGAGGTC

1051 CGGGGCCTCC TCGCCAAGGA CCTCGCCGTC TTGGCCTCGA GGGAGGGGCT

1101 AGACCTCGTG CCCGGGGACG ACCCCATGCT CCTCGCCTAC CTCCTGGACC

1151 CCTCCAACAC CACCCCCGAG GGGGTGGCGC GGCGCTACGG GGGGGAGTGG

1201 ACGGAGGACG CCGCCCACCG GGCCCTCCTC TCGGAGAGGC TCCATCGGAA

1251 CCTCCTTAAG CGCCTCCAGG GGGAGGAGAA GCTCCTTTGG CTCTACCACG

1301 AGGTGGAAAA GCCCCTCTCC CGGGTCCTGG CCCACATGGA GGCCACCGGG

1351 GTACGGCTGG ACGTGGCCTA CCTGCAGGCC CTTTCCCTGG AGCTTGCGGA

1401 GGAGATCCGC CGCCTCGAGG AGGAGGTCTT CCGCTTGGCG GGCCACCCCT
```

```
1451 TCAACCTCAA CTCCCGGGAC CAGCTGGAGA GGGTGCTCTT TGACGAGCTT

1501 AGGCTTCCCG CCTTGGGGAA GACGCAAAAG ACGGGCAAGC GCTCCACCAG

1551 CGCCGCGGTG CTGGAGGCCC TACGGGAGGC CCACCCCATC GTGGAGAAGA

1601 TCCTCCAGCA CCGGGAGCTC ACCAAGCTCA GAACACCTA CGTGGACCCC

1651 CTCCCAAGCC TCGTCCACCC GAATACGGGC CGCCTCCACA CCCGCTTCAA

1701 CCAGACGGCC ACGGCCACGG GGAGGCTTAG TAGCTCCGAC CCCAACCTGC

1751 AGAACATCCC CGTCCGCACC CCCTTGGGCC AGAGGATCCG CCGGGCCTTC

1801 GTGGCCGAGG CGGGTTGGGC GTTGGTGGCC CTGGACTATA GCCAGATAGA

1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGC

1951 GTCCCCCCGG AGGCCGTGGA TCCCCTGATG CGCCGGGCGG CCAAGACGGT

2001 GAACTACGGC GTCCTCTACG GCATGTCCGC CCATAGGCTC TCCCAGGAGC

2051 TTGCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 GAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

In another embodiment, the invention provides a nucleic acid of SEQ ID NO:8, a derivative nucleic acid related to *Thermus thermophilus*, strain RQ-1, having TAC (encoding Tyr) in place of TTC (encoding Phe) at positions 2005-07. SEQ ID NO:8 is provided below:

```
   1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGGCTT CGCCAAGAGC

151 CTCCTCAAGG CCCTGAAGGA GGACGGGTAC AAGGCCGTCT TCGTGGTCTT

201 TGACGCCAAG GCCCCCTCCT TCCGCCACGA GGCCTACGAG GCCTACAAGG

251 CGGGGAGGGC CCCGACCCCC GAGGACTTCC CCCGGCAGCT CGCCCTCATC

301 AAGGAGCTGG TGGACCTCTT GGGGTTTACT CGCCTCGAGG TCCCGGGCTT

351 TGAGGCGGAC GACGTCCTCG CCACCCTGGC CAAGAAGGCG GAAAAGGAAG

401 GGTACGAGGT GCGCATCCTC ACCGCCGACC GGGACCTCTA CCAGCTCGTC

451 TCCGACCGGG TCGCCGTCCT CCACCCCGAG GGCCACCTCA TCACCCCGGA

501 GTGGCTTTGG GAGAAGTACG GCCTCAGGCC GGAGCAGTGG GTGGACTTCC

551 GCGCCCTCGT AGGGGACCCC TCCGACAACC TCCCCGGGGT CAAGGGCATC

601 GGGGAGAAGA CCGCCCTCAA GCTCCTTAAG GAGTGGGGAA GCCTGGAAAA

651 CCTCCTCAAG AACCTGGACC GGGTGAAGCC GGAAAGCGTC CGGGAGAAGA
```

```
-continued
 701 TCAAGGCCCA CCTGGAAGAC CTCAGGCTCT CCTTGGAGCT CTCCCGGGTG
 751 CGCACCGACC TCCCCCTGGA GGTGGACCTC GCCCAGGGGC GGGAGCCCGA
 801 CCGGGAAGGG CTTAGGGCCT TCCTGGAGAG GCTAGAGTTC GGCAGCCTCC
 851 TCCACGAGTT CGGCCTCCTG GAGGCCCCCG CCCCCCTGGA GGAGGCCCCC
 901 TGGCCCCCGC CGGAAGGGGC CTTCGTGGGC TTCGTCCTCT CCCGCCCCGA
 951 GCCCATGTGG GCGGAGCTTA AAGCCCTGGC CGCCTGCAGG GACGGCCGGG
1001 TGCACCGGGC GGAGGACCCC TTGGCGGGGC TTAAGGACCT CAAGGAGGTC
1051 CGGGGCCTCC TCGCCAAGGA CCTCGCCGTT TTGGCCTCGA GGGAGGGGCT
1101 AGACCTCGTG CCCGGGGACG ACCCCATGCT CCTCGCCTAC CTCCTGGACC
1151 CCTCCAACAC CACCCCCGAG GGGGTGGCGC GGCGCTACGG GGGGGAGTGG
1201 ACGGAGGACG CCGCCCAGCG GGCCCTCCTC TCGGAGAGGC TCCAGCAGAA
1251 CCTCCTTAAG CGCCTCCAGG GGGAGGAGAA GCTCCTCTGG CTCTACCACG
1301 AGGTGGAAAA GCCCCTCTCC CGGGTCCTGG CCCACATGGA GGCCACCGGG
1351 GTACGGCTGG ACGTGGCCTA CCTTCAGGCC CTTTCCCTGG AGCTTGCGGA
1401 GGAGATCCGC CGCCTCGAGG AGGAGGTCTT CCGCTTGGCG GGCCACCCCT
1451 TCAACCTCAA CTCCCGGGAC CAGCTGGAAA GGGTGCTCTT TGACGAGCTT
1501 AGGCTTCCCG CCTTGGGGAA GACGCAAAAG ACGGGCAAGC GCTCCACCAG
1551 CGCCGCGGTG CTGGAGGCCC TACGGGAGGC CCACCCCATC GTGGAGAAGA
1601 TCCTCCAGCA CCGGGAGCTC ACCAAGCTCA AGAACACCTA CGTGGACCCC
1651 CTCCCAAGCC TCGTCCACCC GAGGACGGGC CGCCTCCACA CCCGCTTCAA
1701 CCAGACGGCC ACGGCCACGG GGAGGCTTAG TAGCTCCGAC CCCAACCTGC
1751 AGAACATCCC CGTCCGCACC CCCTTGGGCC AGAGGATCCG CCGGGCCTTC
1801 GTAGCCGAGG CGGGATGGGC GTTGGTGGCC CTGGACTATA GCCAGATAGA
1851 GCTCCGCGTC CTCGCCCACC TCTCCGGGGA CGAGAACCTG ATCAGGGTCT
1901 TCCAGGAGGG GAAGGACATC CACACCCAGA CCGCAAGCTG GATGTTCGGT
1951 GTCCCCCCGG AGGCCGTGGA CCCCCTGATG CGCGGGCGG CCAAGACGGT
2001 GAACTACGGC GTCCTCTACG GCATGTCCGC CCACCGGCTC TCCCAGGAGC
2051 TTTCCATCCC CTACGAGGAG GCGGTGGCCT TTATAGAGCG CTACTTCCAA
2101 AGCTTCCCCA AGGTGCGGGC CTGGATAGAA AAGACCCTGG AGGAGGGGAG
2151 GAAGCGGGGC TACGTGGAAA CCCTCTTCGG AAGAAGGCGC TACGTGCCCG
2201 ACCTCAACGC CCGGGTGAAG AGCGTCAGGG AGGCCGCGGA GCGCATGGCC
2251 TTCAACATGC CCGTCCAGGG CACCGCCGCC GACCTCATGA AGCTCGCCAT
2301 GGTGAAGCTC TTCCCCCGCC TCCGGGAGAT GGGGGCCCGC ATGCTCCTCC
2351 AGGTCCACGA CGAGCTCCTC CTGGAGGCCC CCCAAGCGCG GGCCGAGGAG
2401 GTGGCGGCTT TGGCCAAGGA GGCCATGGAG AAGGCCTATC CCCTCGCCGT
2451 ACCCCTGGAG GTGGAGGTGG GGATCGGGGA GGACTGGCTT TCCGCCAAGG
2501 GCTAG
```

In another embodiment, the invention provides a nucleic acid of SEQ ID NO:9, a derivative nucleic acid related to *Thermus thermophilus*, strain 1b21, having TAC (encoding Tyr) in place of TTC (encoding Phe) at positions 2005-07. SEQ ID NO:9 is provided below:

```
   1 ATGGAGGCGA TGCTTCCGCT CTTTGAACCC AAAGGCCGGG TCCTCCTGGT
  51 GGACGGCCAC CACCTGGCCT ACCGCACCTT CTTCGCCCTG AAGGGCCTCA
 101 CCACGAGCCG GGGCGAACCG GTGCAGGCGG TCTACGGCTT CGCCAAGAGC
 151 CTCCTCAAGG CCCTGAAGGA GGACGGGTAC AAGGCCGTCT TCGTGGTCTT
 201 TGACGCCAAG GCCCCCTCCT TCCGCCACGA GGCCTACGAG GCCTACAAGG
 251 CGGGGAGGGC CCCGACCCCC GAGGACTTCC CCGGCAGCT CGCCCTCATC
 301 AAGGAGCTGG TGGACCTCCT GGGGTTTACC CGCCTCGAGG TCCCCGGCTA
 351 CGAGGCGGAC GACGTCCTCG CCACCCTGGC CAAGAAGGCG GAAAAGGAGG
 401 GGTACGAGGT GCGCATCCTC ACCGCCGACC GCGACCTCTA CCAACTCGTC
 451 TCCGACCGCG TCGCCGTCCT CCACCCCGAG GGCCACCTCA TCACCCCGGA
 501 GTGGCTTTGG GAGAAGTACG GCCTCAAGCC GGAGCAGTGG GTGGACTTCC
 551 GCGCCCTCGT GGGGGACCCC TCCGACAACC TCCCCGGGGT CAAGGGCATC
 601 GGGGAGAAGA CCGCCCTCAA GCTCCTCAAG GAGTGGGGAA GCCTGGAAAA
 651 CCTCCTCAAG AACCTGGACC GGGTAAAGCC AGAAAACGTC CGGGAGAAGA
 701 TCAAGGCCCA CCTGGAAGAC CTCAGGCTTT CCTTGGAGCT CTCCCGGGTG
 751 CGCACCGACC TCCCCCTGGA GGTGGACCTC GCCCAGGGGC GGGAGCCCGA
 801 CCGGGAGGGG CTTAGGGCCT TCCTGGAGAG GCTGGAGTTC GGCAGCCTCC
 851 TCCACGAGTT CGGCCTCCTG GAGGCCCCCG CCCCCCTGGA GGAGGCCCCC
 901 TGGCCCCCGC CGGAAGGGGC CTTCGTGGGC TTCGTCCTCT CCCGCCCCGA
 951 GCCCATGTGG GCGGAGCTTA AGCCCTGGC CGCCTGCAGG GACGGCCGGG
1001 TGCACCGGGC AGCAGACCCC TTGGCGGGGC TAAAGGACCT CAAGGAGGTC
1051 CGGGGCCTCC TCGCCAAGGA CCTCGCCGTC TTGGCCTCGA GGGAGGGGCT
1101 AGACCTCGTG CCCGGGGACG ACCCCATGCT CCTCGCCTAC CTCCTGGACC
1151 CCTCCAACAC CACCCCCGAG GGGGTGGCGC GGCGCTACGG GGGGGAGTGG
1201 ACGGAGGACG CCGCCCACCG GGCCCTCCTC TCGGAGAGGC TCCATCGGAA
1251 CCTCCTTAAG CGCCTCGAGG GGGAGGAGAA GCTCCTTTGG CTCTACCACG
1301 AGGTGGAAAA GCCCCTCTCC CGGGTCCTGG CCCACATGGA GGCCACCGGG
1351 GTACGGCTGG ACGTGGCCTA CCTTCAGGCC CTTTCCCTGG AGCTTGCGGA
1401 GGAGATCCGC CGCCTCGAGG AGGAGGTCTT CCGCTTGGCG GGCCACCCCT
1451 TCAACCTCAA CTCCCGGGAC CAGCTGGAAA GGGTGCTCTT TGACGAGCTT
1501 AGGCTTCCCG CCTTGGGGAA GACGCAAAAG ACGGGCAAGC GCTCCACCAG
1551 CGCCGCGGTG CTGGAGGCCC TACGGGAGGC CCACCCCATC GTGGAGAAGA
1601 TCCTCCAGCA CCGGGAGCTC ACCAAGCTCA AGAACACCTA CGTGGACCCC
1651 CTCCCAAGCC TCGTCCACCC GAGGACGGGC CGCCTCCACA CCCGCTTCAA
1701 CCAGACGGCC ACGGCCACGG GGAGGCTTAG TAGCTCCGAC CCCAACCTGC
1751 AGAACATCCC CGTCCGCACC CCCTTGGGCC AGAGGATCCG CCGGGCCTTC
1801 GTGGCCGAGG CGGGATGGGC GTTGGTGGCC CTGGACTATA GCCAGATAGA
```

```
1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGC

1951 GTCCCCCCGG AGGCCGTGGA CCCCCTGATG CGCCGGGCGG CCAAGACGGT

2001 GAACTACGGC GTCCTCTACG GCATGTCCGC CCATAGGCTC TCCCAGGAGC

2051 TTGCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 AAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

In another embodiment, the invention provides a nucleic acid of SEQ ID NO:10, a derivative nucleic acid related to *Thermus thermophilus*, strain GK24, having GAC (encoding Asp) in place of GGC (encoding Gly) at positions 136-138, and having TAC (encoding Tyr) in place of TTC (encoding Phe) at positions 2005-07. SEQ ID NO:10 is provided below:

```
   1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGACTT CGCCAAGAGC

151 CTCCTCAAGG CCCTGAAGGA GGACGGGTAC AAGGCCGTCT TCGTGGTCTT

201 TGACGCCAAG GCCCCCTCCT TCCGCCACGA GGCCTACGAG GCCTACAAGG

251 CGGGGAGGGC CCCGACCCCC GAGGACTTCC CCCGGCAGCT CGCCCTCATC

301 AAGGAGCTGG TGGACCTCCT GGGGTTTACC CGCCTCGAGG TCCCCGGCTA

351 CGAGGCGGAC GACGTCCTCG CCACCCTGGC CAAGAAGGCG GAAAAGGAGG

401 GGTACGAGGT GCGCATCCTC ACCGCCGACC GCGACCTCTA CCAACTCGTC

451 TCCGACCGCG TCGCCGTCCT CCACCCCGAG GGCCACCTCA TCACCCCGGA

501 GTGGCTTTGG CAGAAGTACG GCCTCAAGCC GGAGCAGTGG GTGGACTTCC

551 GCGCCCTCGT GGGGGACCCC TCCGACAACC TCCCCGGGGT CAAGGGCATC

601 GGGGAGAAGA CCGCCCTCAA GCTCCTCAAG GAGTGGGGAA GCCTGGAAAA

651 CCTCCTCAAG AACCTGGACC GGGTAAAGCC AGAAAACGTC CGGGAGAAGA

701 TCAAGGCCCA CCTGGAAGAC CTCAGGCTTT CCTTGGAGCT CTCCCGGGTG

751 CGCACCGACC TCCCCCTGGA GGTGGACCTC GCCCAGGGGC GGGAGCCCGA

801 CCGGGAGGGG CTTAGGGCCT TCCTGGAGAG GCTGGAGTTC GGCAGCCTCC

851 TCCACGAGTT CGGCCTCCTG GAGGCCCCCG CCCCCCTGGA GGAGGCCCCC

901 TGGCCCCCGC CGGAAGGGGC CTTCGTGGGC TTCGTCCTCT CCCGCCCCGA

951 GCCCATGTGG GCGGAGCTTA AAGCCCTGGC CGCCTGCAGG GACGGCCGGG

1001 TGCACCGGGC AGCGGACCCC TTGGCGGGGC TAAAGGACCT CAAGGAGGTC

1051 CGGGGCCTCC TCGCCAAGGA CCTCGCCGTC TTGGCCTCGA GGGAGGGGCT
```

-continued

```
1101 AGACCTCGTG CCCGGGGACG ACCCCATGCT CCTCGCCTAC CTCCTGGACC

1151 CCTCCAACAC CACCCCCGAG GGGGTGGCGC GGCGCTACGG GGGGGAGTGG

1201 ACGGAGGACG CCGCCCACCG GGCCCTCCTC TCGGAGAGGC TCCATCGGAA

1251 CCTCCTTAAG CGCCTCCAGG GGGAGGAGAA GCTCCTTTGG CTCTACCACG

1301 AGGTGGAAAA GCCCCTCTCC CGGGTCCTGG CCCACATGGA GGCCACCGGG

1351 GTACGGCTGG ACGTGGCCTA CCTGCAGGCC CTTTCCCTGG AGCTTGCGGA

1401 GGAGATCCGC CGCCTCGAGG AGGAGGTCTT CCGCTTGGCG GGCCACCCCT

1451 TCAACCTCAA CTCCCGGGAC CAGCTGGAGA GGGTGCTCTT TGACGAGCTT

1501 AGGCTTCCCG CCTTGGGGAA GACGCAAAAG ACGGGCAAGC GCTCCACCAG

1551 CGCCGCGGTG CTGGAGGCCC TACGGGAGGC CCACCCCATC GTGGAGAAGA

1601 TCCTCCAGCA CCGGGAGCTC ACCAAGCTCA AGAACACCTA CGTGGACCCC

1651 CTCCCAAGCC TCGTCCACCC GAATACGGGC CGCCTCCACA CCCGCTTCAA

1701 CCAGACGGCC ACGGCCACGG GGAGGCTTAG TAGCTCCGAC CCCAACCTGC

1751 AGAACATCCC CGTCCGCACC CCCTTGGGCC AGAGGATCCG CCGGGCCTTC

1801 GTGGCCGAGG CGGGTTGGGC GTTGGTGGCC CTGGACTATA GCCAGATAGA

1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGC

1951 GTCCCCCCGG AGGCCGTGGA TCCCCTGATG CGCCGGGCGG CCAAGACGGT

2001 GAACTACGGC GTCCTCTACG GCATGTCCGC CCATAGGCTC TCCCAGGAGC

2051 TTGCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 GAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

In another embodiment, the invention provides a nucleic acid of SEQ ID NO:11, a derivative nucleic acid related to *Thermus thermophilus*, strain RQ-1, having GAC (encoding Asp) in place of GGC (encoding Gly) at positions 136-138, and having TAC (encoding Tyr) in place of TTC (encoding Phe) at positions 2005-07. SEQ ID NO:11 is provided below:

```
  1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGACTT CGCCAAGAGC

151 CTCCTCAAGG CCCTGAAGGA GGACGGGTAC AAGGCCGTCT TCGTGGTCTT

201 TGACGCCAAG GCCCCTCCT TCCGCCACGA GGCCTACGAG GCCTACAAGG

251 CGGGGAGGGC CCCGACCCCC GAGGACTTCC CCCGGCAGCT CGCCCTCATC
```

-continued

```
 301 AAGGAGCTGG TGGACCTCTT GGGGTTTACT CGCCTCGAGG TCCCGGGCTT
 351 TGAGGCGGAC GACGTCCTCG CCACCCTGGC AAGAAGGCG  GAAAAAGAAG
 401 GGTACGAGGT GCGCATCCTC ACCGCCGACC GGGACCTCTA CCAGCTCGTC
 451 TCCGACCGGG TCGCCGTCCT CCACCCCGAG GGCCACCTCA TCACCCCGGA
 501 GTGGCTTTGG GAGAAGTACG GCCTCAGGCC GGAGCAGTGG GTGGACTTCC
 551 GCGCCCTCGT AGGGGACCCC TCCGACAACC TCCCCGGGGT CAAGGGCATC
 601 GGGGAGAAGA CCGCCCTCAA GCTCCTTAAG GAGTGGGGAA GCCTGGAAAA
 651 CCTCCTCAAG AACCTGGACC GGGTGAAGCC GGAAAGCGTC CGGGAGAAGA
 701 TCAAGGCCCA CCTGGAAGAC CTCAGGCTCT CCTTGGAGCT CTCCCGGGTG
 751 CGCACCGACC TCCCCCTGGA GGTGGACCTC GCCCAGGGGC GGGAGCCCGA
 801 CCGGGAAGGG CTTAGGGCCT TCCTGGAGAG GCTAGAGTTC GGCAGCCTCC
 851 TCCACGAGTT CGGCCTCCTG GAGGCCCCCG CCCCCCTGGA GGAGGCCCCC
 901 TGGCCCCCGC CGGAAGGGGC CTTCGTGGGC TTCGTCCTCT CCCGCCCCGA
 951 GCCCATGTGG GCGGAGCTTA AGCCCTGGCC CGCCTGCAGG GACGGCCGGG
1001 TGCACCGGGC GGAGGACCCC TTGGCGGGGC TTAAGGACCT CAAGGAGGTC
1051 CGGGGCCTCC TCGCCAAGGA CCTCGCCGTT TTGGCCTCGA GGGAGGGGCT
1101 AGACCTCGTG CCCGGGACG  ACCCCATGCT CCTCGCCTAC CTCCTGGACC
1151 CCTCCAACAC CACCCCCGAG GGGGTGGCGC GGCGCTACGG GGGGGAGTGG
1201 ACGGAGGACG CCGCCCAGCG GGCCCTCCTC TCGGAGAGGC TCCAGCAGAA
1251 CCTCCTTAAG CGCCTCCAGG GGGAGGAGAA GCTCCTCTGG CTCTACCACG
1301 AGGTGGAAAA GCCCCTCTCC CGGGTCCTGG CCCACATGGA GGCCACCGGG
1351 GTACGGCTGG ACGTGGCCTA CCTTCAGGCC CTTTCCCTGG AGCTTGCGGA
1401 GGAGATCCGC CGCCTCGAGG AGGAGGTCTT CCGCTTGGCG GGCCACCCCT
1451 TCAACCTCAA CTCCCGGGAC CAGCTGGAAA GGGTGCTCTT TGACGAGCTT
1501 AGGCTTCCCG CCTTGGGGAA GACGCAAAAG ACGGGCAAGC GCTCCACCAG
1551 CGCCGCGGTG CTGGAGGCCC TACGGGAGGC CCACCCCATC GTGGAGAAGA
1601 TCCTCCAGCA CCGGGAGCTC ACCAAGCTCA AGAACACCTA CGTGGACCCC
1651 CTCCCAAGCC TCGTCCACCC GAGGACGGGC CGCCTCCACA CCCGCTTCAA
1701 CCAGACGGCC ACGGCCACGG GGAGGCTTAG TAGCTCCGAC CCCAACCTGC
1751 AGAACATCCC CGTCCGCACC CCCTTGGGCC AGAGGATCCG CCGGGCCTTC
1801 GTAGCCGAGG CGGGATGGGC GTTGGTGGCC CTGGACTATA GCCAGATAGA
1851 GCTCCGCGTC CTCGCCCACC TCTCCGGGGA CGAGAACCTG ATCAGGGTCT
1901 TCCAGGAGGG GAAGGACATC CACACCCAGA CCGCAAGCTG GATGTTCGGT
1951 GTCCCCCCGG AGGCCGTGGA CCCCCTGATG CGCCGGGCGG CCAAGACGGT
2001 GAACTACGGC GTCCTCTACG GCATGTCCGC CCACCGGCTC TCCCAGGAGC
2051 TTTCCATCCC CTACGAGGAG GCGGTGGCCT TTATAGAGCG CTACTTCCAA
2101 AGCTTCCCCA AGGTGCGGGC CTGGATAGAA AAGACCCTGG AGGAGGGGAG
2151 GAAGCGGGGC TACGTGGAAA CCCTCTTCGG AAGAAGGCGC TACGTGCCCG
2201 ACCTCAACGC CCGGGTGAAG AGCGTCAGGG AGGCCGCGGA GCGCATGGCC
2251 TTCAACATGC CCGTCCAGGG CACCGCCGCC GACCTCATGA AGCTCGCCAT
2301 GGTGAAGCTC TTCCCCCGCC TCCGGGAGAT GGGGGCCCGC ATGCTCCTCC
```

In another embodiment, the invention provides a nucleic acid of SEQ ID NO:12, a derivative nucleic acid related to *Thermus thermophilus*, strain 1b21, having GAC (encoding Asp) in place of GGC (encoding Gly) at positions 136-138, and having TAC (encoding Tyr) in place of TTC (encoding Phe) at positions 2005-07. SEQ ID NO:12 is provided below:

```
2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 ACCCCTGGAG GTGGAGGTGG GGATCGGGGA GGACTGGCTT TCCGCCAAGG

2501 GCTAG
```

```
   1 ATGGAGGCGA TGCTTCCGCT CTTTGAACCC AAAGGCCGGG TCCTCCTGGT

51 GGACGGCCAC CACCTGGCCT ACCGCACCTT CTTCGCCCTG AAGGGCCTCA

101 CCACGAGCCG GGGCGAACCG GTGCAGGCGG TCTACGACTT CGCCAAGAGC

151 CTCCTCAAGG CCCTGAAGGA GGACGGGTAC AAGGCCGTCT TCGTGGTCTT

201 TGACGCCAAG GCCCCCTCCT TCCGCCACGA GGCCTACGAG GCCTACAAGG

251 CGGGGAGGGC CCCGACCCCC GAGGACTTCC CCCGGCAGCT CGCCCTCATC

301 AAGGAGCTGG TGGACCTCCT GGGGTTTACC CGCCTCGAGG TCCCCGGCTA

351 CGAGGCGGAC GACGTCCTCG CCACCCTGGC CAAGAAGGCG GAAAAGGAGG

401 GGTACGAGGT GCGCATCCTC ACCGCCGACC GCGACCTCTA CCAACTCGTC

451 TCCGACCGCG TCGCCGTCCT CCACCCCGAG GGCCACCTCA TCACCCCGGA

501 GTGGCTTTGG GAGAAGTACG GCCTCAAGCC GGAGCAGTGG GTGGACTTCC

551 GCGCCCTCGT GGGGGACCCC TCCGACAACC TCCCCGGGGT CAAGGGCATC

601 GGGGAGAAGA CCGCCCTCAA GCTCCTCAAG GAGTGGGGAA GCCTGGAAAA

651 CCTCCTCAAG AACCTGGACC GGGTAAAGCC AGAAAACGTC CGGGAGAAGA

701 TCAAGGCCCA CCTGGAAGAC CTCAGGCTTT CCTTGGAGCT CTCCCGGGTG

751 CGCACCGACC TCCCCCTGGA GGTGGACCTC GCCCAGGGGC GGGAGCCCGA

801 CCGGGAGGGG CTTAGGGCCT TCCTGGAGAG GCTGGAGTTC GGCAGCCTCC

851 TCCACGAGTT CGGCCTCCTG GAGGCCCCCG CCCCCCTGGA GGAGGCCCCC

901 TGGCCCCCGC CGGAAGGGGC CTTCGTGGGC TTCGTCCTCT CCCGCCCCGA

951 GCCCATGTGG GCGGAGCTTA AAGCCCTGGC CGCCTGCAGG GACGGCCGGG

1001 TGCACCGGGC AGCAGACCCC TTGGCGGGGC TAAAGGACCT CAAGGAGGTC

1051 CGGGGCCTCC TCGCCAAGGA CCTCGCCGTC TTGGCCTCGA GGGAGGGGCT

1101 AGACCTCGTG CCCGGGGACG ACCCCATGCT CCTCGCCTAC CTCCTGGACC

1151 CCTCCAACAC CACCCCCGAG GGGGTGGCGC GGCGCTACGG GGGGGAGTGG

1201 ACGGAGGACG CCGCCCACCG GGCCCTCCTC TCGGAGAGGC TCCATCGGAA

1251 CCTCCTTAAG CGCCTCGAGG GGGAGGAGAA GCTCCTTTGG CTCTACCACG

1301 AGGTGGAAAA GCCCCTCTCC CGGGTCCTGG CCCACATGGA GGCCACCGGG

1351 GTACGGCTGG ACGTGGCCTA CCTTCAGGCC CTTTCCCTGG AGCTTGCGGA

1401 GGAGATCCGC CGCCTCGAGG AGGAGGTCTT CCGCTTGGCG GGCCACCCCT

1451 TCAACCTCAA CTCCCGGGAC CAGCTGGAAA GGGTGCTCTT TGACGAGCTT

1501 AGGCTTCCCG CCTTGGGGAA GACGCAAAAG ACGGGCAAGC GCTCCACCAG
```

```
1551 CGCCGCGGTG CTGGAGGCCC TACGGGAGGC CCACCCCATC GTGGAGAAGA

1601 TCCTCCAGCA CCGGGAGCTC ACCAAGCTCA AGAACACCTA CGTGGACCCC

1651 CTCCCAAGCC TCGTCCACCC GAGGACGGGC CGCCTCCACA CCCGCTTCAA

1701 CCAGACGGCC ACGGCCACGG GGAGGCTTAG TAGCTCCGAC CCCAACCTGC

1751 AGAACATCCC CGTCCGCACC CCCTTGGGCC AGAGGATCCG CCGGGCCTTC

1801 GTGGCCGAGG CGGGATGGGC GTTGGTGGCC CTGGACTATA GCCAGATAGA

1851 GCTCCGCGTC CTCGCCCACC TCTCCGGGGA CGAGAACCTG ATCAGGGTCT

1901 TCCAGGAGGG GAAGGACATC CACACCCAGA CCGCAAGCTG GATGTTCGGC

1951 GTCCCCCCGG AGGCCGTGGA CCCCCTGATG CGCCGGGCGG CCAAGACGGT

2001 GAACTACGGC GTCCTCTACG GCATGTCCGC CCATAGGCTC TCCCAGGAGC

2051 TTGCCATCCC CTACGAGGAG GCGGTGGCCT TTATAGAGCG CTACTTCCAA

2101 AGCTTCCCCA AGGTGCGGGC CTGGATAGAA AAGACCCTGG AGGAGGGGAG

2151 AAAGCGGGGC TACGTGGAAA CCCTCTTCGG AAGAAGGCGC TACGTGCCCG

2201 ACCTCAACGC CCGGGTGAAG AGCGTCAGGG AGGCCGCGGA GCGCATGGCC

2251 TTCAACATGC CCGTCCAGGG CACCGCCGCC GACCTCATGA AGCTCGCCAT

2301 GGTGAAGCTC TTCCCCCGCC TCCGGGAGAT GGGGGCCCGC ATGCTCCTCC

2351 AGGTCCACGA CGAGCTCCTC CTGGAGGCCC CCCAAGCGCG GGCCGAGGAG

2401 GTGGCGGCTT TGGCCAAGGA GGCCATGGAG AAGGCCTATC CCCTCGCCGT

2451 GCCCCTGGAG GTGGAGGTGG GGATGGGGGA GGACTGGCTT TCCGCCAAGG

2501 GTTAG
```

The substitution of TAC (encoding Tyr) for TTC (encoding Phe) at the indicated positions can reduce discrimination against ddNTP incorporation by DNA polymerase I. See, e.g., U.S. Pat. No. 5,614,365 that is incorporated herein by reference. The substitution of GAC (encoding Asp) for GGG (encoding Gly) at the indicated positions removes the 5'-3' exonuclease activity.

The nucleic acids of the invention have homology to portions of the nucleic acids encoding the thermostable DNA polymerases of *Thermus thermophilus* (see FIGS. 1 and 2). However, significant portions of the nucleic acid sequences of the present invention are distinct.

The invention also encompasses fragment and variant nucleic acids of SEQ ID NO:1-12. Nucleic acid "fragments" encompassed by the invention are of two general types. First, fragment nucleic acids that do not encode a full-length nucleic acid polymerase but do encode a thermally stable polypeptide with nucleic acid polymerase activity are encompassed within the invention. Second, fragment nucleic acids useful as hybridization probes but that generally do not encode polymerases retaining biological activity are also encompassed within the invention. Thus, fragments of nucleotide sequences such as SEQ ID NO:1-12 may be as small as about 9 nucleotides, about 12 nucleotides, about 15 nucleotides, about 17 nucleotides, about 18 nucleotides, about 20 nucleotides, about 50 nucleotides, about 100 nucleotides or more. In general, a fragment nucleic acid of the invention can have any upper size limit so long as it is related in sequence to the nucleic acids of the invention but is not full length.

As indicated above, "variants" are substantially similar or substantially homologous sequences. For nucleotide sequences, variants include those sequences that, because of the degeneracy of the genetic code, encode the identical amino acid sequence of the native nucleic acid polymerase protein. Variant nucleic acids also include those that encode polypeptides that do not have amino acid sequences identical to that of a native nucleic acid polymerase protein, but that encode an active, thermally stable nucleic acid polymerase with conservative changes in the amino acid sequence.

As is known by one of skill in the art, the genetic code is "degenerate," meaning that several trinucleotide codons can encode the same amino acid. This degeneracy is apparent from Table 1.

TABLE 1

| 1st Position | Second Position | | | | 3rd Position |
|---|---|---|---|---|---|
| | T | C | A | G | |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid. Therefore, a particular nucleic acid sequence of the invention also encompasses variants with degenerate codon substitutions, and complementary sequences thereof, as well as the sequence explicitly specified by a SEQ ID NO. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., Nucleic Acid Res., 19, 5081 (1991) and/or Ohtsuka et al., J. Biol. Chem., 260, 2605 (1985); Rossolini et al., Mol. Cell. Probes, 8, 91 (1994).

However, the invention is not limited to silent changes in the present nucleotide sequences but also includes variant nucleic acid sequences that conservatively alter the amino acid sequence of a polypeptide of the invention. According to the present invention, variant and reference nucleic acids of the invention may differ in the encoded amino acid sequence by one or more substitutions, additions, insertions, deletions, fusions and truncations, which may be present in any combination, so long as an active, thermally stable nucleic acid polymerase is encoded by the variant nucleic acid. Such variant nucleic acids will not encode exactly the same amino acid sequence as the reference nucleic acid, but have conservative sequence changes.

Variant nucleic acids with silent and conservative changes can be defined and characterized by the degree of homology to the reference nucleic acid. Preferred variant nucleic acids are "substantially homologous" to the reference nucleic acids of the invention. As recognized by one of skill in the art, such substantially similar nucleic acids can hybridize under stringent conditions with the reference nucleic acids identified by SEQ ID NOs herein. These types of substantially homologous nucleic acids are encompassed by this invention.

Generally, nucleic acid derivatives and variants of the invention will have at least 90%, 91%, 92%, 93% or 94% sequence identity to the reference nucleotide sequence defined herein. Preferably, nucleic acids of the invention will have at least at least 95%, 96%, 97%, 98%, or 99% sequence identity to the reference nucleotide sequence defined herein.

Variant nucleic acids can be detected and isolated by standard hybridization procedures.

Hybridization to detect or isolate such sequences is generally carried out under stringent conditions. "Stringent hybridization conditions" and "stringent hybridization wash conditions" in the context of nucleic acid hybridization experiments such as Southern and Northern hybridization are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, N.Y. (1993). See also, J. Sambrook et al., Molecular Cloning: A Laboratory Manual, Cold Spring Harbor Press, N.Y., pp 9.31-9.58 (1989); J. Sambrook et al., Molecular Cloning: A Laboratory Manual, Cold Spring Harbor Press, N.Y. (3rd ed. 2001).

The invention also provides methods for detection and isolation of derivative or variant nucleic acids encoding nucleic acid polymerase activity. The methods involve hybridizing at least a portion of a nucleic acid comprising any one of SEQ ID NO:1-12 to a sample nucleic acid, thereby forming a hybridization complex; and detecting the hybridization complex. The presence of the complex correlates with the presence of a derivative or variant nucleic acid encoding at least a segment of nucleic acid polymerase. In general, the portion of a nucleic acid comprising any one of SEQ ID NO:1-12 used for hybridization is at least fifteen nucleotides, and hybridization is under hybridization conditions that are sufficiently stringent to permit detection and isolation of substantially homologous nucleic acids. In an alternative embodiment, a nucleic acid sample is amplified by the polymerase chain reaction using primer oligonucleotides selected from any one of SEQ ID NO:1-12.

Generally, highly stringent hybridization and wash conditions are selected to be about 5 C lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions, nucleic acids that are 100% complementary can be identified.

Alternatively, stringency conditions can be adjusted to allow some mismatching in sequences so that lower degrees of similarity are detected (heterologous probing). Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ can be approximated from the equation of Meinkoth and Wahl Anal. Biochem. 138:267-284 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe.

An example of stringent hybridization conditions for hybridization of complementary nucleic acids that have more than 100 complementary residues on a filter in a Southern or Northern blot is 50% formamide with 1 mg of heparin at 42 C, with the hybridization being carried out overnight. An example of highly stringent conditions is 0.15 M NaCl at 72 C for about 15 minutes. An example of stringent wash conditions is a 0.2×SSC wash at 65 C for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45 C for 15 minutes. An example low stringency wash for a duplex of, e.g., more than 100 nucleotides, is 4-6×SSC at 40 C for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30 C.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence preferably hybridizes to the reference nucleotide sequence in 7% sodium dodecyl sulfate (SDS), 0.5 M NaPO$_4$, 1 mM EDTA at 50 C with washing in 2×SSC, 0.1% SDS at 50 C, more desirably in 7% sodium dodecyl sulfate (SDS), 0.5 M NaPO$_4$, 1 mM EDTA at 50 C with washing in 1×SSC, 0.1% SDS at 50 C, more desirably still in 7% sodium dodecyl sulfate (SDS), 0.5 M NaPO$_4$, 1 mM EDTA at 50 C with washing in 0.5×SSC, 0.1% SDS at 50 C, preferably in 7% sodium dodecyl sulfate (SDS), 0.5 M NaPO$_4$, 1 mM EDTA at 50 C with washing in 0.1×SSC, 0.1% SDS at 50 C, more preferably in 7% sodium dodecyl sulfate (SDS), 0.5 M NaPO$_4$, 1 mM EDTA at 50 C with washing in 0.1×SSC, 0.1% SDS at 65 C.

In general, $T_m$ is reduced by about 1° C. for each 1% of mismatching. Thus, $T_m$, hybridization, and/or wash conditions can be adjusted to hybridize to sequences of the desired sequence identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, N.Y.); and Ausubel et al., eds. (1995) Current Protocols in Molecular Biology, Chapter 2 (Greene Publishing and Wiley—Interscience, New York). See Sambrook et al. (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present nucleic acid polymerase nucleic acids.

Computer analyses can also be utilized for comparison of sequences to determine sequence identity. Such analyses include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237 244 (1988); Higgins et al. CABIOS 5:151-153 (1989); Corpet et al. Nucleic Acids Res. 16:10881-90 (1988); Huang et al. CABIOS 8:155-65 (1992); and Pearson et al. Meth. Mol. Biol. 24:307-331 (1994). The ALIGN program is based on the algorithm of Myers and Miller, supra. The BLAST programs of Altschul et al., J. Mol. Biol. 215:403 (1990), are based on the algorithm of Karlin and Altschul supra. To obtain gapped alignments for comparison purposes, Gapped BLAST (in BLAST 2.0) can be utilized as described in Altschul et al. Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA, 89, 10915 (1989)). See http://www.ncbi.nlm.nih.gov. Alignment may also be performed manually by inspection.

For purposes of the present invention, comparison of nucleotide sequences for determination of percent sequence identity to the nucleic acid polymerase sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Expression of Nucleic Acids Encoding Polymerases

Nucleic acids of the invention may be used for the recombinant expression of the nucleic acid polymerase polypeptides of the invention. Generally, recombinant expression of a nucleic acid polymerase polypeptide of the invention is effected by introducing a nucleic acid encoding that polypeptide into an expression vector adapted for use in particular type of host cell. The nucleic acids of the invention can be introduced and expressed in any host organism, for example, in both prokaryotic or eukaryotic host cells. Examples of host cells include bacterial cells, yeast cells, cultured insect cell lines, and cultured mammalian cells lines. Preferably, the recombinant host cell system is selected that processes and post-translationally modifies nascent polypeptides in a manner similar to that of the organism from which the nucleic acid polymerase was derived. For purposes of expressing and isolating nucleic acid polymerase polypeptides of the invention, prokaryotic organisms are preferred, for example, *Escherichia coli*. Accordingly, the invention provides host cells comprising the expression vectors of the invention.

The nucleic acids to be introduced can be conveniently placed in expression cassettes for expression in an organism of interest. Such expression cassettes will comprise a transcriptional initiation region linked to a nucleic acid of the invention. Expression cassettes preferably also have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

Preferably the nucleic acid in the vector is under the control of, and operably linked to, an appropriate promoter or other regulatory elements for transcription in a host cell. The vector may be a bi-functional expression vector that functions in multiple hosts. The transcriptional cassette generally includes in the 5'-3' direction of transcription, a promoter, a transcriptional and translational initiation region, a DNA sequence of interest, and a transcriptional and translational termination region functional in the organism. The termination region may be native with the transcriptional initiation region, may be native with the DNA sequence of interest, or may be derived from another source.

Efficient expression of recombinant nucleic acids in prokaryotic and eukaryotic cells generally requires regulatory control elements directing the efficient termination and polyadenylation of the resulting transcript. Transcription termination signals are generally found downstream of the polyadenylation signal and are a few hundred nucleotides in length. The term "poly A site" or "poly A sequence" as used herein denotes a nucleic acid sequence that directs both the termination and polyadenylation of the nascent RNA transcript. Efficient polyadenylation of the recombinant transcript is desirable as transcripts lacking a poly A tail are unstable and are rapidly degraded.

Nucleic acids encoding nucleic acid polymerase may be introduced into bacterial host cells by a method known to one of skill in the art. For example, nucleic acids encoding a thermophilic nucleic acid polymerase can be introduced into bacterial cells by commonly used transformation procedures such as by treatment with calcium chloride or by electroporation. If the thermophilic nucleic acid polymerase is to be expressed in eukaryotic host cells, nucleic acids encoding the thermophilic nucleic acid polymerase may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

Thus, one aspect of the invention is to provide expression vectors and host cells comprising a nucleic acid encoding a nucleic acid polymerase polypeptide of the invention. A wide range of expression vectors are available in the art. Description of various expression vectors and how to use them can be found among other places in U.S. Pat. Nos. 5,604,118; 5,583,023; 5,432,082; 5,266,490; 5,063,158; 4,966,841; 4,806,472; 4,801,537; and Goedel et al., Gene Expression Technology, Methods of Enzymology, Vol. 185, Academic Press, San Diego (1989). The expression of nucleic acid polymerases in recombinant cell systems is a well-established technique. Examples of the recombinant expression of nucleic acid polymerase can be found in U.S. Pat. Nos. 5,602,756; 5,545,552; 5,541,311; 5,500,363; 5,489,523; 5,455,170; 5,352,778; 5,322,785; and 4,935,361.

Recombinant DNA and molecular cloning techniques that can be used to help make and use aspects of the invention are described by Sambrook et al., Molecular Cloning: A Laboratory Manual Vol. 1-3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

Nucleic Acid Polymerase Enzymes

The invention provides *Thermus thermophilus* nucleic acid polymerase polypeptides, as well as fragments thereof and variant nucleic acid Polymerase polypeptides that are active and thermally stable. Any polypeptide containing amino acid sequence having any one of SEQ ID NO:13-24, which are the amino acid sequences for wild type and derivative *Thermus thermophilus* nucleic acid polymerases, are contemplated by the present invention. The polypeptides of the invention are isolated or substantially purified polypeptides. In particular, the isolated polypeptides of the invention are substantially free of proteins normally present in *Thermus thermophilus* bacteria.

In one embodiment, the invention provides a polypeptide of SEQ ID NO:13, a wild type *Thermus thermophilus* nucleic acid polymerase polypeptide from strain GK24. SEQ ID NO:13 is provided below.

```
  1  MEAMLPLFEP  KGRVLLVDGH  HLAYRTFFAL  KGLTTSRGEP  VQAVYGFAKS   50

51  LLKALKEDGY  KAVFVVFDAK  APSFRHEAYE  AYKAGRAPTP  EDFPRQLALI  100

101  KELVDLLGFT  RLEVPGYEAD  DVLATLAKKA  EKEGYEVRIL  TADRDLYQLV  150

151  SDRVAVLHPE  GHLITPEWLW  QKYGLKPEQW  VDFRALVGDP  SDNLPGVKGI  200

201  GEKTALKLLK  EWGSLENLLK  NLDRVKPENV  REKIKAHLED  LRLSLELSRV  250

251  RTDLPLEVDL  AQGREPDREG  LRAFLERLEF  GSLLHEFGLL  EAPAPLEEAP  300

301  WPPPEGAFVG  FVLSRPEPMW  AELKALAACR  DGRVHRAADP  LAGLKDLKEV  350
```

```
351   RGLLAKDLAV  LASREGLDLV  PGDDPMLLAY  LLDPSNTTPE  GVARRYGGEW    400

401   TEDAAHRALL  SERLHRNLLK  RLQGEEKLLW  LYHEVEKPLS  RVLAHMEATG    450

451   VRLDVAYLQA  LSLELAEEIR  RLEEEVFRLA  GHPFNLNSRD  QLERVLFDEL    500

501   RLPALGKTQK  TGKRSTSAAV  LEALREAHPI  VEKILQHREL  TKLKNTYVDP    550

551   LPSLVHPNTG  RLHTRFNQTA  TATGRLSSSD  PNLQNIPVRT  PLGQRIRRAF    600

601   VAEAGWALVA  LDYSQIELRV  LAHLSGDENL  IRVFQEGKDI  HTQTASWMFG    650

651   VPPEAVDPLM  RRAAKTVNFG  VLYGMSAHRL  SQELAIPYEE  AVAFIERYFQ    700

701   SFPKVRAWIE  KTLEEGRKRG  YVETLFGRRR  YVPDLNARVK  SVREAAERMA    750

751   FNMPVQGTAA  DLMKLAMVKL  FPRLREMGAR  MLLQVHDELL  LEAPQARAEE    800

801   VAALAKEAME  KAYPLAVPLE  VEVGMGEDWL  SAKG                      834
```

In another embodiment, the invention provides SEQ ID NO:14 a wild type *Thermus thermophilus* nucleic acid polymerase enzyme, from strain RQ-1. SEQ ID NO:14 is provided below.

```
  1   MEAMLPLFEP  KGRVLLVDGH  HLAYRTFFAL  KGLTTSRGEP  VQAVYGFAKS     50

51   LLKALKEDGY  KAVFVVFDAK  APSFRHEAYE  AYKAGRAPTP  EDFPRQLALI    100

101   KELVDLLGFT  RLEVPGFEAD  DVLATLAKKA  EKEGYEVRIL  TADRDLYQLV    150

151   SDRVAVLHPE  GHLITPEWLW  EKYGLRPEQW  VDFRALVGDP  SDNLPGVKGI    200

201   GEKTALKLLK  EWGSLENLLK  NLDRVKPESV  REKIKAHLED  LRLSLELSRV    250

251   RTDLPLEVDL  AQGREPDREG  LRAFLERLEF  GSLLHEFGLL  EAPAPLEEAP    300

301   WPPPEGAFVG  FVLSRPEPMW  AELKALAACR  DGRVHRAEDP  LAGLKDLKEV    350

351   RGLLAKDLAV  LASREGLDLV  PGDDPMLLAY  LLDPSNTTPE  GVARRYGGEW    400

401   TEDAAQRALL  SERLQQNLLK  RLQGEEKLLW  LYHEVEKPLS  RVLAHMEATG    450

451   VRLDVAYLQA  LSLELAEEIR  RLEEEVFRLA  GHPFNLNSRD  QLERVLFDEL    500

501   RLPALGKTQK  TGKRSTSAAV  LEALREAHPI  VEKILQHREL  TKLKNTYVDP    550

551   LPSLVHPRTG  RLHTRFNQTA  TATGRLSSSD  PNLQNIPVRT  PLGQRIRRAF    600

601   VAEAGWALVA  LDYSQIELRV  LAHLSGDENL  IRVFQEGKDI  HTQTASWMFG    650

651   VPPEAVDPLM  RRAAKTVNFG  VLYGMSAHRL  SQELSIPYEE  AVAFIERYFQ    700

701   SFPKVRAWIE  KTLEEGRKRG  YVETLFGRRR  YVPDLNARVK  SVREAAERMA    750

751   FNMPVQGTAA  DLMKLAMVKL  FPRLREMGAR  MLLQVHDELL  LEAPQARAEE    800

801   VAALAKEAME  KAYPLAVPLE  VEVGIGEDWL  SAKG                      834
```

In another embodiment, the invention provides SEQ ID NO:15 a wild type *Thermus thermophilus* nucleic acid polymerase enzyme, from strain 1b21. SEQ ID NO:15 is provided below.

```
  1   MEAMLPLFEP  KGRVLLVDGH  HLAYRTFFAL  KGLTTSRGEP  VQAVYGFAKS     50

51   LLKALKEDGY  KAVFVVFDAK  APSFRHEAYE  AYKAGRAPTP  EDFPRQLALI    100

101   KELVDLLGFT  RLEVPGYEAD  DVLATLAKKA  EKEGYEVRIL  TADRDLYQLV    150

151   SDRVAVLHPE  GHLITPEWLW  EKYGLKPEQW  VDFRALVGDP  SDNLPGVKGI    200

201   GEKTALKLLK  EWGSLENLLK  NLDRVKPENV  REKIKAHLED  LRLSLELSRV    250

251   RTDLPLEVDL  AQGREPDREG  LRAFLERLEF  GSLLHEFGLL  EAPAPLEEAP    300
```

-continued

```
301  WPPPEGAFVG  FVLSRPEPMW  AELKALAACR  DGRVHRAADP  LAGLKDLKEV   351

351  RGLLAKDLAV  LASREGLDLV  PGDDPMLLAY  LLDPSNTTPE  GVARRYGGEW   400

401  TEDAAHRALL  SERLHRNLLK  RLEGEEKLLW  LYHEVEKPLS  RVLAHMEATG   450

451  VRLDVAYLQA  LSLELAEEIR  RLEEEVFRLA  GHPFNLNSRD  QLERVLFDEL   500

501  RLPALGKTQK  TGKRSTSAAV  LEALREAHPI  VEKILQHREL  TKLKNTYVDP   550

551  LPSLVHPRTG  RLHTRFNQTA  TATGRLSSSD  PNLQNIPVRT  PLGQRIRRAF   600

601  VAEAGWALVA  LDYSQIELRV  LAHLSGDENL  IRVFQEGKDI  HTQTASWMFG   650

651  VPPEAVDPLM  RRAAKTVNFG  VLYGMSAHRL  SQELAIPYEE  AVAFIERYFQ   700

701  SFPKVRAWIE  KTLEEGRKRG  YVETLFGRRR  YVPDLNARVK  SVREAAERMA   750

751  FNMPVQGTAA  DLMKLAMVKL  FPRLREMGAR  MLLQVHDELL  LEAPQARAEE   800

801  VAALAKEAME  KAYPLAVPLE  VEVGMGEDWL  SAKG                     834
```

The sequences of the wild type *Thermus thermophilus* nucleic acid polymerases of the invention are distinct from the amino acid sequence of known *Thermus thermophilus* DNA Polymerases. For example, comparison of the *Thermus thermophilus*, strain GK24 amino acid sequence (SEQ ID NO:13) with a published GK24 DNA Polymerase I sequence from Kwon et al., (Mol Cells. 1997 Apr. 30; 7 (2):264-71) reveals that SEQ ID NO:13 has four changes versus the Kwon sequence: Asn129→Lys, Pro130→Ala, Asp147→Tyr, and Gly797→Arg. These four positions are identified in FIG. 1. In each of these four positions, the Kwon GK24 DNA Polymerase I and a polypeptide with SEQ ID NO:13 have amino acids with dramatically different chemical properties. Asparagine (Kwon) at position 129 is a polar, uncharged amino acid side chain whereas lysine (SEQ ID NO:13) is charged and basic. Proline (Kwon) and alanine (SEQ ID NO:13) at position 130 are both aliphatic but alanine promotes helix or beta sheet formation whereas proline residues generally interrupt helices and sheets. Aspartate (Kwon) at position 147 is an acidic amino acid whereas tyrosine (SEQ ID NO:13) is aromatic. Glycine (Kwon) at position 797 is the smallest amino acid side chain whereas arginine (SEQ ID NO:13) has the longest, most basic charged side chain.

Similarly, comparison of the *Thermus thermophilus*, strain RQ-1 amino acid sequence (SEQ ID NO:14) with a published amino acid sequences for available strains of *Thermus thermophilus*, indicates that the *Thermus thermophilus*, strain RQ-1 amino acid sequence is distinct in at least two positions. At position 406, the *Thermus thermophilus*, strain RQ-1 amino acid sequence has glutamine, whereas the available *Thermus thermophilus* strains have histidine. At position 685, the *Thermus thermophilus*, strain RQ-1 amino acid sequence has serine, whereas the available *Thermus thermophilus* strains have alanine.

Moreover, comparison of the *Thermus thermophilus*, strain 1b21 amino acid sequence (SEQ ID NO:15) with a published amino acid sequences for available strains of *Thermus thermophilus*, indicates that the *Thermus thermophilus*, strain 1b21 amino acid sequence is distinct in at least one positions. At position 129, the *Thermus thermophilus*, strain 1b21 amino acid sequence has lysine, whereas the published amino acid sequence for *Thermus thermophilus* strain HB8 (ATCC accession number 466573) has arginine.

Hence, several regions of the *Thermus thermophilus* polymerases of the invention differ from previously available *Thermus thermophilus* DNA polymerases.

Many DNA polymerases possess activities in addition to a DNA polymerase activity. Such activities include, for example, a 5'-3' exonuclease activity and/or a 3'-5' exonuclease activity. The 3'-5' exonuclease activity improves the accuracy of the newly synthesized strand by removing incorrect bases that may have been incorporated. DNA polymerases in which such activity is low or absent are prone to errors in the incorporation of nucleotide residues into the primer extension strand. Taq DNA polymerase has been reported to have low 3'-5' exonuclease activity. See Lawyer et al., J. Biol Chem. 264:6427-6437. In applications such as nucleic acid amplification procedures in which the replication of DNA is often geometric in relation to the number of primer extension cycles, such errors can lead to serious artifactual problems such as sequence heterogeneity of the nucleic acid amplification product (amplicon). Thus, a 3'-5' exonuclease activity is a desired characteristic of a thermostable DNA polymerase used for such purposes.

By contrast, the 5'-3' exonuclease activity of DNA polymerase enzymes is often undesirable because this activity may digest nucleic acids, including primers, that have an unprotected 5' end. Thus, a thermostable nucleic acid polymerase with an attenuated 5'-3' exonuclease activity, or in which such activity is absent, is a desired characteristic of an enzyme for biochemical applications. Various DNA polymerase enzymes have been described where a modification has been introduced in a DNA polymerase that accomplishes this object. For example, the Klenow fragment of *E. coli* DNA polymerase I can be produced as a proteolytic fragment of the holoenzyme in which the domain of the protein controlling the 5'-3' exonuclease activity has been removed. The Klenow fragment still retains the polymerase activity and the 3'-5' exonuclease activity. Barnes, PCT Publication No. WO92/06188 (1992) and Gelfand et al., U.S. Pat. No. 5,079,352 have produced 5'-3' exonuclease-deficient recombinant *Thermus aquaticus* DNA polymerases. Ishino et al., EPO Publication No. 0517418A2, have produced a 5'-3' exonuclease-deficient DNA polymerase derived from *Bacillus caldotenax*.

In another embodiment, the invention provides a polypeptide that is a derivative *Thermus thermophilus* polypeptide with reduced or eliminated 5'-3' exonuclease activity. Several methods exist for reducing this activity, and the invention contemplates any polypeptide derived from the *Thermus thermophilus* polypeptides of the invention that has reduced or eliminated such 5'-3' exonuclease activity. See U.S. Pat. No. 5,466,591; Xu et al., *Biochemical and mutational studies of the 5'-3' exonuclease of DNA polymerase I of Escherichia coli*. J. Mol. Biol. 1997 May 2; 268(2):284-302.

In one embodiment, the invention provides a *Thermus thermophilus* nucleic acid polymerase polypeptide from strain GK24 in which Asp is used in place of Gly at position 46. This polypeptide has SEQ ID NO:16 and reduced 5'-3' exonuclease activity. SEQ ID NO:16 is provided below.

```
  1  MEAMLPLFEP KGRVLLVDGH HLAYRTFFAL KGLTTSRGEP VQAVYDFAKS   50
 51  LLKALKEDGY KAVFVVFDAK APSFRHEAYE AYKAGRAPTP EDFPRQLALI  100
101  KELVDLLGFT RLEVPGYEAD DVLATLAKKA EKEGYEVRIL TADRDLYQLV  150
151  SDRVAVLHPE GHLITPEWLW QKYGLKPEQW VDFRALVGDP SDNLPGVKGI  200
201  GEKTALKLLK EWGSLENLLK NLDRVKPENV REKIKAHLED LRLSLELSRV  250
251  RTDLPLEVDL AQGREPDREG LRAFLERLEF GSLLHEFGLL EAPAPLEEAP  300
301  WPPPEGAFVG FVLSRPEPMW AELKALAACR DGRVHRAADP LAGLKDLKEV  350
351  RGLLAKDLAV LASREGLDLV PGDDPMLLAY LLDPSNTTPE GVARRYGGEW  400
401  TEDAAHRALL SERLHRNLLK RLQGEEKLLW LYHEVEKPLS RVLAHMEATG  450
451  VRLDVAYLQA LSLELAEEIR RLEEEVFRLA GHPFNLNSRD QLERVLFDEL  500
501  RLPALGKTQK TGKRSTSAAV LEALREAHPI VEKILQHREL TKLKNTYVDP  550
551  LPSLVHPNTG RLHTRFNQTA TATGRLSSSD PNLQNIPVRT PLGQRIRRAF  600
601  VAEAGWALVA LDYSQIELRV LAHLSGDENL IRVFQEGKDI HTQTASWMFG  650
651  VPPEAVDPLM RRAAKTVNFG VLYGMSAHRL SQELAIPYEE AVAFIERYFQ  700
701  SFPKVRAWIE KTLEEGRKRG YVETLFGRRR YVPDLNARVK SVREAAERMA  750
751  FNMPVQGTAA DLMKLAMVKL FPRLREMGAR MLLQVHDELL LEAPQARAEE  800
801  VAALAKEAME KAYPLAVPLE VEVGMGEDWL SAKG                   834
```

In one embodiment, the invention provides a *Thermus thermophilus* nucleic acid polymerase polypeptide from strain RQ-1 in which Asp is used in place of Gly at position 46. This polypeptide has SEQ ID NO:17 and reduced 5'-3' exonuclease activity. SEQ ID NO:17 is provided below.

```
  1  MEAMLPLFEP KGRVLLVDGH HLAYRTFFAL KGLTTSRGEP VQAVYDFAKS   50
 51  LLKALKEDGY KAVFVVFDAK APSFRHEAYE AYKAGRAPTP EDFPRQLALI  100
101  KELVDLLGFT RLEVPGFEAD DVLATLAKKA EKEGYEVRIL TADRDLYQLV  150
151  SDRVAVLHPE GHLITPEWLW EKYGLRPEQW VDFRALVGDP SDNLPGVKGI  200
201  GEKTALKLLK EWGSLENLLK NLDRVKPESV REKIKAHLED LRLSLELSRV  250
251  RTDLPLEVDL AQGREPDREG LRAFLERLEF GSLLHEFGLL EAPAPLEEAP  300
301  WPPPEGAFVG FVLSRPEPMW AELKALAACR DGRVHRAEDP LAGLKDLKEV  350
351  RGLLAKDLAV LASREGLDLV PGDDPMLLAY LLDPSNTTPE GVARRYGGEW  400
401  TEDAAQRALL SERLQQNLLK RLQGEEKLLW LYHEVEKPLS RVLAHMEATG  450
451  VRLDVAYLQA LSLELAEEIR RLEEEVFRLA GHPFNLNSRD QLERVLFDEL  500
501  RLPALGKTQK TGKRSTSAAV LEALREAHPI VEKILQHREL TKLKNTYVDP  550
551  LPSLVHPRTG RLHTRFNQTA TATGRLSSSD PNLQNIPVRT PLGQRIRRAF  600
601  VAEAGWALVA LDYSQIELRV LAHLSGDENL IRVFQEGKDI HTQTASWMFG  650
651  VPPEAVDPLM RRAAKTVNFG VLYGMSAHRL SQELSIPYEE AVAFIERYFQ  700
701  SFPKVRAWIE KTLEEGRKRG YVETLFGRRR YVPDLNARVK SVREAAERMA  750
```

```
751   FNMPVQGTAA DLMKLAMVKL FPRLREMGAR MLLQVHDELL LEAPQARAEE    800

801   VAALAKEAME KAYPLAVPLE VEVGIGEDWL SAKG                    834
```

In another embodiment, the invention provides a *Thermus thermophilus* nucleic acid polymerase polypeptide from strain 1b21 in which Asp is used in place of Gly at position 46. This polypeptide has SEQ ID NO:18 and reduced 5'-3' exonuclease activity. SEQ ID NO:18 is provided below.

```
  1   MEAMLPLFEP KGRVLLVDGH HLAYRTFFAL KGLTTSRGEP VQAVYDFAKS     50

51   LLKALKEDGY KAVFVVFDAK APSFRHEAYE AYKAGRAPTP EDFPRQLALI    100

101   KELVDLLGFT RLEVPGYEAD DVLATLAKKA EKEGYEVRIL TADRDLYQLV    150

151   SDRVAVLHPE GHLITPEWLW EKYGLKPEQW VDFRALVGDP SDNLPGVKGI    200

201   GEKTALKLLK EWGSLENLLK NLDRVKPENV REKIKAHLED LRLSLELSRV    250

251   RTDLPLEVDL AQGREPDREG LRAFLERLEF GSLLHEFGLL EAPAPLEEAP    300

301   WPPPEGAFVG FVLSRPEPMW AELKALAACR DGRVHRAADP LAGLKDLKEV    351

351   RGLLAKDLAV LASREGLDLV PGDDPMLLAY LLDPSNTTPE GVARRYGGEW    400

401   TEDAAHRALL SERLHRNLLK RLEGEEKLLW LYHEVEKPLS RVLAHMEATG    450

451   VRLDVAYLQA LSLELAEEIR RLEEEVFRLA GHPFNLNSRD QLERVLFDEL    500

501   RLPALGKTQK TGKRSTSAAV LEALREAHPI VEKILQHREL TKLKNTYVDP    550

551   LPSLVHPRTG RLHTRFNQTA TATGRLSSSD PNLQNIPVRT PLGQRIRRAF    600

601   VAEAGWALVA LDYSQIELRV LAHLSGDENL IRVFQEGKDI HTQTASWMFG    650

651   VPPEAVDPLM RRAAKTVNFG VLYGMSAHRL SQELAIPYEE AVAFIERYFQ    700

701   SFPKVRAWIE KTLEEGRKRG YVETLFGRRR YVPDLNARVK SVREAAERMA    750

751   FNMPVQGTAA DLMKLAMVKL FPRLREMGAR MLLQVHDELL LEAPQARAEE    800

801   VAALAKEAME KAYPLAVPLE VEVGMGEDWL SAKG                    834
```

In another embodiment, the invention provides a polypeptide of SEQ ID NO:19, a derivative *Thermus thermophilus* polypeptide from strain GK24 with reduced bias against ddNTP incorporation. SEQ ID NO:19 has Tyr in place of Phe at position 669. The sequence of SEQ ID NO:19 is below.

```
  1   MEAMLPLFEP KGRVLLVDGH HLAYRTFFAL KGLTTSRGEP VQAVYGFAKS     50

51   LLKALKEDGY KAVFVVFDAK APSFRHEAYE AYKAGRAPTP EDFPRQLALI    100

101   KELVDLLGFT RLEVPGYEAD DVLATLAKKA EKEGYEVRIL TADRDLYQLV    150

151   SDRVAVLHPE GHLITPEWLW QKYGLKPEQW VDFRALVGDP SDNLPGVKGI    200

201   GEKTALKLLK EWGSLENLLK NLDRVKPENV REKIKAHLED LRLSLELSRV    250

251   RTDLPLEVDL AQGREPDREG LRAFLERLEF GSLLHEFGLL EAPAPLEEAP    300

301   WPPPEGAFVG FVLSRPEPMW AELKALAACR DGRVHRAADP LAGLKDLKEV    350

351   RGLLAKDLAV LASREGLDLV PGDDPMLLAY LLDPSNTTPE GVARRYGGEW    400

401   TEDAAHRALL SERLHRNLLK RLQGEEKLLW LYHEVEKPLS RVLAHMEATG    450

451   VRLDVAYLQA LSLELAEEIR RLEEEVFRLA GHPFNLNSRD QLERVLFDEL    500

501   RLPALGKTQK TGKRSTSAAV LEALREAHPI VEKILQHREL TKLKNTYVDP    550

551   LPSLVHPNTG RLHTRFNQTA TATGRLSSSD PNLQNIPVRT PLGQRIRRAF    600
```

-continued

```
601  VAEAGWALVA  LDYSQIELRV  LAHLSGDENL  IRVFQEGKDI  HTQTASWMFG   650
651  VPPEAVDPLM  RRAAKTVNYG  VLYGMSAHRL  SQELAIPYEE  AVAFIERYFQ   700
701  SFPKVRAWIE  KTLEEGRKRG  YVETLFGRRR  YVPDLNARVK  SVREAAERMA   750
751  FNMPVQGTAA  DLMKLAMVKL  FPRLREMGAR  MLLQVHDELL  LEAPQARAEE   800
801  VAALAKEAME  KAYPLAVPLE  VEVGMGEDWL  SAKG                     834
```

In another embodiment, the invention provides a polypeptide of SEQ ID NO:20, a derivative *Thermus thermophilus* polypeptide from strain RQ-1 with reduced bias against ddNTP incorporation. SEQ ID NO:20 has Tyr in place of Phe at position 669. The sequence of SEQ ID NO:20 is below.

```
  1  MEAMLPLFEP  KGRVLLVDGH  HLAYRTFFAL  KGLTTSRGEP  VQAVYGFAKS    50
 51  LLKALKEDGY  KAVFVVFDAK  APSFRHEAYE  AYKAGRAPTP  EDFPRQLALI   100
101  KELVDLLGFT  RLEVPGFEAD  DVLATLAKKA  EKEGYEVRIL  TADRDLYQLV   150
151  SDRVAVLHPE  GHLITPEWLW  EKYGLRPEQW  VDFRALVGDP  SDNLPGVKGI   200
201  GEKTALKLLK  EWGSLENLLK  NLDRVKPESV  REKIKAHLED  LRLSLELSRV   250
251  RTDLPLEVDL  AQGREPDREG  LRAFLERLEF  GSLLHEFGLL  EAPAPLEEAP   300
301  WPPPEGAFVG  FVLSRPEPMW  AELKALAACR  DGRVHRAEDP  LAGLKDLKEV   350
351  RGLLAKDLAV  LASREGLDLV  PGDDPMLLAY  LLDPSNTTPE  GVARRYGGEW   400
401  TEDAAQRALL  SERLQQNLLK  RLQGEEKLLW  LYHEVEKPLS  RVLAHMEATG   450
451  VRLDVAYLQA  LSLELAEEIR  RLEEEVFRLA  GHPFNLNSRD  QLERVLFDEL   500
501  RLPALGKTQK  TGKRSTSAAV  LEALREAHPI  VEKILQHREL  TKLKNTYVDP   550
551  LPSLVHPRTG  RLHTRFNQTA  TATGRLSSSD  PNLQNIPVRT  PLGQRIRRAF   600
601  VAEAGWALVA  LDYSQIELRV  LAHLSGDENL  IRVFQEGKDI  HTQTASWMFG   650
651  VPPEAVDPLM  RRAAKTVNYG  VLYGMSAHRL  SQELSIPYEE  AVAFIERYFQ   700
701  SFPKVRAWIE  KTLEEGRKRG  YVETLFGRRR  YVPDLNARVK  SVREAAERMA   750
751  FNMPVQGTAA  DLMKLAMVKL  FPRLREMGAR  MLLQVHDELL  LEAPQARAEE   800
801  VAALAKEAME  KAYPLAVPLE  VEVGIGEDWL  SAKG                     834
```

In another embodiment, the invention provides a polypeptide of SEQ ID NO:21, a derivative *Thermus thermophilus* polypeptide from strain 1b21 with reduced bias against ddNTP incorporation. SEQ ID NO:21 has Tyr in place of Phe at position 669. The sequence of SEQ ID NO:21 is below.

```
  1  MEAMLPLFEP  KGRVLLVDGH  HLAYRTFFAL  KGLTTSRGEP  VQAVYGFAKS    50
 51  LLKALKEDGY  KAVFVVFDAK  APSFRHEAYE  AYKAGRAPTP  EDFPRQLALI   100
101  KELVDLLGFT  RLEVPGYEAD  DVLATLAKKA  EKEGYEVRIL  TADRDLYQLV   150
151  SDRVAVLHPE  GHLITPEWLW  EKYGLKPEQW  VDFRALVGDP  SDNLPGVKGI   200
201  GEKTALKLLK  EWGSLENLLK  NLDRVKPENV  REKIKAHLED  LRLSLELSRV   250
251  RTDLPLEVDL  AQGREPDREG  LRAFLERLEF  GSLLHEFGLL  EAPAPLEEAP   300
301  WPPPEGAFVG  FVLSRPEPMW  AELKALAACR  DGRVHRAADP  LAGLKDLKEV   351
351  RGLLAKDLAV  LASREGLDLV  PGDDPMLLAY  LLDPSNTTPE  GVARRYGGEW   400
401  TEDAAHRALL  SERLHRNLLK  RLEGEEKLLW  LYHEVEKPLS  RVLAHMEATG   450
451  VRLDVAYLQA  LSLELAEEIR  RLEEEVFRLA  GHPFNLNSRD  QLERVLFDEL   500
```

```
501   RLPALGKTQK  TGKRSTSAAV  LEALREAHPI  VEKILQHREL  TKLKNTYVDP   550
551   LPSLVHPRTG  RLHTRFNQTA  TATGRLSSSD  PNLQNIPVRT  PLGQRIRRAF   600
601   VAEAGWALVA  LDYSQIELRV  LAHLSGDENL  IRVFQEGKDI  HTQTASWMFG   650
651   VPPEAVDPLM  RRAAKTVNYG  VLYGMSAHRL  SQELAIPYEE  AVAFIERYFQ   700
701   SFPKVRAWIE  KTLEEGRKRG  YVETLFGRRR  YVPDLNARVK  SVREAAERMA   750
751   FNMPVQGTAA  DLMKLAMVKL  FPRLREMGAR  MLLQVHDELL  LEAPQARAEE   800
801   VAALAKEAME  KAYPLAVPLE  VEVGMGEDWL  SAKG                     834
```

In another embodiment, the invention provides a polypeptide of SEQ ID NO:22, a derivative *Thermus thermophilus* polypeptide from strain GK24 with reduced 5'-3' exonuclease activity and reduced bias against ddNTP incorporation. SEQ ID NO:22 has Asp in place of Gly at position 46 and Tyr in place of Phe at position 669. The sequence of SEQ ID NO:22 is below.

```
  1   MEAMLPLFEP  KGRVLLVDGH  HLAYRTFFAL  KGLTTSRGEP  VQAVYDFAKS    50
 51   LLKALKEDGY  KAVFVVFDAK  APSFRHEAYE  AYKAGRAPTP  EDFPRQLALI   100
101   KELVDLLGFT  RLEVPGYEAD  DVLATLAKKA  EKEGYEVRIL  TADRDLYQLV   150
151   SDRVAVLHPE  GHLITPEWLW  QKYGLKPEQW  VDFRALVGDP  SDNLPGVKGI   200
201   GEKTALKLLK  EWGSLENLLK  NLDRVKPENV  REKIKAHLED  LRLSLELSRV   250
251   RTDLPLEVDL  AQGREPDREG  LRAFLERLEF  GSLLHEFGLL  EAPAPLEEAP   300
301   WPPPEGAFVG  FVLSRPEPMW  AELKALAACR  DGRVHRAADP  LAGLKDLKEV   350
351   RGLLAKDLAV  LASREGLDLV  PGDDPMLLAY  LLDPSNTTPE  GVARRYGGEW   400
401   TEDAAHRALL  SERLHRNLLK  RLQGEEKLLW  LYHEVEKPLS  RVLAHMEATG   450
451   VRLDVAYLQA  LSLELAEEIR  RLEEEVFRLA  GHPFNLNSRD  QLERVLFDEL   500
501   RLPALGKTQK  TGKRSTSAAV  LEALREAHPI  VEKILQHREL  TKLKNTYVDP   550
551   LPSLVHPNTG  RLHTRFNQTA  TATGRLSSSD  PNLQNIPVRT  PLGQRIRRAF   600
601   VAEAGWALVA  LDYSQIELRV  LAHLSGDENL  IRVFQEGKDI  HTQTASWMFG   650
651   VPPEAVDPLM  RRAAKTVNYG  VLYGMSAHRL  SQELAIPYEE  AVAFIERYFQ   700
701   SFPKVRAWIE  KTLEEGRKRG  YVETLFGRRR  YVPDLNARVK  SVREAAERMA   750
751   FNMPVQGTAA  DLMKLAMVKL  FPRLREMGAR  MLLQVHDELL  LEAPQARAEE   800
801   VAALAKEAME  KAYPLAVPLE  VEVGMGEDWL  SAKG                     834
```

In another embodiment, the invention provides a polypeptide of SEQ ID NO:23, a derivative *Thermus thermophilus* polypeptide from strain RQ-1 with reduced 5'-3' exonuclease activity and reduced bias against ddNTP incorporation. SEQ ID NO:23 has Asp in place of Gly at position 46 and Tyr in place of Phe at position 669. The sequence of SEQ ID NO:23 is below.

```
  1   MEAMLPLFEP  KGRVLLVDGH  HLAYRTFFAL  KGLTTSRGEP  VQAVYGFAKS    50
 51   LLKALKEDGY  KAVFVVFDAK  APSFRHEAYE  AYKAGRAPTP  EDFPRQLALI   100
101   KELVDLLGFT  RLEVPGFEAD  DVLATLAKKA  EKEGYEVRIL  TADRDLYQLV   150
151   SDRVAVLHPE  GHLITPEWLW  EKYGLRPEQW  VDFRALVGDP  SDNLPGVKGI   200
201   GEKTALKLLK  EWGSLENLLK  NLDRVKPESV  REKIKAHLED  LRLSLELSRV   250
```

```
251  RTDLPLEVDL  AQGREPDREG  LRAFLERLEF  GSLLHEFGLL  EAPAPLEEAP   300

301  WPPPEGAFVG  FVLSRPEPMW  AELKALAACR  DGRVHRAEDP  LAGLKDLKEV   350

351  RGLLAKDLAV  LASREGLDLV  PGDDPMLLAY  LLDPSNTTPE  GVARRYGGEW   400

401  TEDAAQRALL  SERLQQNLLK  RLQGEEKLLW  LYHEVEKPLS  RVLAHMEATG   450

451  VRLDVAYLQA  LSLELAEEIR  RLEEEVFRLA  GHPFNLNSRD  QLERVLFDEL   500

501  RLPALGKTQK  TGKRSTSAAV  LEALREAHPI  VEKILQHREL  TKLKNTYVDP   550

551  LPSLVHPRTG  RLHTRFNQTA  TATGRLSSSD  PNLQNIPVRT  PLGQRIRRAF   600

601  VAEAGWALVA  LDYSQIELRV  LAHLSGDENL  IRVFQEGKDI  HTQTASWMFG   650

651  VPPEAVDPLM  RRAAKTVNYG  VLYGMSAHRL  SQELSIPYEE  AVAFIERYFQ   700

701  SFPKVRAWIE  KTLEEGRKRG  YVETLFGRRR  YVPDLNARVK  SVREAAERMA   750

751  FNMPVQGTAA  DLMKLAMVKL  FPRLREMGAR  MLLQVHDELL  LEAPQARAEE   800

801  VAALAKEAME  KAYPLAVPLE  VEVGIGEDWL  SAKG                     834
```

In another embodiment, the invention provides a polypeptide of SEQ ID NO:24, a derivative *Thermus thermophilus* polypeptide from strain 1b21 with reduced 5'-3' exonuclease activity and reduced bias against ddNTP incorporation. SEQ ID NO:24 has Asp in place of Gly at position 46 and Tyr in place of Phe at position 669. The sequence of SEQ ID NO:24 is below.

```
  1  MEAMLPLFEP  KGRVLLVDGH  HLAYRTFFAL  KGLTTSRGEP  VQAVYDFAKS    50

51  LLKALKEDGY  KAVFVVFDAK  APSFRHEAYE  AYKAGRAPTP  EDFPRQLALI   100

101  KELVDLLGFT  RLEVPGYEAD  DVLATLAKKA  EKEGYEVRIL  TADRDLYQLV   150

151  SDRVAVLHPE  GHLITPEWLW  EKYGLKPEQW  VDFRALVGDP  SDNLPGVKGI   200

201  GEKTALKLLK  EWGSLENLLK  NLDRVKPENV  REKIKAHLED  LRLSLELSRV   250

251  RTDLPLEVDL  AQGREPDREG  LRAFLERLEF  GSLLHEFGLL  EAPAPLEEAP   300

301  WPPPEGAFVG  FVLSRPEPMW  AELKALAACR  DGRVHRAADP  LAGLKDLKEV   351

351  RGLLAKDLAV  LASREGLDLV  PGDDPMLLAY  LLDPSNTTPE  GVARRYGGEW   400

401  TEDAAHRALL  SERLHRNLLK  RLEGEEKLLW  LYHEVEKPLS  RVLAHMEATG   450

451  VRLDVAYLQA  LSLELAEEIR  RLEEEVFRLA  GHPFNLNSRD  QLERVLFDEL   500

501  RLPALGKTQK  TGKRSTSAAV  LEALREAHPI  VEKILQHREL  TKLKNTYVDP   550

551  LPSLVHPRTG  RLHTRFNQTA  TATGRLSSSD  PNLQNIPVRT  PLGQRIRRAF   600

601  VAEAGWALVA  LDYSQIELRV  LAHLSGDENL  IRVFQEGKDI  HTQTASWMFG   650

651  VPPEAVDPLM  RRAAKTVNYG  VLYGMSAHRL  SQELAIPYEE  AVAFIERYFQ   700

701  SFPKVRAWIE  KTLEEGRKRG  YVETLFGRRR  YVPDLNARVK  SVREAAERMA   750

751  FNMPVQGTAA  DLMKLAMVKL  FPRLREMGAR  MLLQVHDELL  LEAPQARAEE   800

801  VAALAKEAME  KAYPLAVPLE  VEVGMGEDWL  SAKG                     834
```

The nucleic acid polymerase polypeptides of the invention have homology to portions of the amino acid sequences of the thermostable DNA polymerases from other strains of *Thermus thermophilus*. However, several portions of the amino acid sequences of the present invention are distinct (see FIGS. 1 and 2).

As indicated above, derivative and variant polypeptides of the invention are derived from the wild type nucleic acid polymerase by deletion or addition of one or more amino acids to the N-terminal and/or C-terminal end of the wild type polypeptide; deletion or addition of one or more amino acids at one or more sites within the wild type polypeptide; or substitution of one or more amino acids at one or more sites within the wild type polypeptide. Thus, the polypeptides of the invention may be altered in various ways including amino acid substitutions, deletions, truncations, and insertions.

Such variant and derivative polypeptides may result, for example, from genetic polymorphism or from human manipulation. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82, 488 (1985); Kunkel et al., Methods in Enzymol., 154, 367 (1987); U.S. Pat. No. 4,873,192; Walker and Gaastra, eds., Techniques in Molecular Biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, C.D. (1978), herein incorporated by reference.

The derivatives and variants of the isolated polypeptides of the invention have identity with at least about 98% of the amino acid positions of any one of SEQ ID NO:13-24 and have nucleic acid polymerase activity and/or are thermally stable. In a preferred embodiment, polypeptide derivatives and variants have identity with at least about 99% of the amino acid positions of any one of SEQ ID NO:13-24 and have nucleic acid polymerase activity and/or are thermally stable.

Amino acid residues of the isolated polypeptides and polypeptide derivatives and variants can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 2.

TABLE 2

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| .-Alanine | | Bala |
| 2,3-Diaminopropionic acid | | Dpr |
| -Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |

TABLE 2-continued

| Amino Acid | One-Letter Symbol | Common Abbreviation |
|---|---|---|
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| .-2-thienylalanine | | Thi |
| Methionine sulfoxide | | MSO |
| Homoarginine | | Harg |
| N-acetyl lysine | | AcLys |
| 2,4-Diamino butyric acid | | Dbu |
| -Aminophenylalanine | | Phe(pNH$_2$) |
| N-methylvaline | | MeVal |
| Homocysteine | | Hcys |
| Homoserine | | Hser |
| .-Amino hexanoic acid | | Aha |
| .-Amino valeric acid | | Ava |
| 2,3-Diaminobutyric acid | | Dab |

Polypeptide variants that are encompassed within the scope of the invention can have one or more amino acids substituted with an amino acid of similar chemical and/or physical properties, so long as these variant polypeptides retain polymerase activity and/or remain thermally stable. Derivative polypeptides can have one or more amino acids substituted with amino acids having different chemical and/or physical properties, so long as these variant polypeptides retain polymerase activity and/or remain thermally stable.

Amino acids that are substitutable for each other in the present variant polypeptides generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, -2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a polypeptide.

Certain commonly encountered amino acids that are not genetically encoded and that can be present, or substituted for an amino acid, in the variant polypeptides of the invention include, but are not limited to, -alanine (b-Ala) and other omega-amino acids such as 3-aminopropionic acid (Dap), 2,3-diaminopropionic acid (Dpr), 4-aminobutyric acid and so forth; -aminoisobutyric acid (Aib); -aminohexanoic acid (Aha); -aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 3, below. It is to be understood that Table 3 is for illustrative purposes only and does not purport to be an exhaustive list of amino acid residues that may comprise the variant and derivative polypeptides described herein. Other amino acid residues that are useful for making the variant and derivative polypeptides described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 3

| Classification | Genetically Encoded | Genetically Non-Encoded |
|---|---|---|
| Hydrophobic | F, L, I, V | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | S, K | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, .-methyl Cys |

Polypeptides of the invention can have any amino acid substituted by any similarly classified amino acid to create a variant peptide, so long as the peptide variant is thermally stable and/or retains DNA Polymerase activity.

"Domain shuffling" or construction of "thermostable chimeric nucleic acid polymerases" may be used to provide thermostable polymerases containing novel properties. For example, placement of codons 289-422 from one of the present *Thermus thermophilus* polymerase coding sequences after codons 1-288 of the *Thermus aquaticus* DNA polymerase would yield a novel thermostable nucleic acid polymerase containing the 5'-3' exonuclease domain of *Thermus aquaticus* DNA polymerase (1-289), the 3'-5' exonuclease domain of *Thermus thermophilus* nucleic acid polymerase (289-422), and the DNA polymerase domain of *Thermus aquaticus* DNA polymerase (423-832). Alternatively, the 5'-3' exonuclease domain and the 3'-5' exonuclease domain of one of the present *Thermus thermophilus* nucleic acid polymerases may be fused to the DNA polymerase (dNTP binding and primer/template binding domains) portion of *Thermus aquaticus* DNA polymerase (about codons 423-832). The donors and recipients need not be limited to *Thermus aquaticus* and *Thermus thermophilus* polymerases. The *Thermus thermophilus* polymerase, 3'-5' exonuclease, 5'-3' exonuclease and/or other domains can similarly be exchanged for those from other species of *Thermus*.

It has been demonstrated that the exonuclease domain of *Thermus aquaticus* Polymerase I can be removed from the amino terminus of the protein with out a significant loss of thermostability or polymerase activity (Erlich et al., (1991) Science 252:1643-1651, Barnes, W. M., (1992) Gene 112:29-35., Lawyer et al., (1989) JBC 264:6427-6437). Other N-terminal deletions similarly have been shown to maintain thermostability and activity (Vainshtein et al., (1996) Protein Science 5:1785-1792 and references therein.) Therefore this invention also includes similarly truncated forms of any of the wild type or variant polymerases provided herein. For example, the invention is also directed to an active truncated variant of any of the polymerases provided by the invention in which the first 330 amino acids are removed.

Moreover, the invention provides SEQ ID NO:29, a truncated form of a polymerase in which the N-terminal 289 amino acids have been removed from the wild type *Thermus thermophilus* polymerase from strain GK24.

```
290                                          L EAPAPLEEAP    300
301   WPPPEGAFVG FVLSRPEPMW AELKALAACR DGRVHRAADP LAGLKDLKEV  350
351   RGLLAKDLAV LASREGLDLV PGDDPMLLAY LLDPSNTTPE GVARRYGGEW  400
401   TEDAAHRALL SERLHRNLLK RLQGEEKLLW LYHEVEKPLS RVLAHMEATG  450
451   VRLDVAYLQA LSLELAEEIR RLEEEVFRLA GHPFNLNSRD QLERVLFDEL  500
501   RLPALGKTQK TGKRSTSAAV LEALREAHPI VEKILQHREL TKLKNTYVDP  550
551   LPSLVHPNTG RLHTRFNQTA TATGRLSSSD PNLQNIPVRT PLGQRIRRAF  600
601   VAEAGWALVA LDYSQIELRV LAHLSGDENL IRVFQEGKDI HTQTASWMFG  650
651   VPPEAVDPLM RRAAKTVNFG VLYGMSAHRL SQELAIPYEE AVAFIERYFQ  700
701   SFPKVRAWIE KTLEEGRKRG YVETLFGRRR YVPDLNARVK SVREAAERMA  750
751   FNMPVQGTAA DLMKLAMVKL FPRLREMGAR MLLQVHDELL LEAPQARAEE  800
801   VAALAKEAME KAYPLAVPLE VEVGMGEDWL SAKG                   834
```

In another embodiment, the invention provides SEQ ID NO:30, a truncated form of a polymerase in which the N-terminal 289 amino acids have been removed from the wild type *Thermus thermophilus* polymerase from strain RQ-1. SEQ ID NO:30 is provided below.

```
290                                          L EAPAPLEEAP    300
301   WPPPEGAFVG FVLSRPEPMW AELKALAACR DGRVHRAEDP LAGLKDLKEV  350
351   RGLLAKDLAV LASREGLDLV PGDDPMLLAY LLDPSNTTPE GVARRYGGEW  400
401   TEDAAQRALL SERLQQNLLK RLQGEEKLLW LYHEVEKPLS RVLAHMEATG  450
451   VRLDVAYLQA LSLELAEEIR RLEEEVFRLA GHPFNLNSRD QLERVLFDEL  500
501   RLPALGKTQK TGKRSTSAAV LEALREAHPI VEKILQHREL TKLKNTYVDP  550
551   LPSLVHPRTG RLHTRFNQTA TATGRLSSSD PNLQNIPVRT PLGQRIRRAF  600
601   VAEAGWALVA LDYSQIELRV LAHLSGDENL IRVFQEGKDI HTQTASWMFG  650
651   VPPEAVDPLM RRAAKTVNFG VLYGMSAHRL SQELSIPYEE AVAFIERYFQ  700
701   SFPKVRAWIE KTLEEGRKRG YVETLFGRRR YVPDLNARVK SVREAAERMA  750
751   FNMPVQGTAA DLMKLAMVKL FPRLREMGAR MLLQVHDELL LEAPQARAEE  800
801   VAALAKEAME KAYPLAVPLE VEVGIGEDWL SAKG                   834
```

In another embodiment, the invention provides SEQ ID NO:30, a truncated form of a polymerase in which the N-terminal 289 amino acids have been removed from the wild type *Thermus thermophilus* polymerase from strain 1b21. SEQ ID NO:30 is provided below.

```
290                                          L EAPAPLEEAP    300
301   WPPPEGAFVG FVLSRPEPMW AELKALAACR DGRVHRAADP LAGLKDLKEV  351
```

```
351  RGLLAKDLAV  LASREGLDLV  PGDDPMLLAY  LLDPSNTTPE  GVARRYGGEW  400

401  TEDAAHRALL  SERLHRNLLK  RLEGEEKLLW  LYHEVEKPLS  RVLAHMEATG  450

451  VRLDVAYLQA  LSLELAEEIR  RLEEEVFRLA  GHPFNLNSRD  QLERVLFDEL  500

501  RLPALGKTQK  TGKRSTSAAV  LEALREAHPI  VEKILQHREL  TKLKNTYVDP  550

551  LPSLVHPRTG  RLHTRFNQTA  TATGRLSSSD  PNLQNIPVRT  PLGQRIRRAF  600

601  VAEAGWALVA  LDYSQIELRV  LAHLSGDENL  IRVFQEGKDI  HTQTASWMFG  650

651  VPPEAVDPLM  RRAAKTVNFG  VLYGMSAHRL  SQELAIPYEE  AVAFIERYFQ  700

701  SFPKVRAWIE  KTLEEGRKRG  YVETLFGRRR  YVPDLNARVK  SVREAAERMA  750

751  FNMPVQGTAA  DLMKLAMVKL  FPRLREMGAR  MLLQVHDELL  LEAPQARAEE  800

801  VAALAKEAME  KAYPLAVPLE  VEVGMGEDWL  SAKG                    834
```

Thus, the polypeptides of the invention encompass both naturally occurring proteins as well as variations, truncations and modified forms thereof. Such variants will continue to possess the desired activity. The deletions, insertions, and substitutions of the polypeptide sequence encompassed herein are not expected to produce radical changes in the characteristics of the polypeptide. One skilled in the art can readily evaluate the thermal stability and polymerase activity of the polypeptides and variant polypeptides of the invention by routine screening assays.

Kits and compositions containing the present polypeptides are substantially free of cellular material. Such preparations and compositions have less than about 30%, 20%, 10%, 5%, (by dry weight) of contaminating bacterial cellular protein.

The activity of nucleic acid polymerase polypeptides and variant polypeptides can be assessed by any procedure known to one of skill in the art. For example, the DNA synthetic activity of the variant and non-variant polymerase polypeptides of the invention can be tested in standard DNA sequencing or DNA primer extension reaction. One such assay can be performed in a 100 µl (final volume) reaction mixture, containing, for example, 0.1 mM dCTP, dTTP, dGTP, -$^{32}$P-dATP, 0.3 mg/ml activated calf thymus DNA and 0.5 mg/ml BSA in a buffer containing: 50 mM KCl, 1 mM DTT, 10 mM MgCl$_2$ and 50 mM of a buffering compound such as PIPES, Tris or Triethylamine. A dilution to 0.1 units/µl of each polymerase enzyme is prepared, and 5 µl of such a dilution is added to the reaction mixture, followed by incubation at 60 C for 10 minutes. Reaction products can be detected by determining the amount of $^{32}$P incorporated into DNA or by observing the products after separation on a polyacrylamide gel.

Uses for Nucleic Acid Polymerase Polypeptides

The thermostable enzymes of this invention may be used for any purpose in which DNA Polymerase or reverse transcriptase activity is necessary or desired. For example, the present nucleic acid polymerase polypeptides can be used in one or more of the following procedures: DNA sequencing, DNA amplification, RNA amplification, reverse transcription, DNA synthesis and/or primer extension. The nucleic acid polymerase polypeptides of the invention can be used to amplify DNA by polymerase chain reaction (PCR). The nucleic acid polymerase polypeptides of the invention can be used to sequence DNA by Sanger sequencing procedures. The nucleic acid polymerase polypeptides of the invention can also be used in primer extension reactions. The nucleic acid polymerase polypeptides of the invention can also be used for reverse transcription. The nucleic acid polymerase polypeptides of the invention can be used test for single nucleotide polymorphisms (SNPs) by single nucleotide primer extension using terminator nucleotides. Any such procedures and related procedures, for example, polynucleotide or primer labeling, minisequencing and the like are contemplated for use with the present nucleic acid polymerase polypeptides.

Methods of the invention comprise the step of extending a primed polynucleotide template with at least one labeled nucleotide, wherein the extension is catalyzed by a nucleic acid polymerase of the invention. Nucleic acid polymerases used for Sanger sequencing can produce fluorescently labeled products that are analyzed on an automated fluorescence-based sequencing apparatus such as an Applied Biosystems 310 or 377 (Applied Biosystems, Foster City, Calif.). Detailed protocols for Sanger sequencing are known to those skilled in the art and may be found, for example in Sambrook et al, Molecular Cloning, A Laboratory Manual, Second Edition, Cold Spring Harbor Press, Cold Spring Harbor, N.Y. (1989).

In one embodiment, the nucleic acid polymerase polypeptides of the invention are used for DNA amplification. Any procedure that employs a DNA polymerase can be used, for example, in polymerase chain reaction (PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195; 4,683,202; and 4,965,188, hereby incorporated by reference, which describe a method for increasing the concentration of a segment of a target sequence in a mixture of genomic DNA or other DNA or RNA without cloning or purification.

The PCR process for amplifying a target sequence consists of introducing a large excess of two oligonucleotide primers to the DNA mixture containing the desired target sequence, followed by a precise sequence of thermal cycling in the presence of a nucleic acid polymerase. The two primers are complementary to their respective strands of the double stranded target sequence. To effect amplification, the mixture is denatured and the primers annealed to their complementary sequences within the target molecule. Following annealing, the primers are extended with a polymerase so as to form a new pair of complementary strands. The steps of denaturation, primer annealing and polymerase extension can be repeated many times. Each round of denaturation, annealing and extension constitutes one "cycle." There can be numerous cycles, and the amount of amplified DNA produced increases with the number of cycles. Hence, to obtain a high concentration of an amplified target nucleic acid, many cycles are performed.

The steps involve in PCR nucleic acid amplification method are described in more detail below. For ease of discussion, the nucleic acid to be amplified is described as being double-stranded. However, the process is equally useful for amplifying a single-stranded nucleic acid, such as an mRNA, although the ultimate product is generally double-stranded DNA. In the amplification of a single-stranded nucleic acid, the first step involves the synthesis of a complementary strand (one of the two amplification primers can be used for this purpose), and the succeeding steps proceed as follows:

Each nucleic acid strand is contacted with four different nucleoside triphosphates and one oligonucleotide primer for each nucleic acid strand to be amplified, wherein each primer is selected to be substantially complementary to a portion the nucleic acid strand to be amplified, such that the extension product synthesized from one primer, when it is separated from its complement, can serve as a template for synthesis of the extension product of the other primer. To promote the proper annealing of primer(s) and the nucleic acid strands to be amplified, a temperature that allows hybridization of each primer to a complementary nucleic acid strand is used.

After primer annealing, a nucleic acid polymerase is used for primer extension that incorporates the nucleoside triphosphates into a growing nucleic acid strand that is complementary to the strand hybridized by the primer. In general, this primer extension reaction is performed at a temperature and for a time effective to promote the activity of the enzyme and to synthesize a "full length" complementary nucleic acid strand, that extends into a through a complete second primer binding. However, the temperature is not so high as to separate each extension product from its nucleic acid template strand.

The mixture from step (b) is then heated for a time and at a temperature sufficient to separate the primer extension products from their complementary templates. The temperature chosen is not so high as to irreversibly denature the nucleic acid polymerase present in the mixture.

The mixture from (c) is cooled for a time and at a temperature effective to promote hybridization of a primer to each of the single-stranded molecules produced in step (b).

The mixture from step (d) is maintained at a temperature and for a time sufficient to promote primer extension by DNA polymerase to produce a "full length" extension product. The temperature used is not so high as to separate each extension product from the complementary strand template. Steps (c)-(e) are repeated until the desired level of amplification is obtained.

The amplification method is useful not only for producing large amounts of a specific nucleic acid sequence of known sequence but also for producing nucleic acid sequences that are known to exist but are not completely specified. One need know only a sufficient number of bases at both ends of the sequence in sufficient detail so that two oligonucleotide primers can be prepared that will hybridize to different strands of the desired sequence at relative positions along the sequence such that an extension product synthesized from one primer, when separated from the template (complement), can serve as a template for extension of the other primer. The greater the knowledge about the bases at both ends of the sequence, the greater can be the specificity of the primers for the target nucleic acid sequence.

Thermally stable nucleic acid polymerases are therefore generally used for PCR because they can function at the high temperatures used for melting double stranded target DNA and annealing the primers during each cycle of the PCR reaction. High temperature results in thermodynamic conditions that favor primer hybridization with the target sequences and not hybridization with non-target sequences (H. A. Erlich (ed.), PCR Technology, Stockton Press [1989]).

The thermostable nucleic acid polymerases of the present invention satisfy the requirements for effective use in amplification reactions such as PCR. The present polymerases do not become irreversibly denatured (inactivated) when subjected to the required elevated temperatures for the time necessary to melt double-stranded nucleic acids during the amplification process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically denaturation can be done at temperatures ranging from about 90 C to about 105 C. The time required for denaturation depends mainly on the temperature and the length of the duplex nucleic acid. Typically the time needed for denaturation ranges from a few seconds up to four minutes. Higher temperatures may be required as the salt concentration of the buffer, or the length and/or GC composition of the nucleic acid is increased. The nucleic acid polymerases of the invention do not become irreversibly denatured for relatively short exposures to temperatures of about 90 C to 100 C.

The thermostable polymerases of the invention have an optimum temperature at which they function that is higher than about 45 C. Temperatures below 45 C facilitate hybridization of primer to template, but depending on salt composition and concentration and primer composition and length, hybridization of primer to template can occur at higher temperatures (e.g., 45 C to 70 C), which may promote specificity of the primer hybridization reaction. The polymerases of the invention exhibit activity over a broad temperature range from about 37 C to about 90 C.

The present polymerases have particular utility for PCR not only because of their thermal stability but also because of their ability to synthesize DNA using an RNA template and because of their fidelity in replicating the template nucleic acid. In most PCR reactions that start with an RNA template, reverse transcriptase must be added. However, use of reverse transcriptase has certain drawbacks. First, it is not stable at higher temperatures. Hence, once the initial complementary DNA (cDNA) has been made by reverse transcriptase and the thermal cycles of PCR are started, the original RNA template is not used as a template in the amplification reaction. Second, reverse transcriptase does not produce a cDNA copy with particularly good sequence fidelity. With PCR, it is possible to amplify a single copy of a specific target or template nucleic acid to a level detectable by several different methodologies. However, if the sequence of the target nucleic acid is not replicated with fidelity, then the amplified product can include a pool of nucleic acids with diverse sequences. Hence, the nucleic acid polymerases of the invention that can accurately reverse transcribe RNA and replicate the sequence of the template RNA or DNA with high fidelity is highly desirable.

Any nucleic acid can act as a "target nucleic acid" for the PCR methods of the invention. The term "target," when used in reference to the polymerase chain reaction, refers to the region of nucleic acid bounded by the primers used for polymerase chain reaction. In addition to genomic DNA and mRNA, any cDNA, RNA, oligonucleotide or polynucleotide can be amplified with the appropriate set of primer molecules. In particular, the amplified segments created by the PCR process itself are, themselves, efficient templates for subsequent PCR amplifications. The length of the amplified segment of the desired target sequence is determined by the relative positions of the primers with respect to each other, and therefore, this length is readily controlled.

The amplified target nucleic acid can be detected by any method known to one of skill in the art. For example, target nucleic acids are often amplified to such an extent that they form a band visible on a size separation gel. Target nucleic acids can also be detected by hybridization with a labeled probe; by incorporation of biotinylated primers during PCR followed by avidin-enzyme conjugate detection; by incorporation of $^{32}$P-labeled deoxynucleotide triphosphates during PCR, and the like.

The amount of amplification can also be monitored, for example, by use of a reporter-quencher oligonucleotide as described in U.S. Pat. No. 5,723,591, and a nucleic acid polymerase of the invention that has 5'-3' nuclease activity. The reporter-quencher oligonucleotide has an attached reporter molecule and an attached quencher molecule that is capable of quenching the fluorescence of the reporter molecule when the two are in proximity. Quenching occurs when the reporter-quencher oligonucleotide is not hybridized to a complementary nucleic acid because the reporter molecule and the quencher molecule tend to be in proximity or at an optimal distance for quenching. When hybridized, the reporter-quencher oligonucleotide emits more fluorescence than when unhybridized because the reporter molecule and the quencher molecule tend to be further apart. To monitor amplification, the reporter-quencher oligonucleotide is designed to hybridize 3' to an amplification primer. During amplification, the 5'-3' nuclease activity of the polymerase digests the reporter oligonucleotide probe, thereby separating the reporter molecule from the quencher molecule. As the amplification is conducted, the fluorescence of the reporter molecule increases. Accordingly, the amount of amplification performed can be quantified based on the increase of fluorescence observed.

Oligonucleotides used for PCR primers are usually about 9 to about 75 nucleotides, preferably about 17 to about 50 nucleotides in length. Preferably, an oligonucleotide for use in PCR reactions is about 40 or fewer nucleotides in length (e.g., 9, 12, 15, 18, 20, 21, 24, 27, 30, 35, 40, or any number between 9 and 40). Generally specific primers are at least about 14 nucleotides in length. For optimum specificity and cost effectiveness, primers of 16-24 nucleotides in length are generally preferred.

Those skilled in the art can readily design primers for use processes such as PCR. For example, potential primers for nucleic acid amplification can be used as probes to determine whether the primer is selective for a single target and what conditions permit hybridization of a primer to a target within a sample or complex mixture of nucleic acids.

The present invention also contemplates use of the present nucleic acid polymerases in combination with other procedures or enzymes. For example, the polymerases can be used in combination with additional reverse transcriptase or another DNA polymerase. See U.S. Pat. No. 5,322,770, incorporated by reference herein.

In another embodiment, nucleic acid polymerases of the invention with 5'-3' exonuclease activity are used to detect target nucleic acids in an invader-directed cleavage assay. This type of assay is described, for example, in U.S. Pat. No. 5,994,069. It is important to note that the 5'-3' exonuclease of DNA polymerases is not really an exonuclease that progressively cleaves nucleotides from the 5' end of a nucleic acid, but rather a nuclease that can cleave certain types of nucleic acid structures to produce oligonucleotide cleavage products. Such cleavage is sometimes called structure-specific cleavage.

In general, the invader-directed cleavage assay employs at least one pair of oligonucleotides that interact with a target nucleic acid to form a cleavage structure for the 5'-3' nuclease activity of the nucleic acid polymerase. Distinctive cleavage products are released when the cleavage structure is cleaved by the 5'-3' nuclease activity of the polymerase. Formation of such a target-dependent cleavage structure and the resulting cleavage products is indicative of the presence of specific target nucleic acid sequences in the test sample.

Therefore, in the invader-directed cleavage procedure, the 5'-3' nuclease activity of the present polymerases is needed as well at least one pair of oligonucleotides that interact with a target nucleic acid to form a cleavage structure for the 5'-3' nuclease. The first oligonucleotide, sometimes termed the "probe," can hybridize within the target site but downstream of a second oligonucleotide, sometimes termed an "invader" oligonucleotide. The invader oligonucleotide can hybridize adjacent and upstream of the probe oligonucleotide. However, the target sites to which the probe and invader oligonucleotides hybridize overlap such that the 3' segment of the invader oligonucleotide overlaps with the 5' segment of the probe oligonucleotide. The 5'-3' nuclease of the present polymerases can cleave the probe oligonucleotide at an internal site to produce distinctive fragments that are diagnostic of the presence of the target nucleic acid in a sample. Further details and methods for adapting the invader-directed cleavage assay to particular situations can be found in U.S. Pat. No. 5,994,069.

One or more nucleotide analogs can also be used with the present methods, kits and with the nucleic acid polymerases. Such nucleotide analogs can be modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

The invention also provides kits that contain at least one of the nucleic acid polymerases of the invention. Individual kits may be adapted for performing one or more of the following procedures: DNA sequencing, DNA amplification, RNA Amplification and/or primer extension. Kits of the invention comprise a DNA polymerase polypeptide of the invention and at least one nucleotide. A nucleotide provided in the kits of the invention can be labeled or unlabeled. Kits preferably can also contain instructions on how to perform the procedures for which the kits are adapted.

Optionally, the subject kit may further comprise at least one other reagent required for performing the method the kit is adapted to perform. Examples of such additional reagents include: another unlabeled nucleotide, another labeled nucleotide, a balance mixture of nucleotides, one or more chain terminating nucleotides, one or more nucleotide analogs, buffer solution(s), magnesium solution(s), cloning vectors, restriction endonucleases, sequencing primers, reverse transcriptase, and DNA or RNA amplification primers. The reagents included in the kits of the invention may be supplied in premeasured units so as to provide for greater precision and accuracy. Typically, kits reagents and other components are placed and contained in separate vessels. A reaction vessel, test tube, microwell tray, microtiter dish or other container can also be included in the kit. Different labels can be used on different reagents so that each reagent can be distinguished from another.

The following Examples further illustrate the invention and are not intended to limit the scope of the invention.

EXAMPLE 1

Cloning of a Nucleic Acid Polymerase from the RQ-1 and GK24 Strains of *Thermus thermophilus*

Bacteria Growth and Genomic DNA Isolation.

A bacterial sample of the *Thermus thermophilus* strain RQ-1 (Tth RQ-1) was obtained from the German Collection of Microorganisms (DSM catalog number 9247). The GK24 strain of *Thermus thermophilus* was obtained from Dr. R. A. D. Williams, Queen Mary and Westfield College, London, England. The lyophilized bacteria were revived in 4 ml of ATCC *Thermus* bacteria growth media 461 (Castenholtz TYE medium). The 4 ml overnight was grown at 65° C. in a water bath orbital shaker. The 4 ml culture was transferred to 200 ml of TYE and grown overnight at 65° C. in a water bath orbital shaker to stationary phase. Genomic DNA was prepared from these bacterial strains using a Qiagen genomic DNA preparation kit (Qiagen Inc., Valencia, Calif.).

Cloning of a Nucleic Acid Polymerase Gene from the RQ-1 and GK24 Strains of *Thermus thermophilus*

The forward and reverse primers were designed by analysis of 5' and 3' terminal homologous conserved regions of the Genebank DNA sequences of the DNA Pol I genes from *Thermus aquaticus* (Taq), *Thermus thermophilus* (Tth), *Thermus filiformis* (Tfi), *Thermus caldophilus*, and *Thermus flavus*. A gene fragment of a nucleic acid polymerase from the RQ-1 and GK24 strains of *Thermus thermophilus* were amplified using N-terminal primer 5'-atg gag gcg atg ctt ccg ctc ttt gaa c-3' (SEQ ID NO:25) and C-terminal primer 5'-gtc gac taa acg gca ggg ccc ccc taa cc-3' (SEQ ID NO:26). The following PCR reaction mixture contained 2.5 ul of 10× cPfu Turbo reaction buffer (Stratagene), 2 mM MgCl$_2$, 50 ng genomic DNA template, 0.2 mM (each) dNTPs, 20 pmol of each primer, and 10 units of Pfu Turbo DNA polymerase (Stratagene) in a 25 μl total reaction volume. The reaction was started by adding a premix containing enzyme, MgCl$_2$, dNTPs, buffer and water to another premix containing primer and template that had been preheated at 80° C. The entire reaction mixture was then denatured (30 s at 96° C.) followed by PCR cycling for 30 cycles (98° C. for 15 sec, 56° C. for 30 s, and 72° C. for 3 min) with a finishing step (72° C. for 6 min). This produced a 2.5 kb DNA fragment. These amplified fragments were purified from the PCR reaction mix using a Qiagen PCR cleanup kit (Qiagen Inc., Valencia, Calif.). The fragments were then ligated into the inducible expression vector pCR®T7 CT-TOPO® (Invitrogen, Carlsbad, Calif.). Three different polymerase clones were sequenced independently in order to rule out PCR errors, yielding the full-length consensus sequences the RQ-1 and GK24 strains of *Thermus thermophilus*. The nucleic acid sequence for the GK24 strain of *Thermus thermophilus* is provided as SEQ ID NO:1. The nucleic acid sequence for the RQ-1 strain of *Thermus thermophilus* is provided as SEQ ID NO:2. The amino acid sequence for the GK24 polymerase has SEQ ID NO:13. The amino acid sequence for the RQ-1 polymerase has SEQ ID NO:14.

Amino Acid Sequence Comparisons with Related *Thermus thermophilus* Polymerases

Comparison of the GK24 amino acid sequence (SEQ ID NO:13) with a published GK24 DNA Pol I sequence from Kwon et al., (Mol Cells. 1997 Apr. 30; 7 (2):264-71) revealed that SEQ ID NO:13 has four changes versus the Kwon sequence: Asn129→Lys, Pro130→Ala, Asp147→Tyr, and Gly797→Arg. These four positions are identified in bold in FIG. 1. In each of these four positions the Kwon GK24 DNA Pol I and a polypeptide with SEQ ID NO:13 have amino acids with dramatically different chemical properties. Asparagine (Kwon) is a polar, uncharged amino acid sidechain whereas lysine (SEQ ID NO:13) is charged and basic (N129K). Proline (Kwon) and alanine (SEQ ID NO:13) are both aliphatic but alanine promotes helix or beta sheet formation whereas prolines generally interrupt helices and sheets (Pro130→Ala, or P130A). Aspartate (Kwon) is an acidic amino acid and tyrosine (SEQ ID NO:13) is aromatic (Asp147→Tyr, or D147Y). Glycine (Kwon) is the smallest amino acid side chain whereas arginine (SEQ ID NO:13) has the longest, most basic charged sidechain (Gly797→Arg, or G797R).

SEQ ID NO:13 has three amino acid changes from the published sequence of *Thermus thermophilus* strain HB8 and twenty-two amino acid changes from the published sequence of *Thermus thermophilus* strain ZO5 (U.S. Pat. No. 5,674,738). These changes can be found in the amino acid alignment shown in FIG. 1.

Modification of Wild-Type *Thermus thermophilus*, Strain RQ1 and GK24 Polymerases In order to produce a polymerase in a form suitable for dye-terminator DNA sequencing, two substitutions were made to SEQ ID NO:1 and SEQ ID NO:2 to generate polypeptides with site-specific mutations. The mutations generated are the FS (Tabor and Richardson, 1995 PNAS 92: 6339-6343; U.S. Pat. No. 5,614,365) and exo-minus mutations (see U.S. Pat. No. 5,466,591; Xu Y., Derbyshire V., Ng K., Sun X-C., Grindley N. D., Joyce C. M. (1997) J. Mol. Biol. 268, 284-302). To reduce the exonuclease activity to very low levels, the mutation Gly46→Asp, or G46D was introduced. To reduce the discrimination between ddNTP's and dNTP's, the mutation Phe669→Tyr, or F669Y was introduced. The G46D and F669Y mutations are widely used with the Taq Pol I for DNA sequencing.

Mutagenesis of SEQ ID NO:1 and SEQ ID NO:2 was carried out using the modified QuickChange™ (Stratagene) PCR mutagenesis protocol described in Sawano & Miyawaki (2000). The mutagenized nucleic acids were resequenced completely to confirm the introduction of the mutations and to ensure that no PCR errors were introduced. A nucleic acid encoding the FS, exo-version of the GK24 polymerase of the invention is provided as SEQ ID NO:10, with amino acid sequence SEQ ID NO:22. A nucleic acid encoding the FS, exo-version of the RQ-1 polymerase of the invention is provided as SEQ ID NO:11, with amino acid sequence SEQ ID NO:23.

Protein Expression and Purification

Nucleic acids having SEQ ID NO:10 and SEQ ID NO:11 were separately inserted into the cloning vector pCR®T7 CT-TOPO® (Invitrogen, Carlsbad, Calif.) and these vectors were used to express the protein. BL21 *E. coli* cells (Invitrogen) were transformed with the vector containing SEQ ID NO:7 or SEQ ID NO:8. The cells were grown in one liter of Terrific Broth (Maniatis) to an optical density of 1.2 OD and the protein was overproduced by four-hour induction with 1.0 mM IPTG. The cells were harvested by centrifugation, washed in 50 mM Tris (pH 7.5), 5 mM EDTA, 5% glycerol, 10 mM EDTA to remove growth media, and the cell pellet frozen at −80° C.

To isolate the GK24 and RQ-1 polymerases, the cells were thawed and resuspended in 2.5 volumes (wet weight) of 50 mM Tris (pH 7.2), 400 mM NaCl, 1 mM EDTA. The cell walls were disrupted by sonication. The resulting E. coli cell debris was removed by centrifugation. The cleared lysate was pasteurized in a water bath (75° C., 45 min), denaturing and precipitating the majority of the non-thermostable E. coli proteins and leaving the thermostable GK24 (SEQ ID NO:22) and RQ-1 (SEQ ID NO:23) polymerases in solution. E. coli genomic DNA was removed by coprecipitation with 0.3% Polyethyleneimine (PEI). The cleared lysate was then applied to two columns in series: (1) a Biorex 70 cation exchange resin which chelates excess PEI and (2) a heparin-agarose column (dimensions to be provided) which retains the polymerase. This column was washed with 5 column volumes of 20 mM Tris (pH 8.5), 5% glycerol, 100 mM NaCl, 0.1 mM EDTA, 0.05% Triton X-100 and 0.05% Tween-20 (KTA buffer). The proteins were then eluted with a 0.1 to 1.0M NaCl linear gradient. The polymerases eluted at 0.8M NaCl. The eluted polymerases were concentrated and the buffer exchanged using a Millipore concentration filter (30 kD Mwt cutoff). The concentrated protein was stored at in KTA buffer (no salt) plus 50% glycerol at −20° C. The activity of the polymerase was measured using a salmon sperm DNA radiometric activity assay.

EXAMPLE 2

Cloning of a Nucleic Acid Polymerase from the 1b21 Strain of *Thermus thermophilus*

Bacteria Growth and Genomic DNA Isolation.

The 1b21 strain of *Thermus thermophilus* used in this invention was obtained from Dr. R. A. D. Williams, Queen Mary and Westfield College, London, England. The lyophilized bacteria were revived in 4 ml of ATCC *Thermus* bacteria growth media 461 (Castenholtz TYE medium). The 4 ml overnight was grown at 65° C. in a water bath orbital shaker. The 4 ml culture was transferred to 200 ml of TYE and grown overnight at 65° C. in a water bath orbital shaker to stationary phase. *Thermus thermophilus* 1b21 genomic DNA was prepared using a Qiagen genomic DNA preparation kit (Qiagen Inc., Valencia, Calif.).

Cloning of Nucleic Acids Encoding *Thermus thermophilus* 1b21 Polymerase

The forward and reverse primers were designed by analysis of 5' and 3' terminal homologous conserved regions of the Genebank DNA sequences of the DNA Pol I genes from *Thermus aquaticus* (Taq), *Thermus thermophilus* (Tth), *Thermus filiformis* (Tfi), *Thermus caldophilus*, and *Thermus flavus*. A *Thermus thermophilus* 1b21 genomic DNA fragment encoding part of the polymerase coding region was amplified using N-terminal primer 5'-atg gag gcg atg ctt ccg ctc ttt gaa c-3' (SEQ ID NO:27) and C-terminal primer 5'-gtc gac taa acg gca ggg ccc ccc taa cc-3' (SEQ ID NO:28). The following PCR reaction mixture contained 2.5 ul of 10× cPfu Turbo reaction buffer (Stratagene), 2 mM MgCl$_2$, 50 ng genomic DNA template, 0.2 mM (each) dNTPs, 20 pmol of each primer, and 10 units of Pfu Turbo DNA polymerase (Stratagene) in a 25 μl total reaction volume. The reaction was started by adding a premix containing enzyme, MgCl$_2$, dNTPs, buffer and water to another premix containing primer and template which had been preheated at 80° C. The entire reaction mixture was then denatured (30 s, 96° C.) followed by PCR cycling for 30 cycles (98° C. for 15 sec; 56° C. for 30 sec; 72° C. for 3 min) with a finishing step (72° C. for 6 min). This produced a 2.5 kb DNA fragment. This amplified fragment was purified from the PCR reaction mix using a Qiagen PCR cleanup kit (Qiagen Inc., Valencia, Calif.). The fragment was then ligated into the inducible expression vector pCR®T7 CT-TOPO® (Invitrogen, Carlsbad, Calif.). Three different *Thermus thermophilus* 1b21 genomic DNA fragments encoding the full-length gene were sequenced independently in order to rule out PCR errors. The resulting consensus sequence is SEQ ID NO:3, the nucleotide sequence for the polymerase isolated from *Thermus thermophilus*, strain 1b21. The amino acid sequence for the polymerase isolated from *Thermus thermophilus*, strain 1b21 is SEQ ID NO:15.

*Thermus thermophilus* 1b21 Polymerase Expression and Purification

A nucleic acid having SEQ ID NO:12 (containing FS and exo-mutations) was inserted into cloning vector pCR®T7 CT-TOPO® (Invitrogen, Carlsbad, Calif.) to express the protein. BL21 E. coli cells (Invitrogen) were transformed with this vector containing SEQ ID NO:12. The cells were grown in one liter of Terrific Broth (Maniatis) to an optical density of 1.2 OD and the protein was overproduced by four-hour induction with 1.0 mM IPTG. The cells were harvested by centrifugation, washed in 50 mM Tris (pH 7.5), 5 mM EDTA, 5% glycerol, 10 mM EDTA to remove growth media, and the cell pellet frozen at −80° C.

To isolate the *Thermus thermophilus*, strain 1b21 polymerase, the cells were thawed and resuspended in 2.5 volumes (wet weight) of 50 mM Tris (pH 7.2), 400 mM NaCl, 1 mM EDTA. The cell walls were disrupted by sonication. The resulting E. coli cell debris was removed by centrifugation. The cleared lysate was pasteurized in a water bath (75° C., 45 min), denaturing and precipitating the majority of the non-thermostable E. coli proteins and leaving the thermostable *Thermus thermophilus*, strain 1b21 polymerase in solution. E. coli genomic DNA was removed by coprecipitation with 0.3% Polyethyleneimine (PEI). The cleared lysate was then applied to two columns in series: (1) a Biorex 70 cation exchange resin which chelates excess PEI and (2) a heparin-agarose column (dimensions to be provided) which retains the polymerase. This column was washed with 5 column volumes of 20 mM Tris (pH 8.5), 5% glycerol, 100 mM NaCl, 0.1 mM EDTA, 0.05% Triton X-100 and 0.05% Tween-20 (KTA buffer). The protein was then eluted with a 0.1 to 1.0M NaCl linear gradient. The polymerase eluted at 0.8M NaCl. The eluted *Thermus thermophilus*, strain 1b21 polymerase was concentrated and the buffer exchanged using a Millipore concentration filter (30 kD Mwt cutoff). The concentrated protein was stored at in KTA buffer (no salt) plus 50% glycerol at −20° C. The activity of the polymerase was measured using a salmon sperm DNA radiometric activity assay.

REFERENCES

Tabor S., & Richardson C. C. A single residue in DNA polymerases of the *Escherichia coli* DNA polymerase I family is critical for distinguishing between deoxy- and dideoxyribonucleotides. Proc Natl Acad Sci USA. 1995. Vol. 92(14): 6339-43.

Sawano A. & Miyawaki A. Directed evolution of green fluorescent protein by a new versatile PCR strategy for site-directed and semi-random mutagenesis. Nucleic Acids Res. 2000. Vol. 28 (16): E78.

Kwon S. T., Kim J. S., Park J. H., Kim H. K., Lee D. S. Cloning and analysis of the DNA polymerase-encoding gene from *Thermus caldophilus* GK24. Mol. Cells. 1997. Vol. 7 (2): 264-71.

U.S. Pat. No. 5,455,170 to Abramson et al.

What is claimed:

1. An isolated nucleic acid polymerase comprising the amino acid sequence of SEQ ID NO:14.

2. A kit adapted for performing DNA sequencing, DNA amplification, reverse transcription, RNA amplification or primer extension comprising a container containing an isolated nucleic acid polymerase, wherein the nucleic acid polymerase comprises the amino acid sequence of SEQ ID NO:14.

3. The kit of claim 2 further comprising a container containing an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer.

4. The isolated nucleic acid polymerase of claim 1, wherein said nucleic acid polymerase is a DNA polymerase.

5. The isolated nucleic acid polymerase of claim 1, wherein said nucleic acid polymerase is from *Thermus thermophilus* strain RQ-1.

6. The isolated nucleic acid polymerase of claim 1, wherein said polymerase has a DNA polymerase activity between about 50,000 U/mg protein and 500,000 U/mg protein.

7. An isolated nucleic acid polymerase, wherein said polymerase has at least 99% amino acid identity to SEQ ID NO:14.

8. The isolated nucleic acid polymerase of claim 7, wherein said polymerase comprises a mutation that decreases 5'-3' exonuclease activity relative to 5'-3' exonuclease activity of SEQ ID NO:14.

9. The isolated nucleic acid polymerase of claim 8, wherein said polymerase has decreased 5'-3' exonuclease activity relative to a nucleic acid polymerase encoded by SEQ ID NO:14.

10. The isolated nucleic acid polymerase of claim 7, wherein said polymerase comprises a mutation that reduces discrimination against dideoxynucleotide triphosphates relative to dideoxynucleotide triphosphate discrimination of SEQ ID NO:14.

11. The isolated nucleic acid polymerase of claim 10, wherein said polymerase has reduced discrimination against dideoxynucleotide triphosphates relative to a nucleic acid polymerase encoded by SEQ ID NO:14.

12. A kit adapted for performing DNA sequencing, DNA amplification, reverse transcription, RNA amplification or primer extension comprising a container containing an isolated nucleic acid polymerase, wherein the nucleic acid polymerase comprises the isolated nucleic acid polymerase that has at least 99% amino acid identity to SEQ ID NO: 14.

13. The kit of claim 12 further comprising a container containing an unlabeled nucleotide, a labeled nucleotide, a balanced mixture of nucleotides, a chain terminating nucleotide, a nucleotide analog, a buffer solution, a solution containing magnesium, a cloning vector, a restriction endonuclease, a sequencing primer, a solution containing reverse transcriptase, or a DNA or RNA amplification primer.

* * * * *